United States Patent
Brecheen et al.

(10) Patent No.: US 8,323,278 B2
(45) Date of Patent: Dec. 4, 2012

(54) APPARATUS FOR TREATING A PORTION OF A REPRODUCTIVE SYSTEM AND RELATED METHODS OF USE

(75) Inventors: Roger M. Brecheen, Wilson, WY (US); John H. Koehler, Jackson, WY (US)

(73) Assignee: Soulor Surgical, Inc., Jackson, WY (US)

( * ) Notice: Subject to any disclaimer, the term of this patent is extended or adjusted under 35 U.S.C. 154(b) by 0 days.

(21) Appl. No.: 13/244,959

(22) Filed: Sep. 26, 2011

(65) Prior Publication Data

US 2012/0143210 A1 Jun. 7, 2012

Related U.S. Application Data

(63) Continuation of application No. 13/214,595, filed on Aug. 22, 2011.

(60) Provisional application No. 61/420,308, filed on Dec. 6, 2010.

(51) Int. Cl.
*A61B 18/14* (2006.01)
*A61B 17/32* (2006.01)

(52) U.S. Cl. .......................... 606/45; 606/170

(58) Field of Classification Search ............... 606/41, 606/45–49, 119, 167, 170
See application file for complete search history.

(56) References Cited

U.S. PATENT DOCUMENTS

| | | |
|---|---|---|
| 3,877,433 A | 4/1975 | Librach |
| 3,910,279 A | 10/1975 | Okada et al. |
| 3,926,192 A | 12/1975 | Van Maren |
| RE29,088 E | 12/1976 | Shaw |
| 4,000,743 A | 1/1977 | Weaver |
| 4,022,208 A | 5/1977 | Valtchev |
| 4,089,337 A | 5/1978 | Kronner et al. |
| 4,245,653 A | 1/1981 | Weaver |
| 4,430,076 A | 2/1984 | Harris |
| 4,672,964 A | 6/1987 | Dee et al. |
| 4,775,362 A | 10/1988 | Kronner |

(Continued)

FOREIGN PATENT DOCUMENTS

EP 0 319 394 A1 6/1989

(Continued)

OTHER PUBLICATIONS

PCT International Search Report and Written Opinion issued by the U.S. Patent and Trademark Office for corresponding International application No. PCT/US2011/051433 dated Nov. 16, 2011 (14 pages).

*Primary Examiner* — Linda Dvorak
*Assistant Examiner* — Samantha Good
(74) *Attorney, Agent, or Firm* — Finnegan, Henderson, Farabow, Garrett & Dunner L.L.P.

(57) ABSTRACT

A medical device for performing a surgical procedure may include an elongate member having a proximal end, a distal end, and a lumen extending therebetween. The medical device may also include a handle connected to the proximal end of the elongate member, an end effector assembly connected to the distal end of the elongate member, and a cutting device configured to extend from the end effector assembly, wherein the cutting device has a retracted configuration in which the cutting device is withdrawn into the end effector assembly and a deployed configuration in which the cutting device extends from the end effector assembly.

28 Claims, 37 Drawing Sheets

U.S. PATENT DOCUMENTS

| | | |
|---|---|---|
| 4,887,598 A | 12/1989 | Berke |
| 5,104,377 A | 4/1992 | Levine |
| 5,108,408 A | 4/1992 | Lally |
| 5,209,754 A | 5/1993 | Ahluwalia |
| 5,237,985 A | 8/1993 | Hodgson et al. |
| 5,259,836 A | 11/1993 | Thurmond et al. |
| 5,368,598 A | 11/1994 | Hasson |
| 5,382,252 A | 1/1995 | Failla et al. |
| 5,394,863 A | 3/1995 | Sanford et al. |
| 5,409,496 A | 4/1995 | Rowden et al. |
| 5,431,662 A | 7/1995 | Nicholas |
| 5,445,643 A | 8/1995 | Valtchev |
| 5,464,409 A | 11/1995 | Mohajer |
| 5,487,377 A | 1/1996 | Smith et al. |
| 5,520,698 A | 5/1996 | Koh |
| 5,540,700 A | 7/1996 | Rowden et al. |
| 5,549,563 A | 8/1996 | Kronner |
| 5,554,160 A | 9/1996 | Caillouette |
| 5,556,401 A | 9/1996 | Caillouette |
| 5,562,679 A | 10/1996 | Valtchev |
| 5,571,115 A | 11/1996 | Nicholas |
| 5,578,048 A | 11/1996 | Pasqualucci et al. |
| 5,580,067 A | 12/1996 | Hamblin et al. |
| 5,624,399 A | 4/1997 | Ackerman |
| 5,643,285 A | 7/1997 | Rowden et al. |
| 5,643,311 A | 7/1997 | Smith et al. |
| 5,645,561 A | 7/1997 | Smith et al. |
| 5,746,750 A | 5/1998 | Prestel et al. |
| 5,840,077 A | 11/1998 | Rowden et al. |
| 5,935,098 A | 8/1999 | Blaisdell et al. |
| 5,951,465 A | 9/1999 | Schiff et al. |
| 6,045,566 A * | 4/2000 | Pagedas .................... 606/167 |
| 6,048,345 A | 4/2000 | Berke et al. |
| 6,080,129 A | 6/2000 | Blaisdell |
| 6,086,603 A | 7/2000 | Termin et al. |
| 6,123,703 A | 9/2000 | Tu et al. |
| 6,156,006 A | 12/2000 | Brosens et al. |
| 6,174,317 B1 | 1/2001 | Engman |
| 6,176,858 B1 | 1/2001 | Dequesne et al. |
| 6,235,037 B1 | 5/2001 | East et al. |
| 6,254,601 B1 | 7/2001 | Burbank et al. |
| 6,293,952 B1 | 9/2001 | Brosens et al. |
| 6,346,085 B1 | 2/2002 | Schiffman |
| 6,423,075 B1 | 7/2002 | Singh et al. |
| 6,572,631 B1 | 6/2003 | McCartney |
| 6,602,251 B2 | 8/2003 | Burbank et al. |
| 6,641,581 B2 | 11/2003 | Muzzammel |
| 6,764,488 B1 | 7/2004 | Burbank et al. |
| 6,905,506 B2 | 6/2005 | Burbank et al. |
| 6,960,210 B2 | 11/2005 | Lands et al. |
| 7,083,615 B2 | 8/2006 | Peterson et al. |
| 7,135,018 B2 | 11/2006 | Ryan et al. |
| 7,147,638 B2 | 12/2006 | Chapman et al. |
| 7,172,603 B2 | 2/2007 | Burbank et al. |
| 7,175,634 B2 | 2/2007 | Van Heerden |
| 7,223,279 B2 | 5/2007 | Burbank et al. |
| 7,278,994 B2 | 10/2007 | Goble |
| 7,325,546 B2 | 2/2008 | Burbank et al. |
| 7,404,821 B2 | 7/2008 | Burbank et al. |
| 7,479,145 B2 | 1/2009 | Burbank et al. |
| 7,488,319 B2 | 2/2009 | Yates |
| 7,594,890 B2 | 9/2009 | Burbank et al. |
| 7,641,651 B2 | 1/2010 | Nezhat et al. |
| 7,686,817 B2 | 3/2010 | Burbank et al. |
| 7,763,033 B2 | 7/2010 | Gruber et al. |
| 7,771,357 B2 | 8/2010 | Burbank et al. |
| 7,806,894 B1 | 10/2010 | Rosenblatt et al. |
| 7,828,798 B2 | 11/2010 | Buysse et al. |
| 7,875,036 B2 | 1/2011 | Burbank et al. |
| 8,025,656 B2 | 9/2011 | Gruber et al. |
| 8,025,670 B2 | 9/2011 | Sharp et al. |
| 8,079,963 B2 | 12/2011 | Rosenblatt |
| 8,082,925 B2 | 12/2011 | McCartney |
| 2001/0021854 A1 | 9/2001 | Donnez |
| 2002/0120265 A1 | 8/2002 | Fowler |
| 2003/0109872 A1 | 6/2003 | Muzzammel |
| 2003/0187334 A1 | 10/2003 | Biswas |
| 2003/0216731 A1 | 11/2003 | Dennis |
| 2004/0097961 A1 | 5/2004 | Burbank et al. |
| 2004/0102770 A1 | 5/2004 | Goble |
| 2004/0158262 A1 | 8/2004 | Burbank et al. |
| 2004/0267157 A1 | 12/2004 | Miller et al. |
| 2005/0070895 A1 | 3/2005 | Ryan et al. |
| 2005/0085827 A1 | 4/2005 | G. et al. |
| 2005/0107818 A1 | 5/2005 | Valtchev |
| 2005/0149101 A1 | 7/2005 | Huschmand Nia |
| 2005/0261714 A1 | 11/2005 | McCartney |
| 2006/0058831 A1 | 3/2006 | Atad |
| 2006/0241652 A1 | 10/2006 | Doll et al. |
| 2006/0259035 A1 | 11/2006 | Nezhat et al. |
| 2006/0271037 A1 | 11/2006 | Maroney et al. |
| 2006/0293645 A1 | 12/2006 | Hibner |
| 2007/0112356 A1 | 5/2007 | McCartney |
| 2007/0173863 A1 | 7/2007 | Burbank et al. |
| 2007/0203505 A1 | 8/2007 | Burbank et al. |
| 2007/0260265 A1 | 11/2007 | Walter |
| 2008/0009854 A1 | 1/2008 | Yates |
| 2008/0039874 A1 | 2/2008 | Catanese et al. |
| 2008/0039894 A1 | 2/2008 | Catanese et al. |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0097473 A1 | 4/2008 | Burbank et al. |
| 2008/0109010 A1 | 5/2008 | Feuer et al. |
| 2008/0119868 A1 | 5/2008 | Sharp et al. |
| 2008/0132930 A1 | 6/2008 | Lubock et al. |
| 2008/0146872 A1 | 6/2008 | Gruber et al. |
| 2008/0146873 A1 | 6/2008 | Adams et al. |
| 2008/0154244 A1 | 6/2008 | Singh |
| 2008/0188863 A1 | 8/2008 | Chu |
| 2008/0200924 A1 | 8/2008 | Burbank et al. |
| 2008/0208210 A1 | 8/2008 | Blair et al. |
| 2008/0208233 A1 | 8/2008 | Barnes et al. |
| 2008/0245371 A1 | 10/2008 | Gruber |
| 2008/0249535 A1 | 10/2008 | Valtchev |
| 2008/0249553 A1 | 10/2008 | Gruber et al. |
| 2009/0048609 A1 | 2/2009 | Atiomo et al. |
| 2009/0112254 A1 | 4/2009 | Yates |
| 2009/0131954 A1 | 5/2009 | Christian et al. |
| 2009/0137970 A1 | 5/2009 | George et al. |
| 2009/0143639 A1 | 6/2009 | Stark |
| 2009/0182329 A1 | 7/2009 | Dycus |
| 2009/0209973 A1 | 8/2009 | East |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0106163 A1 | 4/2010 | Blair et al. |
| 2010/0160928 A1 | 6/2010 | Navas et al. |
| 2010/0180422 A1 | 7/2010 | Valtchev |
| 2010/0274260 A1 | 10/2010 | D'Arpiany et al. |
| 2010/0280524 A1 | 11/2010 | Lopez Zepeda |
| 2010/0287757 A1 | 11/2010 | Valtchev |
| 2010/0305566 A1 | 12/2010 | Rosenblatt et al. |
| 2010/0305578 A1 | 12/2010 | Auerbach et al. |
| 2011/0034943 A1 | 2/2011 | Churchill et al. |
| 2011/0054488 A1 | 3/2011 | Gruber et al. |
| 2011/0077674 A1 | 3/2011 | Sullivan et al. |
| 2011/0092982 A1 | 4/2011 | Hahn et al. |
| 2011/0112360 A1 | 5/2011 | Swann et al. |
| 2011/0112370 A1 | 5/2011 | Nguyen et al. |
| 2011/0118718 A1 | 5/2011 | Toth et al. |
| 2011/0130769 A1 | 6/2011 | Boebel et al. |
| 2011/0166508 A1 | 7/2011 | Lyyikainen et al. |
| 2011/0172593 A1 | 7/2011 | Lyyikainen et al. |
| 2011/0224486 A1 | 9/2011 | Nguyen et al. |
| 2011/0259344 A1 | 10/2011 | Ahluwalia |
| 2011/0306829 A1 | 12/2011 | Sharp et al. |

FOREIGN PATENT DOCUMENTS

| | | |
|---|---|---|
| EP | 0 392 319 B1 | 10/1990 |
| EP | 0 806 183 A1 | 5/1997 |
| EP | 2 243 437 A1 | 4/2010 |
| WO | WO 94/10926 A1 | 11/1993 |
| WO | WO 96/03930 A1 | 2/1996 |

| | | |
|---|---|---|
| WO | WO 03/015643 A2 | 2/2003 |
| WO | WO 03/096912 A1 | 11/2003 |
| WO | WO 2008/048764 A1 | 4/2008 |
| WO | WO 2008/124641 A2 | 10/2008 |
| WO | WO 2008/136024 A1 | 11/2008 |
| WO | WO 2010/036721 A2 | 4/2010 |
| WO | WO 2010/127171 A1 | 11/2010 |
| WO | WO 2010/127174 A1 | 11/2010 |
| WO | WO 2010/137973 A1 | 12/2010 |
| WO | WO 2010/151429 A2 | 12/2010 |

* cited by examiner

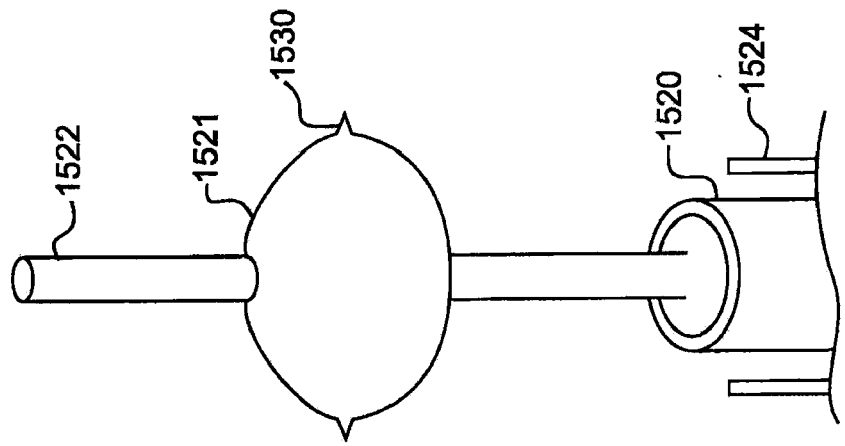
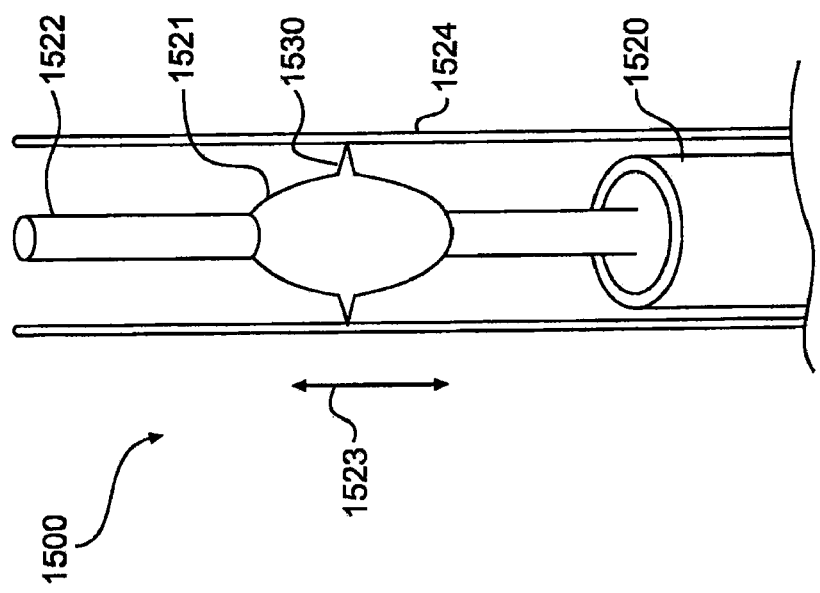
FIG. 33B
FIG. 33A

APPARATUS FOR TREATING A PORTION OF A REPRODUCTIVE SYSTEM AND RELATED METHODS OF USE

CROSS-REFERENCE TO RELATED APPLICATION

This patent application is a continuation of U.S. patent application Ser. No. 13/214,595, filed on Aug. 22, 2011, entitled APPARATUS FOR TREATING A PORTION OF A REPRODUCTIVE SYSTEM AND RELATED METHODS OF USE, which claims the benefits of priority under 35 U.S.C. §§119-120 to U.S. Provisional Application No. 61/420,308, filed on Dec. 6, 2010, entitled IMPROVED METHOD FOR TOTAL LAPROSCOPIC HYSTERECTOMY AND LAPROSCOPIC SUPRACERVICAL HYSTERECTOMY USING A NOVEL UTERINE AMPUTATION DEVICE, the entire disclosures of which are incorporated herein by reference.

FIELD OF THE INVENTION

Embodiments of the present disclosure generally relate to devices and methods for treating a portion of a reproductive system of a female patient. More particularly, embodiments of the present disclosure relate to devices and methods for uterine amputation, among other things.

BACKGROUND OF THE INVENTION

The female reproductive system includes, among other things, ovaries, fallopian tubes, a uterus, a cervix, and a vagina. As a result of certain gynecological conditions, such as cancers or severe pain and heavy bleeding, however, it sometimes becomes necessary to treat a patient's uterus. One option for treating the uterus includes surgically removing the uterus via a hysterectomy procedure.

One hysterectomy procedure is known as a radical hysterectomy and it involves the complete removal of a patient's uterus, cervix, upper vagina, and parametrium. Another hysterectomy procedure is known as a total hysterectomy and it involves the complete removal of a patient's uterus and cervix. In some cases, however, a patient may only require a supracervical hysterectomy (also known as a partial hysterectomy), which involves the removal of the uterus but otherwise leaves the cervix in situ.

Initially, hysterectomy procedures were performed via an incision in a patient's abdomen. With advancement in surgical tools and procedures, however, hysterectomy procedures have evolved to include vaginal and laparoscopic techniques. Today, therefore, hysterectomy procedures typically involve one of four primary approaches: total abdominal hysterectomy (TAH), total vaginal hysterectomy (TVH), total laparoscopic hysterectomy (TLH), and laparoscopic supracervical hysterectomy (LSH).

The medical literature has increasingly shown that the TLH and LSH approaches are preferred over the conventional TAH and TVH approaches. The TLH and LSH approaches are preferred because of several patient benefits, including, for example, less postoperative pain, shorter hospital stays, and faster recovery times. However, only a small percentage of hysterectomies performed each year are conducted via the TLH or LSH approach. Often, the reasons for performing a hysterectomy without using a TLH or LSH approach include the inherent limitations of laparoscopic surgery in general. These limitations include limited visibility, difficulty in manipulating internal organs with laparoscopic tools, and subsequent control of the operative field. In addition, surgeons often cite an increase in complication rates for avoiding TLH or LSH approaches. One such complication includes vaginal cuff dehiscence, which is thought to be caused by a tendency to "wander" during the cauterization/cutting procedure used to excise the uterus. Accordingly, there is a need for apparatuses and methods that are less invasive, allow for uniform excision, and/or reduce operation time.

SUMMARY OF THE INVENTION

Embodiments of the present disclosure provide apparatuses and methods for treating a portion of a reproductive system.

An aspect of the present disclosure includes a medical device for performing a surgical procedure. The medical device may include an elongate member having a proximal end, a distal end, and a lumen extending therebetween. The medical device may also include a handle connected to the proximal end of the elongate member, an end effector assembly connected to the distal end of the elongate member, and a cutting device configured to extend from the end effector assembly, wherein the cutting device has a retracted configuration in which the cutting device is withdrawn into the end effector assembly and a deployed configuration in which the cutting device extends from the end effector assembly.

In various embodiments, the medical device may include one or more of the following additional features: the end effector assembly may include a cup; the end effector assembly may include an elongate manipulation member having a proximal portion, a distal portion, and a central portion extending therebetween, wherein the central portion may include a substantially uniform cross-section; the cutting device may be further configured to rotate about a longitudinal axis of the end effector assembly; a first actuator may control deployment of the cutting device and a second actuator may control rotation of the cutting device; the cutting device may be a monopolar cauterizing instrument; the cutting device may be a bipolar cauterizing instrument; the medical device may further comprise an expandable member secured to a distal portion of the medical device; the expandable member may be secured to the elongate member; the medical device may further comprise an expandable member secured to the elongate manipulation member; the medical device may further comprise an elongate manipulation member extending distally from within the cup; the medical device may further comprise a first expandable member secured to a distal portion of the elongate member; the medical device may further comprise a second expandable member secured to the elongate manipulation member; the cup may include a first cup portion and a second cup portion disposed within the first cup portion, wherein a gap exists between the first and second cup portions, and the cutting device is slidably disposed within the gap; the cutting device may be a cautery ring; the cautery ring may include a segmented ring; the expandable member may be disposed proximally of the end effector assembly; the end effector assembly may be configured to pivot relative to the elongate member; the end effector assembly may be removably secured to the distal end of the elongate member; and the end effector assembly may be longitudinally movable relative to a distal end of the elongate member.

In another aspect, a method for performing a laparoscopic hysterectomy procedure may include inserting a medical device into a vaginal canal of a patient. The medical device may include an elongate member having a proximal end, a distal end, and a lumen extending therebetween, a handle connected to the proximal end of the elongate member, an end effector assembly connected to the distal end of the elongate member, and a cutting device configured to extend from the end effector assembly, wherein the cutting device has a retracted configuration in which the cutting device is withdrawn into the end effector assembly and a deployed configuration in which the end effector extends from the end effector assembly. The method may further include positioning the end effector adjacent tissue associated with one of uterine or cervical tissues, deploying the cutting device, and creating an incision to excise at least a uterus of the patient from surrounding tissue.

In various embodiments, the medical device may include one or more of the following additional features: the end effector may include a cup and an elongate manipulation member extending distally from within the cup; the medical device may further include a first expandable member disposed on the elongate member at a location proximal of the end effector assembly; the method may further comprise expanding the expandable member to occlude the vaginal canal; prior to the step of deploying the cutting device, the method may further include pivoting the elongate manipulation member to alter a positioning of the uterus; prior to the step of deploying the cutting device, the method may further include positioning a rim of the cup against a vaginal fornice and exerting a cephalad force on the vaginal fornice; creating an incision to separate at least a uterus of the patient from surrounding tissue may include rotating the cutting device; the cutting device may be a monopolar cautery instrument; the cutting device may be a bipolar cautery instrument; the medical device may include a second expandable member secured to the elongate manipulation member; the cutting device may be a cautery ring; the cautery ring may include a segmented ring; rotating the cutting device may include rotating the end effector assembly; the end effector assembly may be removably secured to the distal end of the elongate member; the end effector assembly may be longitudinally movable relative to the distal end of the elongate member; the method may further comprise the step of removing cervical tissue; and creating an incision to excise at least a uterus of the patient from surrounding tissue may include excising the uterus and a cervix of the patient.

A further aspect may include a medical device for performing a surgical procedure. The medical device may include an elongate member having a proximal end, a distal end, and a lumen extending therebetween, a handle connected to the proximal end of the elongate member, an end effector assembly connected to the distal end of the elongate member, a cutting device configured to extend from the end effector assembly, wherein the cutting device has a retracted configuration in which the cutting device is withdrawn into the end effector assembly and a deployed configuration in which the cutting device extends from the end effector assembly, wherein the cutting device is configured to rotate about a longitudinal axis of the end effector assembly, and wherein the cutting device includes a cauterizing instrument. The medical device may also include an expandable member positioned on the elongate member at a location proximal of the end effector assembly.

Additional objects and advantages of the disclosure will be set forth in part in the description that follows, and in part will be obvious from the description, or may be learned by practice of the disclosed embodiments. The objects and advantages of the disclosure will be realized and attained by means of the elements and combinations particularly pointed out in the appended claims.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 33A-33B depict an embodiment of a cutting device in retracted and deployed positions, respectively.

DESCRIPTION OF THE EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure generally relate to medical devices and methods for performing female pelvic surgical procedures, which may include, but are not limited to, removing a body organ such as a uterus or other structure associated with a reproductive system. More particularly, embodiments of the present disclosure relate to devices and methods for performing total laparoscopic hysterectomy (TLH) and laparoscopic supracervical hysterectomy (LSH) procedures. It should be emphasized, however, that the embodiments of the present disclosure may also be utilized in abdominal hysterectomies and other female pelvic surgical procedures. Furthermore, at least the devices disclosed herein may be used in the removal of other organs in both males and females.

Figure 1:
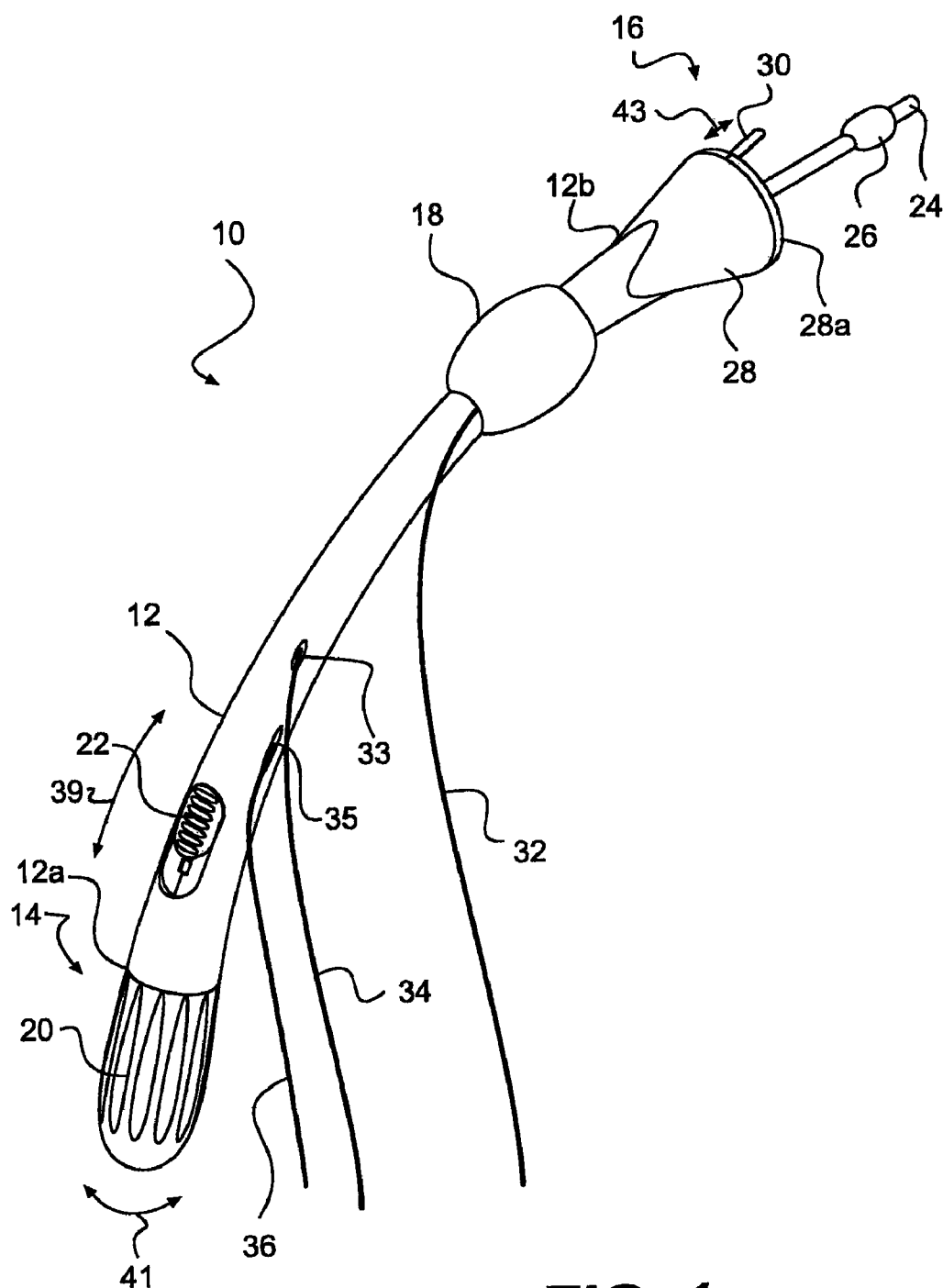
FIG. 1 is a perspective view of a medical device for performing a total laparoscopic hysterectomy (TLH) procedure, according to a first embodiment of the present disclosure.

FIG. 1 illustrates a medical device 10 for performing a TLH procedure, in accordance with a first embodiment of the present disclosure. Medical device 10 may include an elongate member 12, an end effector assembly 16, and a handle portion 14. For purposes of this disclosure, "proximal" refers to the end closer to the device operator during use, and "distal" refers to the end further from the device operator during use. End effector assembly 16 may be disposed at a distal end portion 12b of elongate member 12, and handle portion 14 may be disposed at a proximal end portion 12a of elongate member 12.

Elongate member 12 may be a unitary hollow structure, including, but not limited to, a curved tube made from any known suitable biocompatible material having sufficient flexibility and/or rigidity to traverse a vaginal canal. Alternatively, elongate member 12 may include two halves 13, 15 (FIG. 3) that may be connected by welding, soldering, or any other connection means known to those skilled in the art. Biocompatible materials may include, but are not limited to, rubber, silicon, synthetic plastics, stainless steel, ePTFE, PTFE, metal-polymer composites, and metal alloys of nickel, titanium, copper cobalt, vanadium, chromium, and iron. In one embodiment, the material forming elongate member 12 may be a superelastic material such as nitinol, which is a nickel-titanium alloy.

Elongate member 12 may have any desired cross-sectional shape and desired dimension, so long as it may be received in a vaginal canal. Elongate member 12 may also have an atraumatic exterior configuration. Such exterior configurations may include, but are not limited to, a rounded external surface. In addition, elongate member 12 may have any suitable coating such as, for example, an anesthetic or lubricious coating on an exterior surface of elongate member 12. Elongate member 12 may further include one or more lumens or internal channels (not shown) for the passage of a variety of surgical equipment, including, but not limited to, imaging devices and tools for irrigation, insufflation, vacuum suctioning, biopsies, and drug delivery. In one embodiment, medical device 10 may also include multiple openings 33, 35 in its exterior surface. The openings 33, 35 may be connected to the one or more lumens/channels in elongate member 12, which may be used as an entrance/exit location for an electrical line 36 providing electrical current to medical device 10 or for expansion lines 32, 34 providing an expansion source to expandable members 18, 26.

End effector assembly 16 may extend distally from distal end portion 12b of elongate member 12. End effector assembly 16 may be made integrally with elongate member 12. Alternatively, end effector assembly 16 may be a separate portion rigidly secured to elongate member 12 through any connection means known to those skilled in the art. Such connection means may include, but are not limited to, welding and soldering. An advantage of having end effector assembly 16 being a separate portion from elongate member 12 includes ease of sterilizing end effector assembly 16 after use. End effector assembly 16 may be re-usable or disposable. A disconnectable end effector assembly 16 may also allow for a device operator to have multiple end effector assemblies 16 in a variety of dimensions, such that the device operator can choose an appropriately sized end effector assembly 16 based on a patient's anatomy.

End effector assembly 16 may include multiple components, including, but not limited to, a cup 28, a manipulation device 24, and a cutting device 30. End effector assembly 16 may also have suitable illumination and imaging devices (not shown). The illumination device may be used to illuminate and help demarcation of the bladder and vasculature. Cup 28 may have any suitable shape and/or configuration, and may be any desired dimension such that it may be received in a patient's vaginal cavity. In the embodiment illustrated in FIG. 1, cup 28 may include a rounded perimeter forming a circular or oval shape.

Cup 28 may also include a substantially conical shape that tapers into an enlarged edge 28a. Enlarged edge 28a may have any suitable atraumatic configuration. For example, edge 28a may be rounded. Edge 28a may also have a textured geometry or other geometric configuration (e.g., tines, barbs, etc.) to aid in frictionally gripping patient tissue to maintain desired placement of medical device 10. An exterior surface of cup 28 may have an atraumatic configuration like that of the exterior surface of elongate member 12. Such atraumatic configurations may include, but are not limited to, a smoothed material surface. In addition, portions of cup 28 may include any suitable coating, including, but not limited to, an anesthetic or lubricious coating on an exterior of cup 28.

Figure 4A:
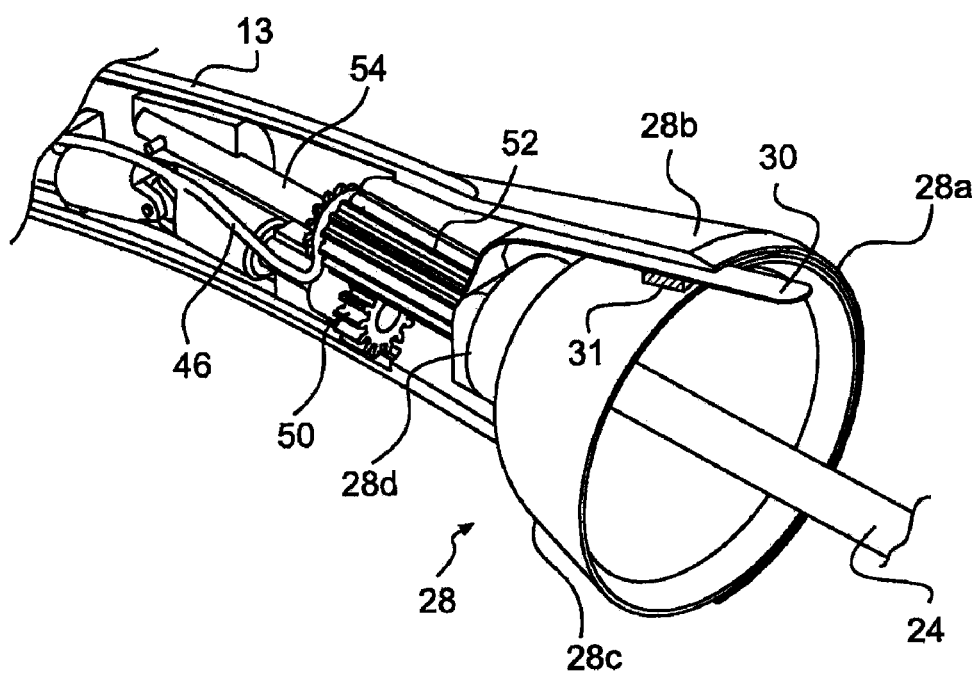
FIG. 4A is a sectional view of a distal end of the medical device of FIG. 1.

FIG. 4A illustrates an embodiment of cup 28. Cup 28 may include an inner cup portion 28c positioned within an outer cup portion 28b. There may be enough space between inner cup portion 28c and outer cup portion 28b to allow cutting device 30 to move between the directions indicated by arrow 43 (FIG. 1) and rotated along the directions indicated by arrow 45 (FIG. 2B). Cup 28 may also include a sealing mechanism 31, through which cutting device 30 may protrude, to keep unwanted material (e.g., tissue or blood) from entering a space between inner cup portion 28c and outer cup portion 28b. Sealing mechanism 31 may also limit the back and forth (e.g., lateral) motion of cutting device 30 within the space, so as to avoid potential wandering of cutting device 30 as cutting device 30 is moved along the directions indicated by arrow 45. In one embodiment, sealing mechanism 31 may include a strip of elastomeric material that engages a portion of cutting member 30. Although FIG. 4A shows a single sealing mechanism 31, those of ordinary skill in the art will understand that any suitable number of sealing mechanisms 31 may be provided. For example, a second sealing mechanism may be disposed on inner cup portion 28c.

Figure 2A:
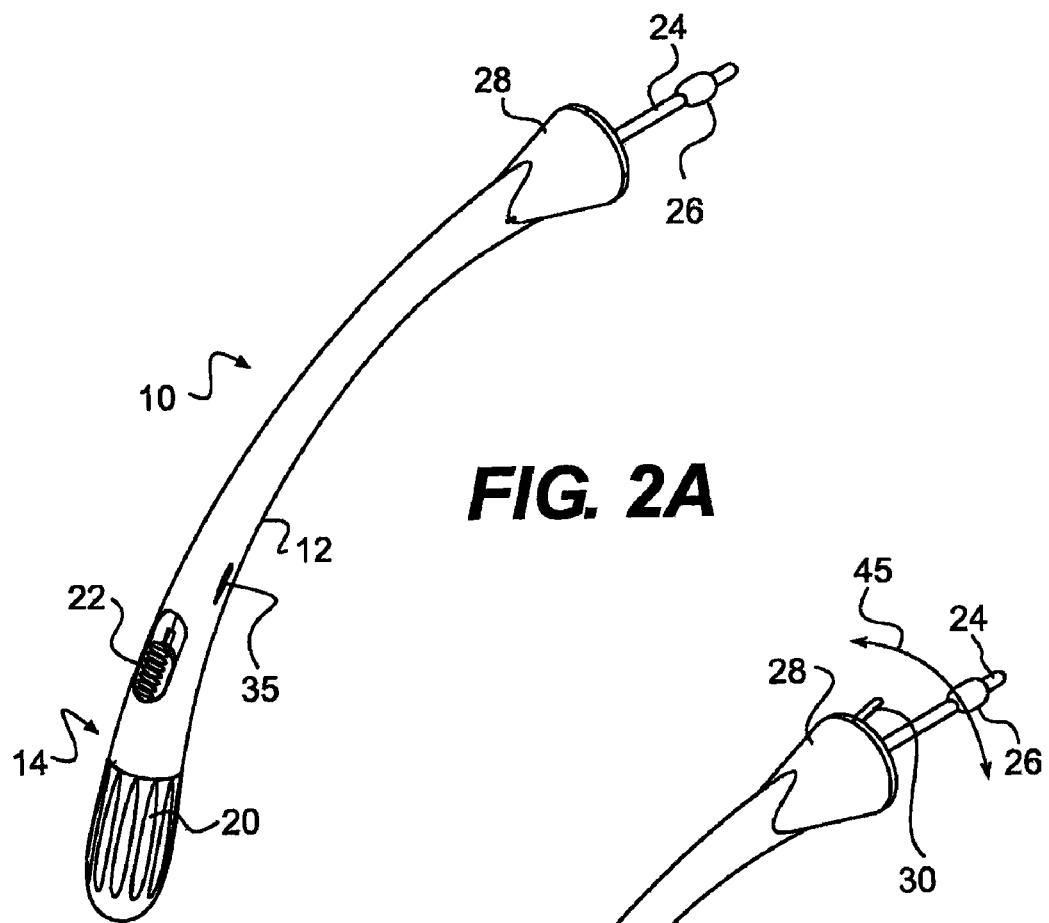
FIG. 2A is a perspective view of the medical device of FIG. 1 having a cutting device in a retracted position.
Figure 2B:
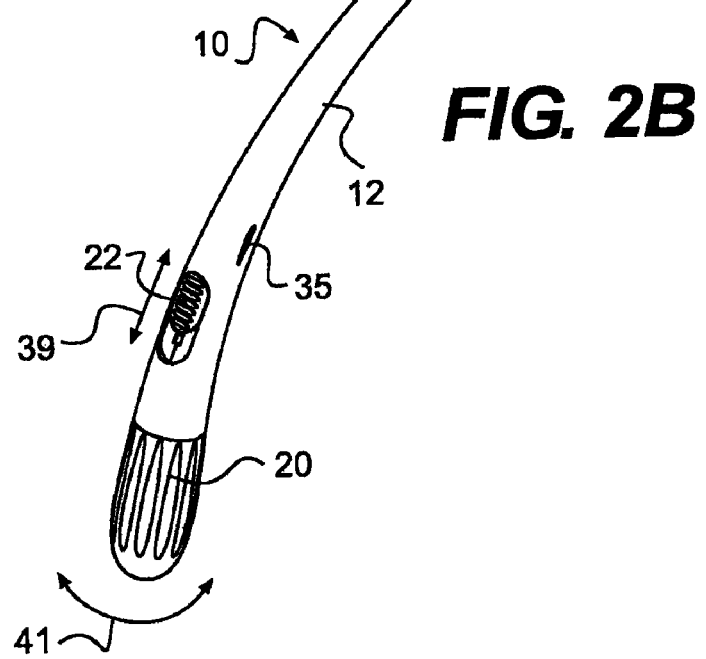
FIG. 2B is a perspective view of the medical device of FIG. 1 having a cutting device in a deployed position.
Figure 3:
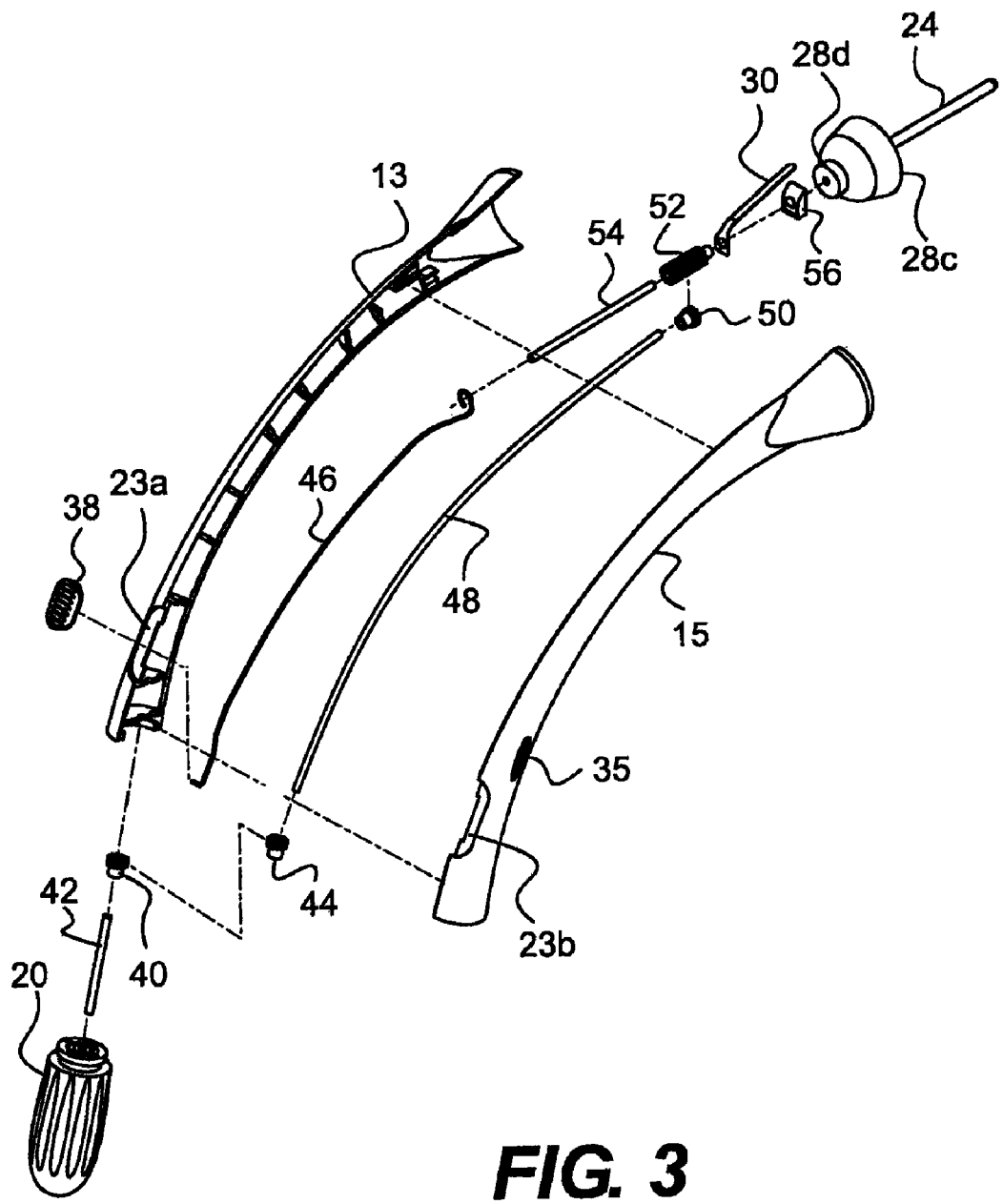
FIG. 3 is an exploded view of the medical device of FIG. 1.

Cutting device 30 may be configured to move relative to edge 28a between a retracted position shown in FIG. 2A and a deployed position shown in FIG. 2B along the directions shown by arrow 43 (FIG. 1). Movement between the deployed and retracted positions may be accomplished via a first actuating mechanism 22. In one embodiment, first actuating mechanism 22 may be a slide actuator 38 connected to a proximal end of a first rod 46 within elongate member 12. First rod 46 may be operatively connected to cutting device 30 at its distal end via coupling member 54 and clear 52, as shown in FIG. 3. Accordingly, axial movement of first actuating mechanism 22 in the directions indicated by arrow 39 may cause axial movement of cutting device 30 in the directions indicated by arrow 43. It is contemplated, however, that first actuating mechanism 22 may be a button or any other actuating mechanism known to one skilled in the art for controlled deployment of cutting device 30. First actuating mechanism 22 may also include a stop 56 within medical device 10 for preventing cutting device 30 from being deployed beyond a desired distance. First actuating mechanism 22 may also include a ratcheting detent or locking mechanism to maintain cutting device 30 at its desired deployed or retracted orientations.

Cutting device 30 may also be configured to move along edge 28a about cup 28 in the direction shown by arrow 45. It is shown in FIGS. 1-3 that handle portion 14 may extend from proximal end portion 12a of elongate member 12. Handle portion 14 may include ergonomic and/or geometric structures that may assist a device operator with gripping medical device 10. For example, in some embodiments, handle portion 14 may include finger grips. Handle portion 14 may also include a second actuating mechanism 20. Rotational movement of cutting device 30 may be accomplished via second actuating mechanism 20. Second actuating mechanism 20 may be any actuating mechanism known to one skilled in the art for controlling rotation of cutting device 30. For example, second actuation mechanism 20 may be configured to rotate relative to elongate member 12. Rotation of second actuating mechanism 20 may cause rotation of a rod 48 within elongate member 12. Rod 48 may be attached to second actuating mechanism 20 at one end (e.g., the proximal end) and to a gear mechanism 50, 52 at its other end (e.g., the distal end). Gear mechanism 50, 52 may also be operatively connected to cutting device 30. Accordingly, rotational movement of second actuation mechanism 20 in the directions indicated by arrow 41 may cause rotational movement of cutting device 30 in the directions indicated by arrow 45. Second actuating mechanism 20 may also include a ratcheting detent or locking mechanism to maintain cutting device 30 in a desired orientation or location, if necessary.

Figure 5A:
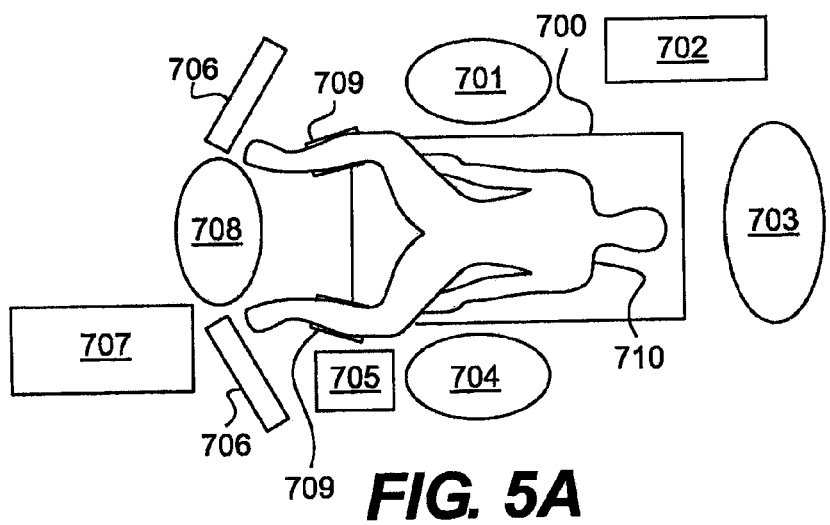
FIG. 5A is a top view of a preoperative patient setup.
Figure 5B:
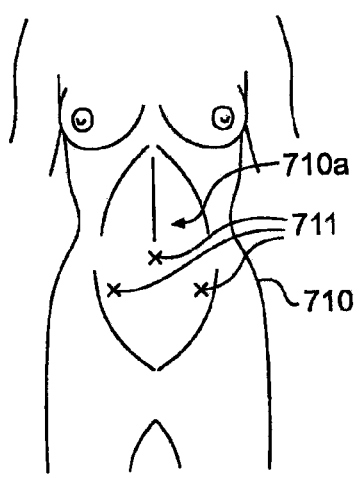
FIG. 5B is an anterior view of a patient being prepared for a laparoscopic hysterectomy procedure.
Figure 5C:
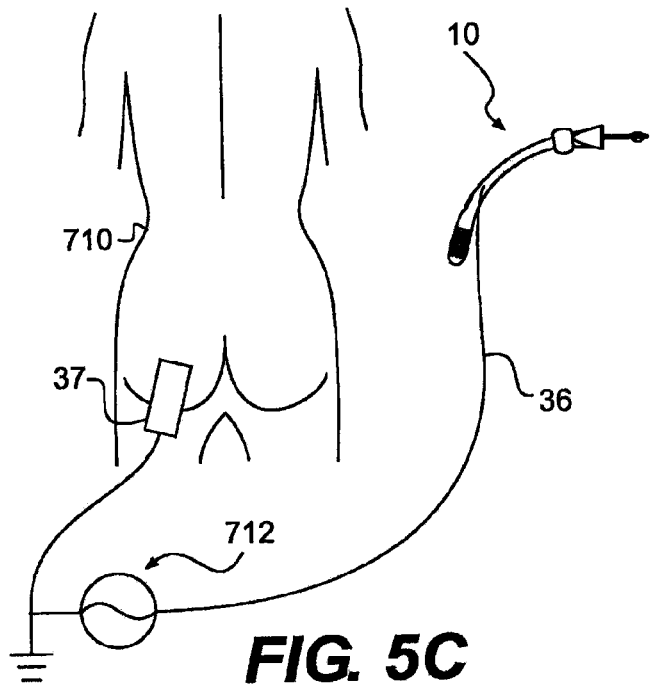
FIG. 5C is a posterior view of a patient being prepared for a laparoscopic hysterectomy procedure.

Cutting device 30 may be any known cutting device, including, but not limited to, cautery blades, radio-frequency (RF) devices, cryoablation catheters, lasers, cautery forceps/scissors, microwave probes, sharpened blades, and/or ultrasonic ablation devices. In one embodiment, cutting device 30 may be an electrocautery device connected through electrical line 36 to an energy source 712 (FIG. 5C) such as, for example, an RF generator. Cutting device 30 may be monopolar, as illustrated in FIG. 5C, or bipolar. In monopolar embodiments, for example, medical device 10 may further include a grounding pad 37 for placement under the patient, as is well known in the art. In bipolar embodiments, cutting device 30 may include two opposing, coacting components that serve to complete the cautery circuit.

In monopolar embodiments, one or more surfaces of cutting device 30 may be coated with a suitable coating. In one embodiment, the coating may be a dielectric coating. The electrical properties of the coating may be chosen to maximize the flow of electrical cutting current flowing from a leading edge of cutting device 30 while minimizing total current flow through the patient. For example, one or more surfaces of cutting device 30 may be coated with a material that increases the electrical resistance to the flow of current from the one or more surfaces of cutting device 30 while other portions (e.g., edges) of cutting device 30 may remain uncoated. Suitable coating materials may include, but are not limited, to rubber, silicone, and plastics such as PTFE.

Figure 4B:
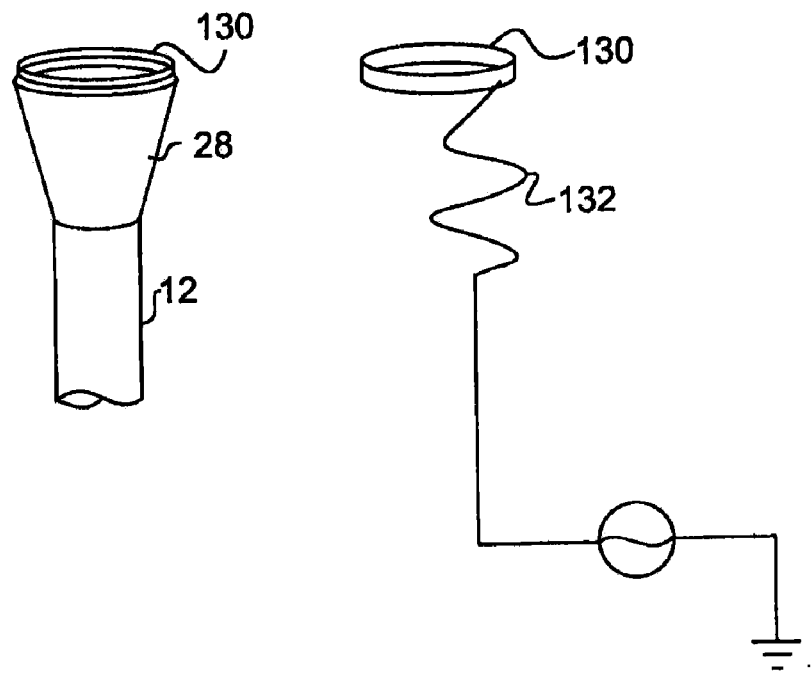
FIG. 4B depicts an alternate embodiment of a cutting device for use with the medical devices disclosed herein.
Figure 4C:
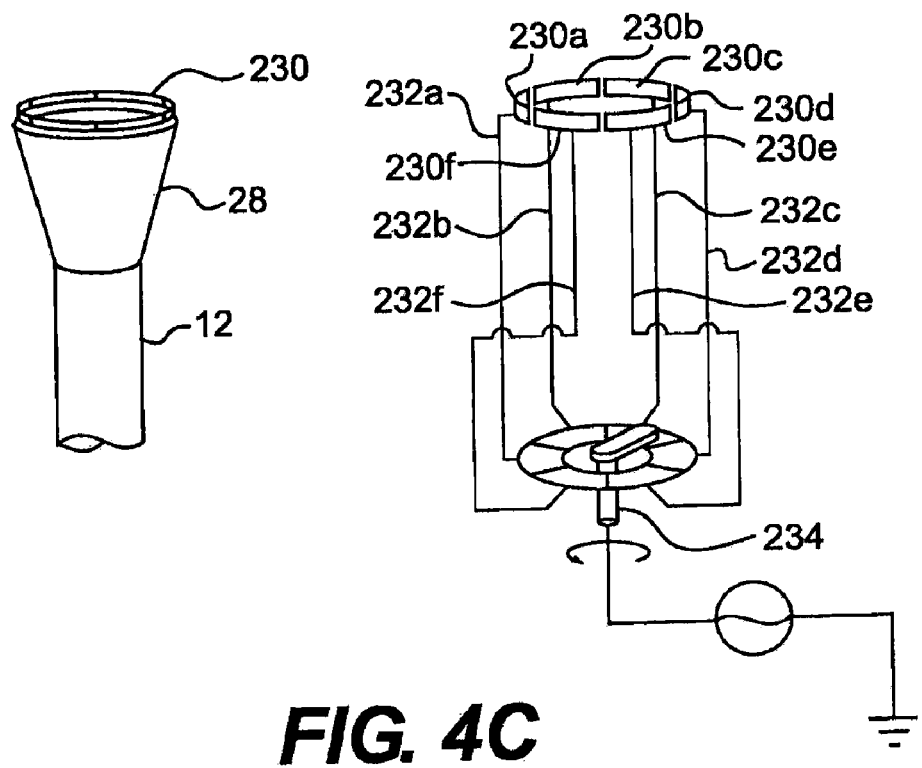
FIG. 4C depicts a further embodiment of a cutting device for use with the medical devices disclosed herein.

FIGS. 4B and 4C illustrate alternative embodiments of cutting device 30. For example, cutting device 30 may be a ring 130 or substantially ring-like 230. The ring may be a single continuous ring 130 that is deployable/retractable as one, unitary portion; or ring 230 may contain multiple segmented sections 230a-f. Segmented sections 230a-f may be formed by overmolding a continuous ring with plastic or other insulating material to form exposed, segmented sections 230a-f. In such embodiments, ring 230 may be connected to an electrode. Alternatively, each segmented section 230a-f may be discrete and attached to individual wires 232a-f through a switch 234 to an electrosurgical generator, such that each segment 230a-f may be deployed independently and/or each segment 230a-f may be selectively turned on, if each segment is deployed at the same time, using switch 234 as a selector. Further, a computer (not shown) may be in communication with segmented sections 230a-f for selectively controlling deployment, rotation, and actuation of each segmented section 230a-f. Accordingly, switch 234 may be a microcontroller capable of executing a software control program.

Manipulation device 24 may be fixed to cup 28 and extend distally from cup 28. In some embodiments, manipulation device 24 may be integral with cup 28. In other embodiments, however, manipulation device 24 may be removably coupled to cup 28. In still other embodiments, manipulation device 24 may be slidably disposed in relation to cup 28. Manipulation device 24 may be a malleable or flexible elongate member made from any suitable biocompatible material known to one of ordinary skill in the art having sufficient flexibility to traverse vaginal and uterine cavities.

Manipulation device 24 may have any desired cross-sectional shape and/or configuration, and may be any desired dimension that can be received within the vaginal and uterine cavities. For example, manipulation device 24 may be a hollow structure with one or more lumens or channels (not shown) providing a passage for surgical equipment. Surgical equipment may include, but is not limited to, optical scopes, illumination devices, and/or tools for irrigation, insufflation, biopsies, vacuum suctioning, closure of the vaginal cuff and/or drug delivery. Manipulation device 24 may further have an atraumatic configuration on its distal end portion and exterior surface. Such exterior configurations may include, but are not limited to, a smoothed, rounded surface. In addition, manipulation device 24 may include any suitable coating, such as an anesthetic, antibacterial, or lubricious coating.

At least one expandable member may be disposed on an exterior surface of medical device 10. In one embodiment, as shown in FIG. 1, first and second expandable members 18, 26 may be disposed on exterior surfaces of elongate member 12 and manipulation device 24, respectively. First expandable member 18 may be an occluder in the form of a vaginal dam in order to prevent passage alongside of medical device 10. For example, during a hysterectomy procedure, the abdomen may be inflated with gas to create space for visualization and uterine movement, and first expandable member 18 may prevent that gas from prematurely escaping during a hysterectomy procedure. Second expandable member 26 may be used to retain medical device 10 in a desired location within a uterine cavity. For example, second expandable member 26 may serve to secure manipulation device 24 relative to a uterus when the uterus is removed transvaginally during a TLH procedure.

The phrase "expandable member" generally relates to any expandable structure, including inflatable structures, mechanically expandable structures, and deformable structures, such as foamed rubbers. In one embodiment, expandable members 18, 26 may be inflatable balloons with any degree of elasticity, so long as they are capable of inflation to a desired dimension to maintain the position of medical device 10 within the vaginal and uterine cavities. Expandable members 18, 26 may be thin-walled structures made of material of low elasticity (which does not stretch significantly during inflation) or highly elastic material (which does stretch significantly during inflation). Expandable members 18, 26 may also be made from polyethylene terephthalate (PET), polyurethanes, polyethylenes and ionomers, copolyesters, rubbers, polyamides, silicone, latex, or any other suitable materials known in the art.

Expandable members 18, 26 may be fluidly connected to fluid sources via expansion lines. For example, first and second expandable members 18, 26 may be connected via first and second expansion lines 32, 34 to fluid sources such as, for example, saline. Fluid source connections may allow for inflation of expandable members 18, 26 from a collapsed configuration to an expanded configuration. Fluid sources may also allow for deflation of expandable members 18, 26 from an expanded configuration to a collapsed configuration. Expandable members 18, 26 may additionally include sensors and indicators to monitor various properties during inflation and deflation, including, but not limited to, safety features, such as a pressure limiting valve and/or a pressure sensor to monitor the force expandable members 18, 26 may exert on a patient's vaginal and uterine cavities. Expandable members 18, 26 may also include radiopaque and/or sonoreflective markers so that one could visualize and monitor the expansion of expandable members 18, 26.

Alternatively, expandable members 18, 26 may be mechanically expandable members, including, but not limited to, cages, foams, and stents. In embodiments with mechanically expandable members 18, 26, expansion lines 32, 34 may be substituted for control lines leading to mechanical actuating and retracting means for selectively expanding and collapsing expandable members 18, 26. For example, mechanical actuating and retracting means may include retractable covers, biodegradable sleeves, motor attachments, or any other suitable actuating means known to those skilled in the art. Mechanical expandable members 18, 26 may also be provided with sensors, indicators, or radiopaque and/or sonoreflective markers to monitor properties during expansion and retraction of expandable members 18, 26 within vaginal and uterine cavities.

Turning now to FIGS. 5A-5C, 6, 7A-7B, 8A-8B, and 9A-9C in the present disclosure, there is illustrated an embodiment of a method for performing a TLH procedure. The patient may be prepared for the surgery according to procedures that are well known in the surgical arts. For example, patient 710 may be oriented in a supine-lithotomy configuration on operating table 700, such that patient 710's legs may rest in raised stirrups 709. Alongside operating table 700, a surgeon 704, an anesthesiologist 703, and a medical assistant 708 may be present. Other suitable personnel 701 may be present as well. Additionally, the operating room may be provided with equipment to assist in the surgery, including, but not limited to, monitors 706, a foot switch 705, an electrosurgical generator 702, and an instrument table 707. The personnel and equipment may be arranged in any desired order and/or configuration.

Once patient 710 is prepared, medical device 10 is inserted into the vaginal and uterine cavities, and the first and second expandable members 18, 26 (FIG. 7B) are expanded to abut tissue in the vaginal and uterine cavities in order to properly position medical device 10 and facilitate occlusion in the vaginal cavity. The abdominal cavity 710a may then be insufflated to create space and facilitate accessibility and visibility of the female pelvic organs. Multiple laparoscopic incisions 711 may further be cut in the patient's abdomen area to facilitate the introduction of surgical instruments. As shown in FIG. 5C, prior to insertion of medical device 10, cutting device 30 may be connected through an electrical line 36 to an energy source 712 such as, for example, a radio-frequency (RF) or electrosurgical generator.

Figure 6:
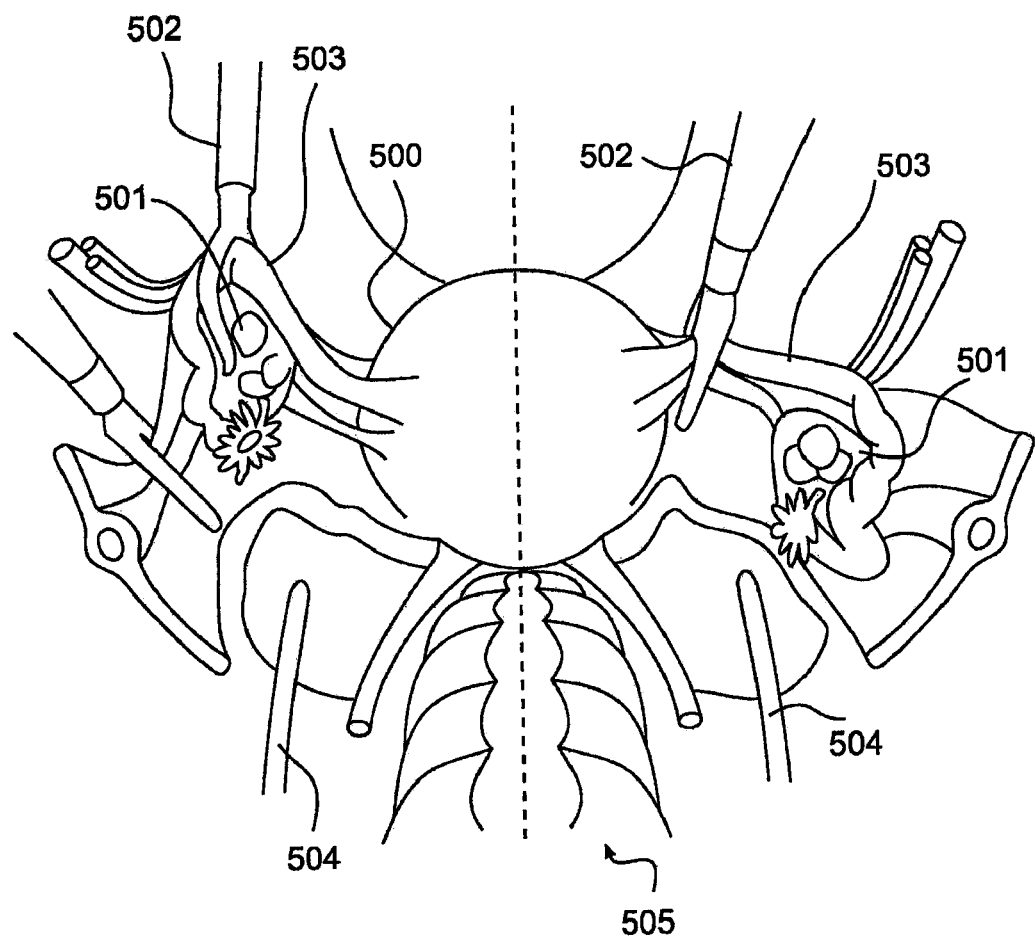
FIG. 6 is an internal view of a body portion undergoing a step of cutting ligamentus structures in a laparoscopic hysterectomy procedure.
Figure 7A:
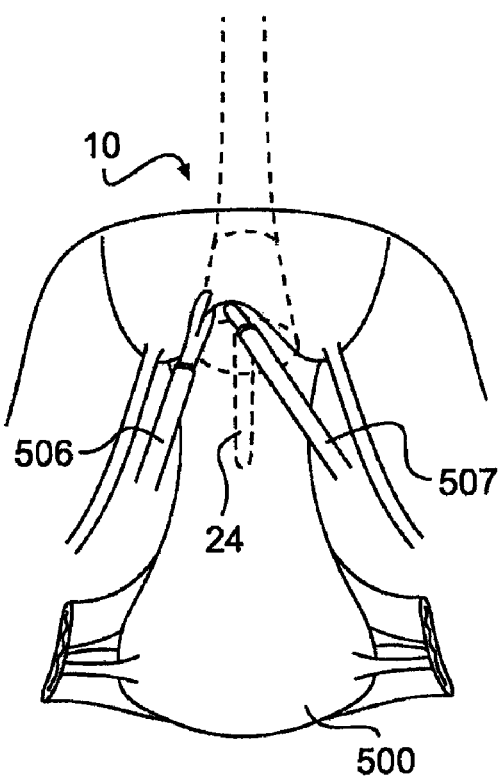
FIG. 7A is an internal view of a body portion showing laparoscopic tools in conjunction with the medical device of FIG. 1 inserted into a vaginal cavity for performing a TLH procedure.
Figure 7B:
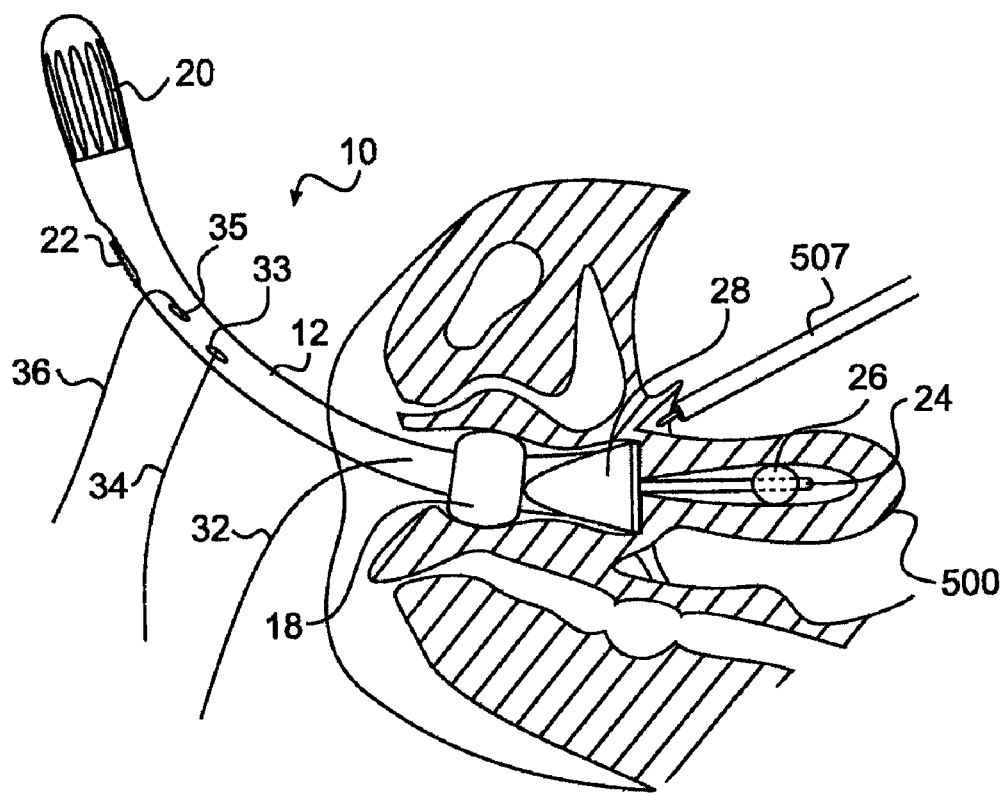
FIG. 7B is a cross-sectional view of the body portion of FIG. 7A showing a laparoscopic tool in conjunction with the medical device of FIG. 1 inserted into a vaginal cavity for performing a TLH procedure.

Turning now to FIGS. 6 and 7A-7B, surgical instruments 502, 506, 507 may be inserted through incisions 711 in order to, for example, facilitate cutting of ligamentus structures 503 and/or to illuminate/visualize areas of interest. In some embodiments, medical device 10 may be inserted into a vaginal cavity and advanced to uterus 500 after surgical instruments 502, 506, 507 have been inserted into the patient 710, or one or more preparation steps have been completed. Further, manipulation device 24 of medical 10 may be positioned to extend into the uterine cavity. Once end effector assembly 16 of medical device 10 has been inserted into the vaginal and uterine cavities, expandable members 18, 26 may be expanded from a collapsed configuration to an expanded configuration via expansion lines 32, 34, or any other means discussed in the present disclosure.

Figure 8A:
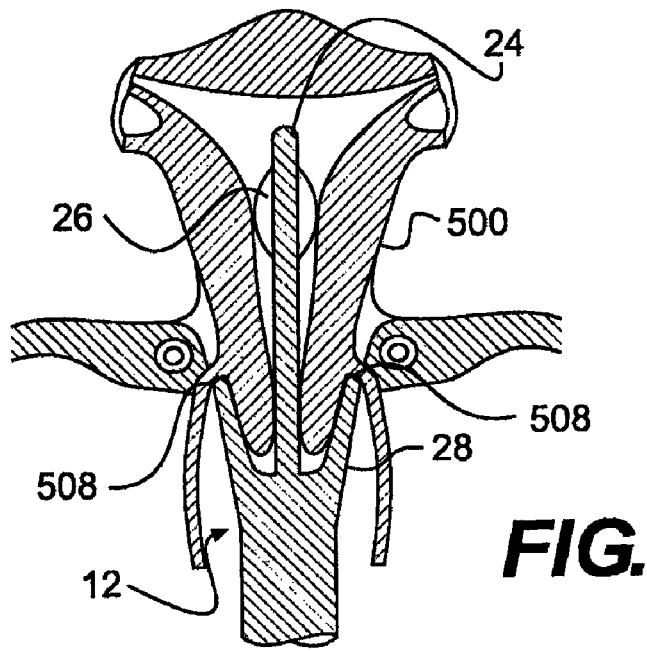
FIG. 8A is a cross-sectional view of a body portion showing a cup of the distal end of the medical device of FIG. 1 engaging vaginal fornices of a patient.
Figure 8B:
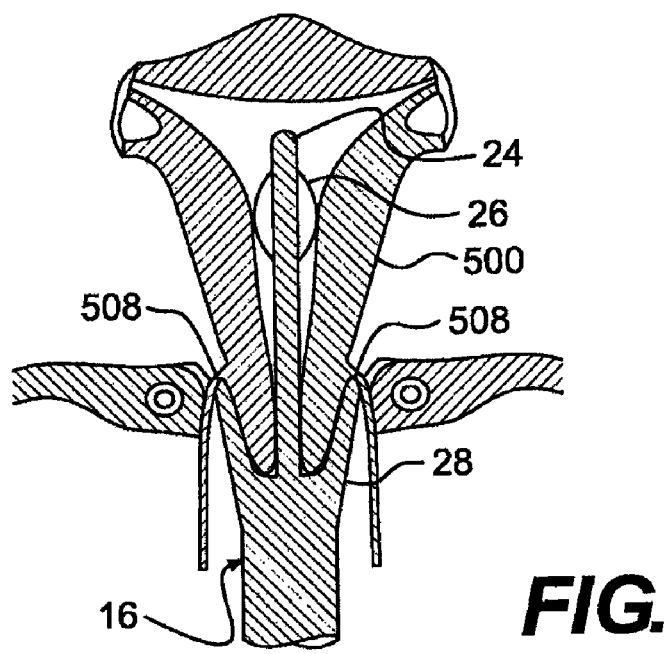
FIG. 8B is a cross-sectional view of a body portion showing the colpotomy cup inserted and extending into an apex of the vaginal fornices following a cephalad push.
Figure 8B:
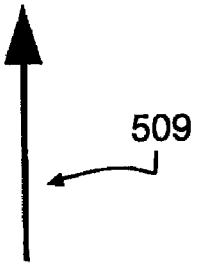

Manipulation device 24 may be at least partially positioned within the uterus 500, and cup 28 may engage vaginal fornices 508, as shown in FIG. 8A, FIG. 8B illustrates that a device operator may then apply a cephalad force to medical device 10 in the direction of arrow 509, allowing cup 28 to tent vaginal fornices 508, thereby preparing uterus 500 for cutting/excision.

Figure 9A:
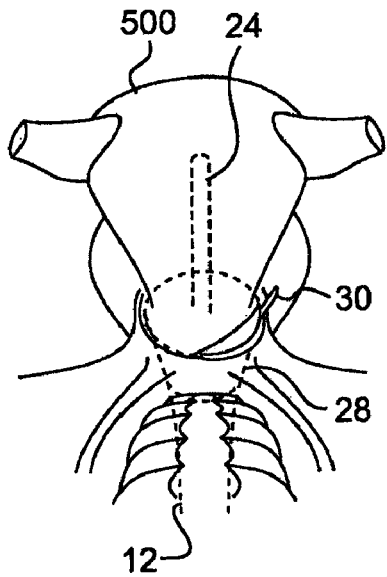
FIGS. 9A-9C are sectional views of a body portion showing the cutting device of FIG. 4A excising the uterine cervix from the vagina during a TLH procedure.
Figure 9B:
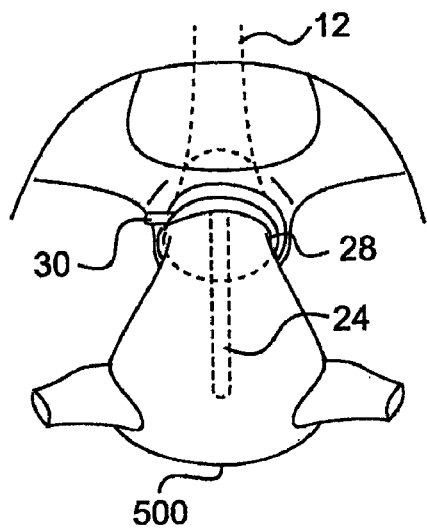
Figure 9C:
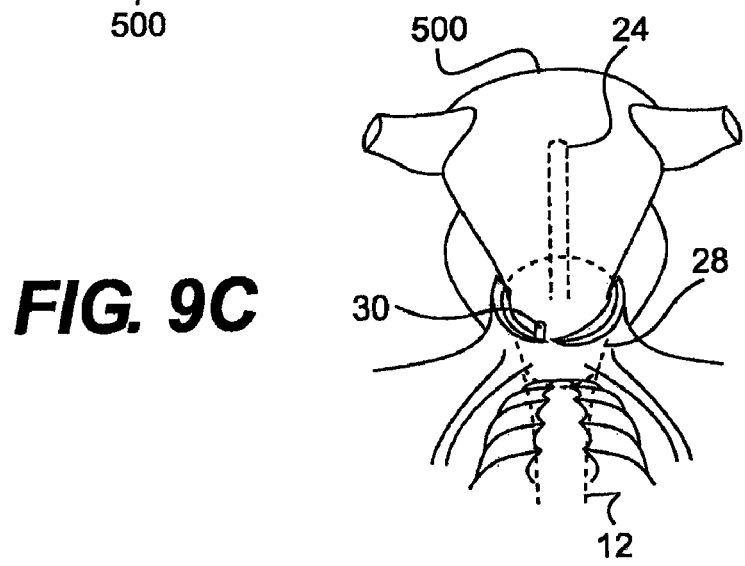

As illustrated in FIGS. 9A-9C, a device operator may then actuate first actuating mechanism 22 in the direction of arrow 39 to advance cutting device 30 from a retracted position to a deployed position, which may create an incision in vaginal fornix tissue. Second actuating mechanism 20 may be rotated along the direction of arrow 41 relative to elongate member 12 to move cutting device 30 along edge 28a of cup 28. In this manner, cutting device 30 may create a substantially rounded, uniform colpotomy incision to separate uterus 500, along with the cervix, from the vaginal apex. Upon completion of uterine and cervical excision, the vaginal cuff opening left behind may be closed using means known to those skilled in the art, including, but not limited to, sutures, staples, and/or glue. Additionally, uterus 500 may be removed by any suitable means known in the art. In some embodiments, additional tools and/or equipment may be used to, for example, cut uterine tissue into small pieces for extraction. One example of such a tool may include a morcellator. In addition, or alternatively, a suctioning device may be used to remove the entire uterus or any of its portions.

Figure 10:
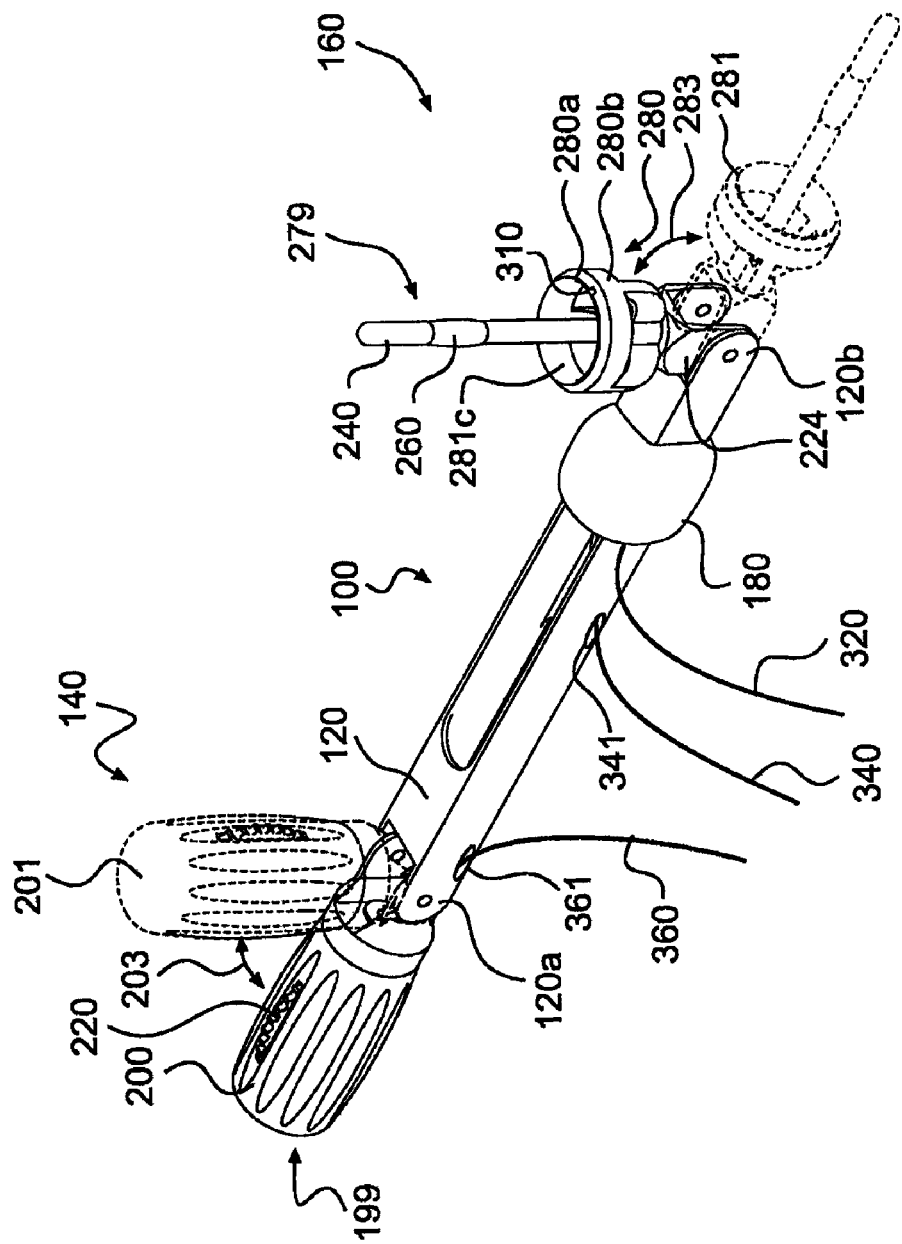
FIG. 10 is a perspective view of a medical device for use in performing a TLH procedure, according to a second embodiment of the present disclosure.

FIG. 10 illustrates a further embodiment of a medical device 100 for performing a TLH procedure. Medical device 100 may include one or more features of medical device 10 of FIG. 1. For example, medical device 100 may include an elongate member 120, an end effector assembly 160, a handle portion 140, and expandable members 180, 260. Substantively, elongate member 120 may be similar to elongate member 12 of FIG. 1.

End effector assembly 160 may be pivotally secured to distal end 120b of elongate member 120, such that it may pivot between a first position 279 and a second position 281 along a first pivotal path 283. Additionally, handle portion 140 may be pivotally secured to a proximal end 120a of elongate member 120, such that it may pivot between a first position 199 and a second position 201 along a second pivotal path 203. Movement of end effector assembly 160 between its first and second positions 279, 281 may be controlled by movement of handle portion 140. Additionally, end effector assembly 160 and handle portion 140 may each be secured to elongate member 120 via any type of pivot mechanism known to those skilled in the art. For example, in one embodiment, end effector assembly 160 and handle portion 140 may each be secured to elongate member 120 via a hinge 224, which may include a pivot pin.

End effector assembly 160 may be a separately connected portion to elongate member 120 and may be reusable or disposable. End effector assembly 160 may also be produced in a variety of dimensions to accommodate a variety of patient anatomies.

End effector assembly 160 may include multiple components, including, but not limited to, a cup 280, a manipulation device 240, and a cutting device 330. Manipulation device 240 may be substantively similar to manipulation device 24 of FIG. 1. However, manipulation device 240 may be configured to rotate relative to elongate member 120, as shown in FIG. 10. Cup 280 may include one of more of the features of cup 28 of FIG. 1. For example, cup 280 may have an enlarged edge 280a that is atraumatic and/or textured to aid in gripping a cervix to maintain desired placement of medical device 100. Cup 280 may also have an atraumatic exterior surface 280b with a coating affixed thereto. Cup 280 may also be configured to rotate relative to elongate member 120.

Figure 12A:
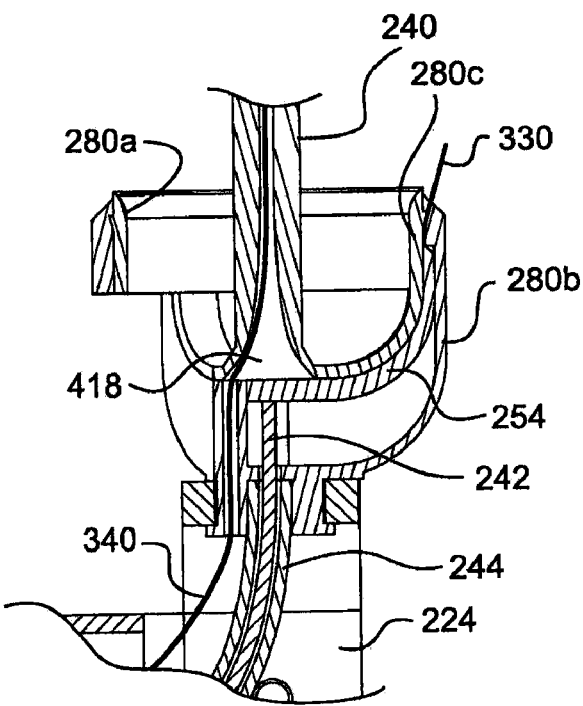
FIGS. 12A-12B are cross-sectional views of a cup of the medical device of FIG. 10 with a cutting device in deployed and retracted configurations, respectively.
Figure 12B:
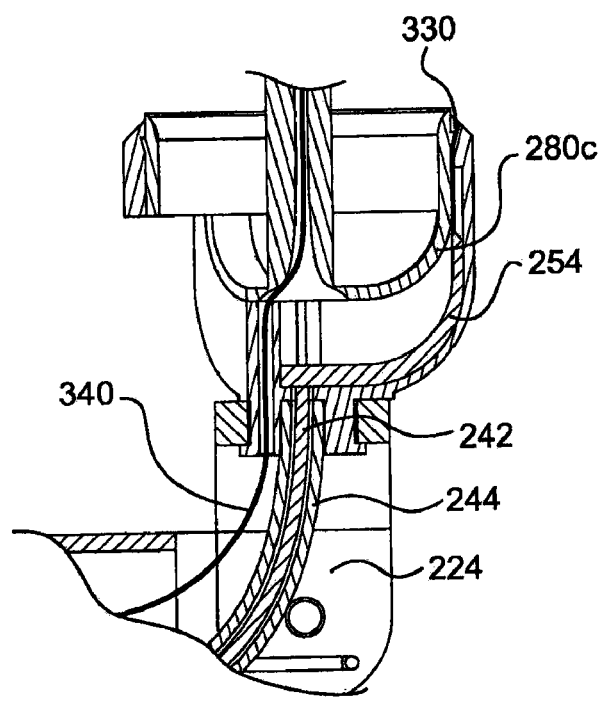

Cup 280 may have any shape and/or configuration, and may be any desired dimension such that it can be received in a patient's vaginal cavity. FIGS. 12A and 12B illustrate that cup 280 may include an inner cup portion 280c and an outer cup portion 280b. Inner cup portion 280c may have a bottom surface that is spaced from a lower surface of outer cup portion 280b. Inner and outer cup portions 280c, 280b may include through-openings in outer surfaces of each portion. Alternatively, inner and outer cup portions 280c, 280b may be solid pieces with no through-openings.

Cup 280 may also include a cutting device 330 located in recess 310 (FIG. 10) and a cutting device carrier 254 located in a space between an outer, bottom surface of inner cup portion 280c and an inner surface of outer cup portion 280b. A control rod 242 may be connected to cutting device carrier 254 and to a first actuating mechanism 220 within handle portion 140. First actuating mechanism 220 may be any actuating mechanism capable of creating axial motion. Such actuating mechanisms may include, but are not limited to, a slide actuator or push button. In one embodiment, first actuating mechanism 220 may be a thumbwheel. Rotation of thumbwheel 220 may cause cutting device carrier 254 to move within the space between inner cup portion 280c and outer cup portion 280b, thereby causing movement of cutting device 330 between retracted and deployed configurations in the directions shown by arrow 335, as shown in FIGS. 11 and 12A-12B.

Figure 11:
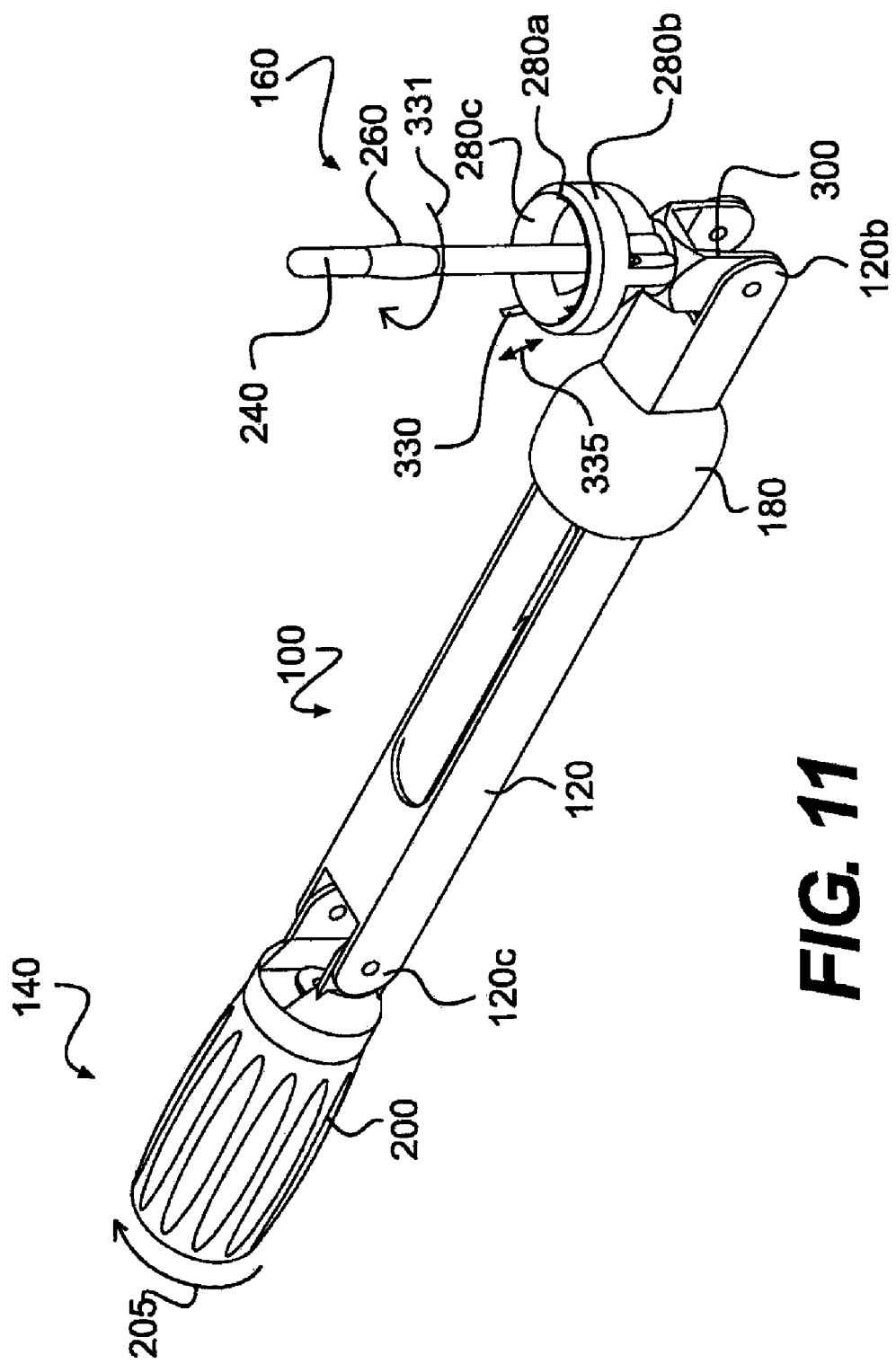
FIG. 11 is a perspective view of the medical device of FIG. 10 showing rotated configurations of its proximal and distal ends, and with a cutting device in a deployed configuration.

With reference to FIG. 11, cutting device 330 may also be configured to rotate about cup 280 in the direction of arrow 331 due to operation of second actuating mechanism 200. Second actuating mechanism 200 may be any actuating mechanism known to one skilled in the art that provides rotation of cutting device 330. For example, second actuating mechanism 200 may be configured to rotate relative to elongate member 120 in the direction of arrow 205. Control rods 242, 244 may be connected to second actuating mechanism 200 such that rotation of second actuating mechanism 200 may cause control rods 242, 244 to transfer rotational force to cutting device 330. Alternatively, second actuating mechanism 200 may be configured to transfer rotational force to cup 280, such that cup 280 and cutting device 330 rotate together.

Each of first and second actuating mechanisms 220, 200 may also comprise a ratcheting detent or a locking mechanism to maintain cutting device 330 in any desired orientation.

Cutting device 330 may include one or more of the features of cutting device 30 of FIG. 1. For example, cutting device 330 may be any cutting device known to those skilled in the art, including an electrocautery device connected through an electrical line 360 to an energy source (e.g., an electrosurgical generator). Electrical line 360 may be connected to cutting device 330 via an exterior opening 361. Cutting device 330 may also comprise one of the ring-shaped configurations 130, 230 illustrated in FIGS. 4B and 4C. In one embodiment, cutting device 330 may be made of a flexible material such that it may project out to a desired cutting angle when deployed, as illustrated in FIGS. 12A and 12B. The desired cutting angle may be formed between an inner surface of outer cup portion 280b and an outer surface of inner cup portion 280c. In one embodiment, the desired cutting angle may be between approximately 10 and 45 degrees and preferably approximately 15 degrees; however, the cutting angle may be any value that accomplishes a TLH procedure.

As shown in FIG. 11, medical device 100 may also include at least one expandable member on elongate member 120 and/or manipulation device 240. Expandable members 180, 260 may be substantively similar to expandable members 18, 26 of FIG. 1. For example, first and second expandable members 180, 260 may be connected to first and second expansion source lines 320, 340. First and second expansion source lines 320, 340 may be connected to a lumen or channel (not shown) in medical device 100 via exterior openings 341.

Figure 13:
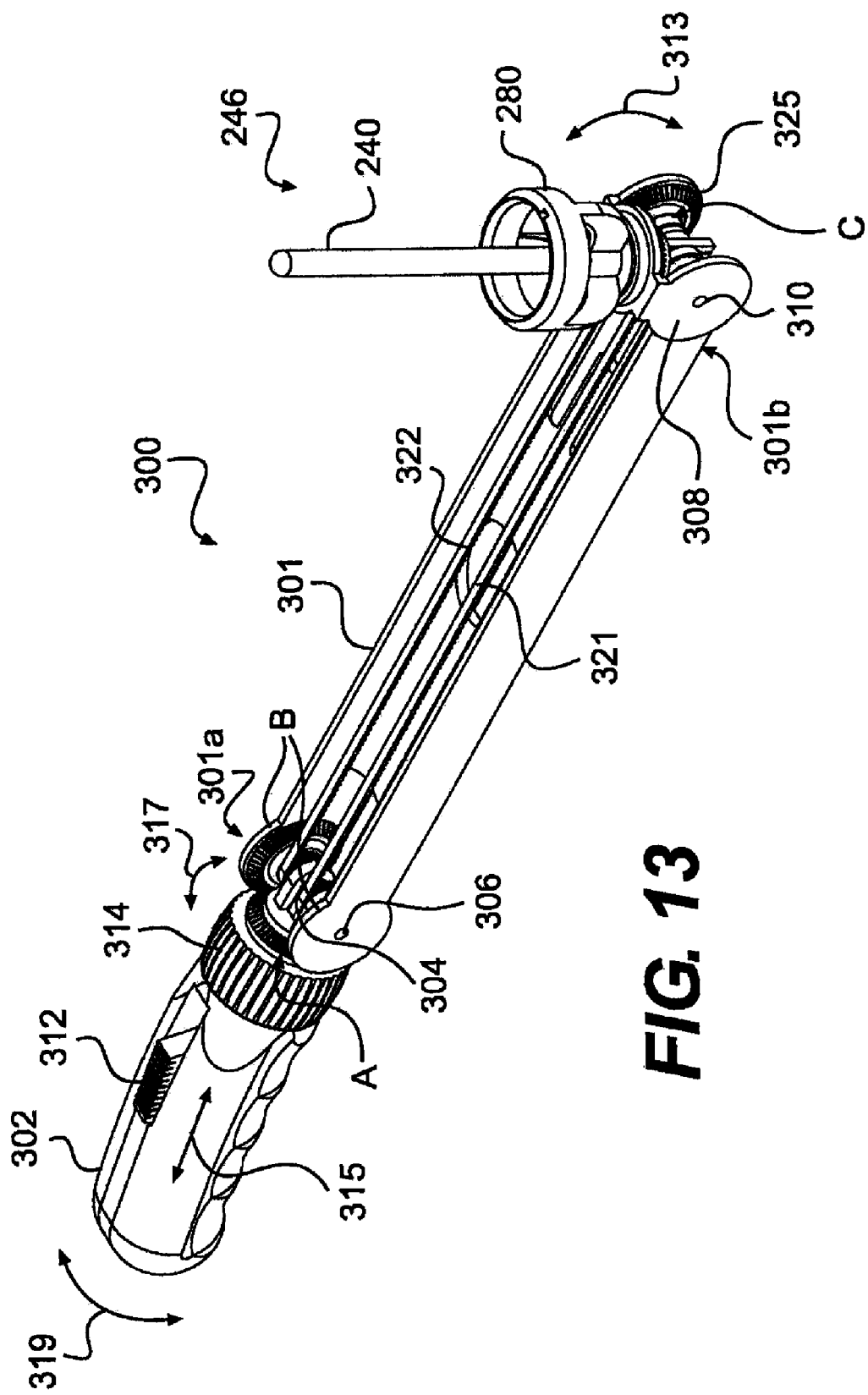
FIG. 13 is a perspective view of a medical device for use in performing a TLH procedure, according to a third embodiment of the present disclosure.

FIG. 13 illustrates another embodiment of medical device 300 for performing TLH procedures. Medical device 300 may include one or more features of medical device 100 in FIG. 10. For example, medical device 300 may include the same features of cup 280 and manipulation device 240 as illustrated in medical device 100 shown in FIG. 10.

Medical device 300 may also include an elongate member 301, an end effector assembly 246, and a handle portion 302. Elongate member 301 may include one or more features of elongate member 120 in FIG. 10. In addition, or alternatively, elongate member 301 may be a hollow structure including a mechanical system of gears and belts as an alternative to the control rod 242 system discussed above. Gears and belts may include, but are not limited to, slot gears 325, toothed gears 304, and toothed belts 321, 322. Handle portion 302 may be pivotally secured to elongate member 301 at its proximal end 301a. Handle portion 302 may be rotated about a pivot rod 306 in the direction shown by arrow 319. End effector assembly 246 may be pivotally secured to elongate member 301 at its distal end 301b via pivot rod 310. Movement of handle portion 302 in the direction of arrow 319 may cause movement of end effector assembly 246 in the direction of arrow 313.

Further, movement of a first actuating mechanism 312 in the direction of arrow 315 may cause deployment of cutting device 330 via a series of independent translational and rotational movements. Translational movement of first actuating mechanism 312 may cause rotational movement of gears A and C and one of toothed belts 321, 322. Rotational movement of gears A and C and one of toothed belts 321, 322 may then cause translational movement in end effector assembly 246, resulting in deployment of cutting device 330. Similarly, rotational movement of second actuating mechanism 314 in the direction shown by arrow 317 may cause rotation of cutting device 330 via a series of independent rotational movements.

Figure 14A:
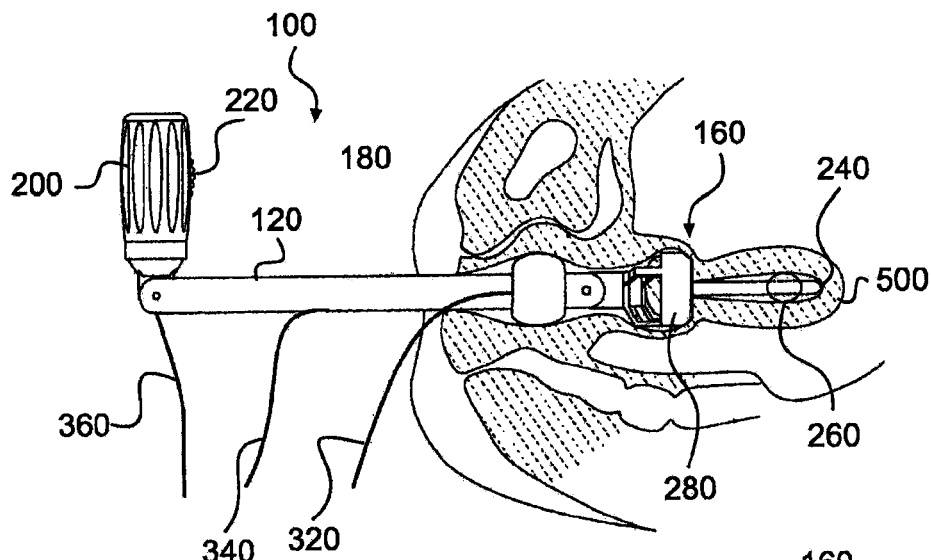
FIG. 14A is a cross-sectional view of a body portion showing the medical device of FIG. 10 inserted into a vaginal cavity for performing a TLH procedure.
Figure 14B:
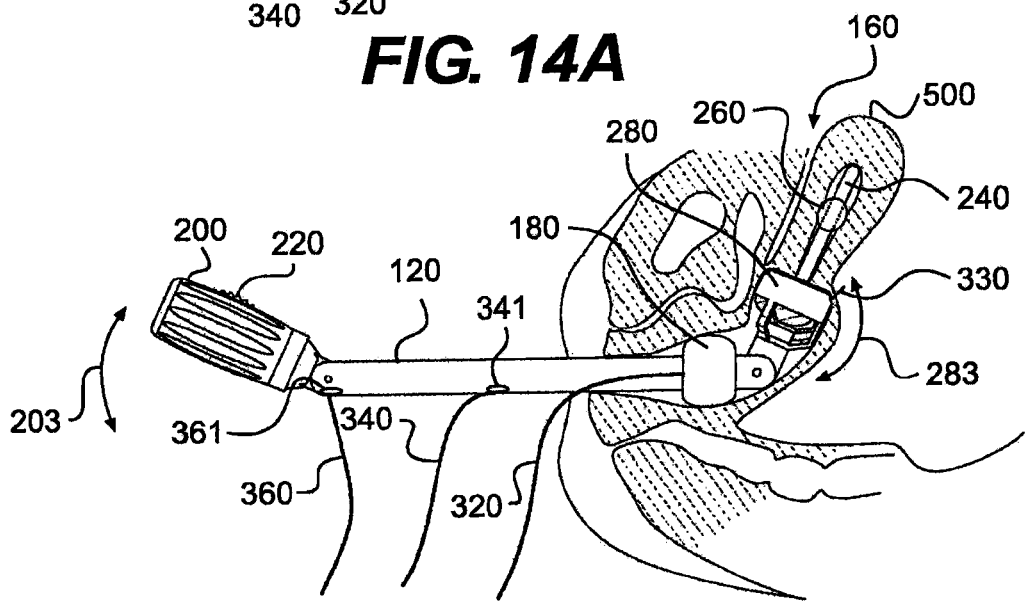
FIG. 14B is a cross-sectional view of a body portion showing the medical device of FIG. 10 inserted into a vaginal cavity and manipulating a position of a uterus for performing a TLH procedure.

FIGS. 14A and 14B of the present disclosure illustrate an embodiment of a method for performing a TLH procedure using medical device 100 of FIG. 10. Alternatively, medical device 300 of FIG. 13 may be used for the TLH procedure in place of medical device 100 of FIG. 10. The method illustrated in FIGS. 14A and 14B follows the same preparation steps as the method illustrated in FIGS. 5A-5C, 6, and 7A-7B. After expandable members 180, 260 have been expanded such that they abut tissue in the vaginal and uterine cavities, a device operator may rotate handle portion 140 in the directions of arrow 203. Rotation of handle portion 140 may cause manipulation device 240 to move uterus 500 in the cephalad directions shown by arrow 283 and may cause cup 280 to tent vaginal fornices 508, placing uterus 500 in a desired excisional orientation. Cutting device 330 may then be deployed and rotated via the use of first and second actuating mechanisms 220, 200 in order to create a uniform, rounded colpotomy incision to separate uterus 500, along with the cervix, from the vaginal apex. Upon completion of uterine and cervical excision, the vaginal cuff opening left behind may be sutured or otherwise closed as known to those skilled in the art.

Figure 15:
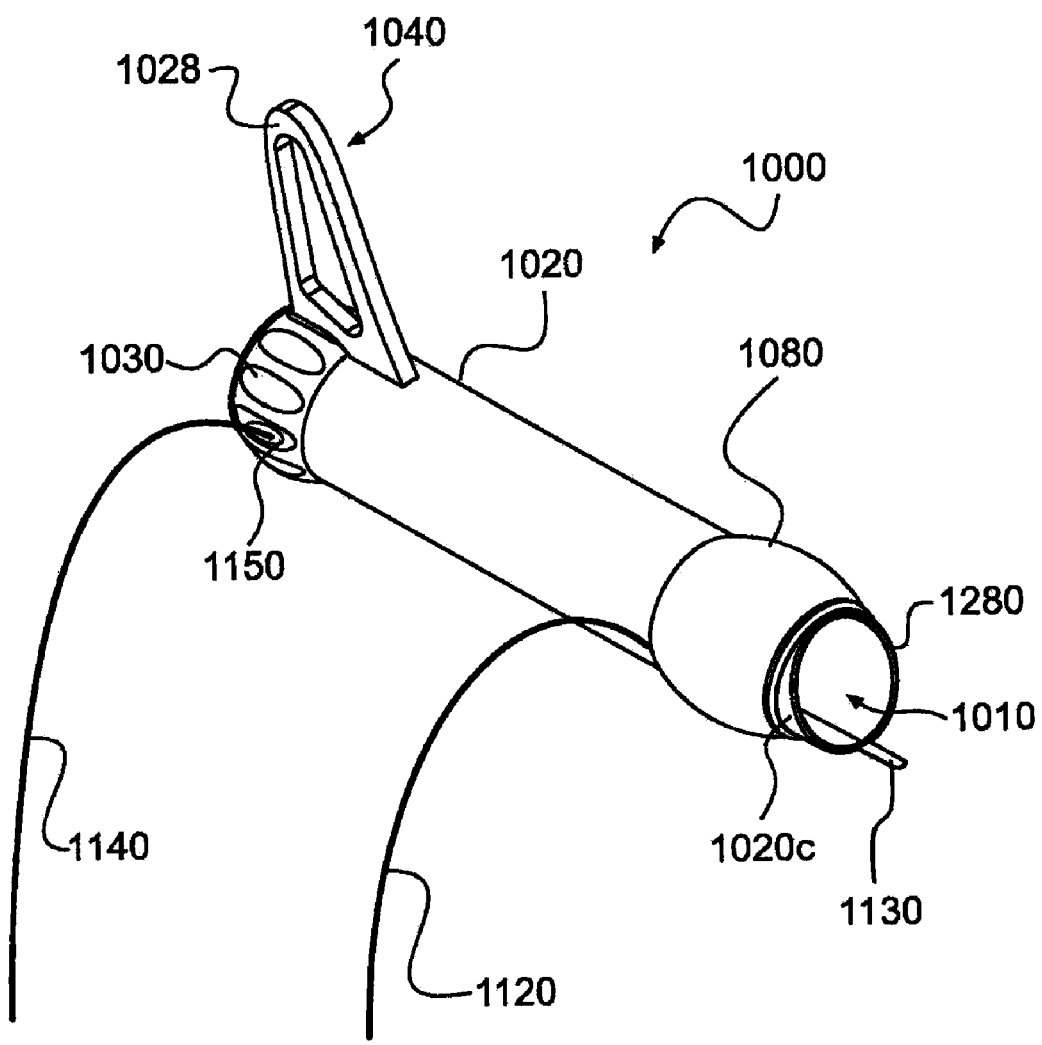
FIG. 15 is a perspective view of a medical device for use in performing a TLH procedure, according to a fourth embodiment of the present disclosure.
Figure 16:
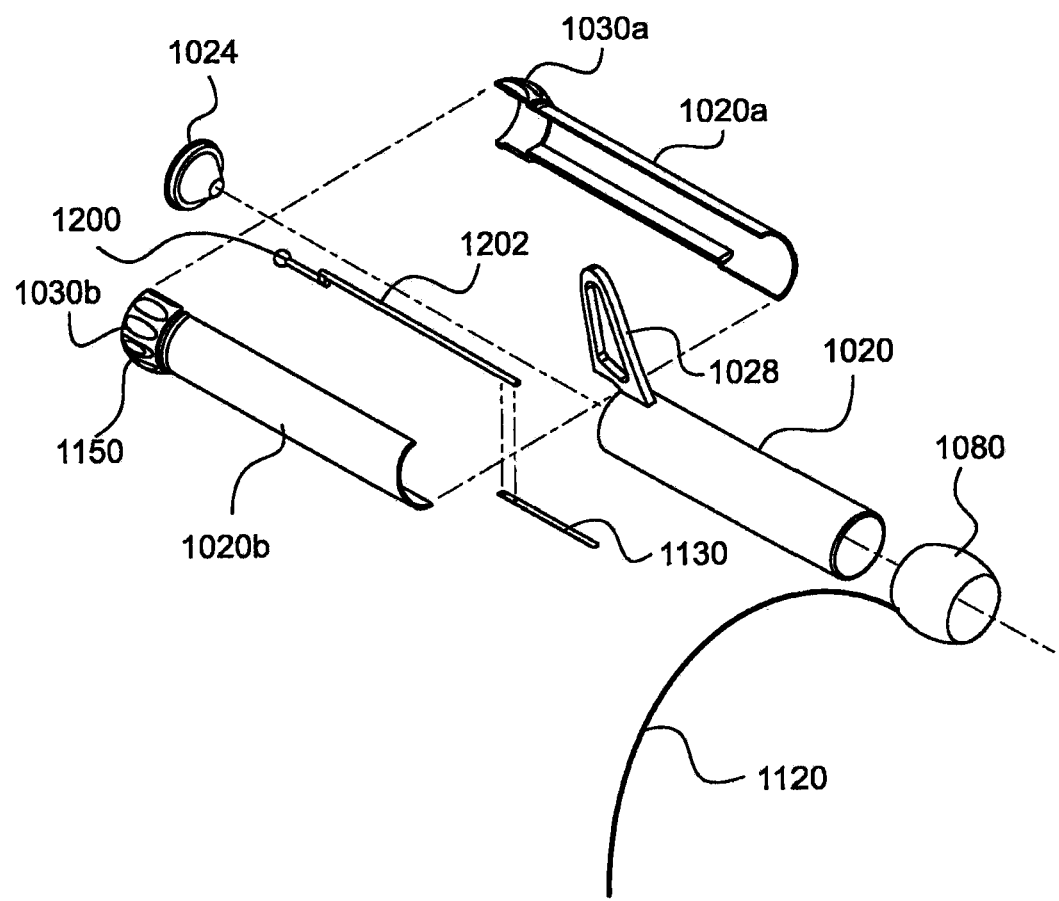
FIG. 16 is an exploded view of the medical device of FIG. 15.

FIG. 15 illustrates another medical device 1000 for performing a TLH procedure, in accordance with a fourth embodiment of the present disclosure. Medical device 1000 may include one or more of the features of any of the other embodiments disclosed herein. For example, medical device 1000 may include a first elongate member 1020 and a second elongate member (collectively referred to as "1020a-b") disposed therein. The second elongate member 1020a-b may include two halves 1020a, 1020b. First and second elongate members 1020, 1020a-b may be hollow, tubular structures and may have any cross-sectional shape and desired dimension, so long as they may be received in a vaginal canal. First elongate member 1020 may be a unitary structure. The second elongate member 1020a-b may also be a unitary structure. Alternatively, as noted above, the second elongate member 1020a-b may include two halves 1020a, 1020b, as shown in FIG. 16. Halves 1020a, 1020b may be connected via welding, soldering, or any other connection means known to those skilled in the art. Elongate members 1020, 1020a-b may also include an atraumatic exterior surface with an affixed coating like the exterior surface of elongate member 12 in FIG. 1. Second elongate member 1020a-b may be coaxially disposed within a central lumen of first elongate member 1020. In some embodiments, second elongate member 1020a-b may be rotationally and/or axially movable within first elongate member 1020.

First and second elongate members 1020, 1020a-b may also include one or more lumens or channels 1010, respectively, with the lumens potentially providing passage for a variety of surgical equipment. In one embodiment, medical device 1000 may include an opening 1150 in an exterior surface. Opening 1150 may be in communication with central lumen or channel 1010 for receiving an electrical line 1140 to power a cutting device 1130. Although the depicted embodiment illustrates opening 1150 disposed on control member 1030, opening 1150 may be disposed on any suitable external surface of elongate member 1020. Medical device 1000 may further include a cover 1024 at a proximal end of first and second elongate members 1020, 1020a-b such that cover 1024 may act as a seal. Cover 1024 may also include an opening therethrough, facilitating insertion of surgical equipment through the one or more lumens or channels 1010 in medical device 1000.

Second elongate member 1020a-b may include an atraumatic distal end 1280, which may further comprise suitable geometric configurations to aid in maintaining medical device 1000 in a desired location within a patient. In one embodiment, distal end 1280 may be tapered to provide an angled cutting plane. Medical device 1000 may also include at least one expandable member 1080 along with an expansion source line 1120 connected to expandable member 1080. Although the depicted embodiment illustrates expandable member 1080 being closer to distal end 1280, expandable member 1080 may be positioned anywhere along the length of medical device 1000.

A cutting device 1130 may be disposed within medical device 1000 between halves 1020a, 1020b of second elongate member 1020a-b. In one embodiment, cutting device 1130 may be movable between a retracted position and a deployed position, in which cutting device 1130 extends distally beyond distal end 1280 of second elongate member 1020a-b. Although the depicted embodiment illustrates cutting device 1130 extending straight out of medical device 1000, cutting device 1130 may extend at any suitable angle. Cutting device 1130 may be operatively connected to a first control rod 1200, which may extend to a proximal end of medical device 1000. As shown in FIG. 16, for example, first control rod 1200 may be connected to cutting device 1130 by a second control rod 1202. First and second control rods 1200, 1202 may be separate rods or a unitary piece, such that first control rod 1200 may be offset from second control rod 1202.

Medical device 1000 may further include a handle portion 1040, including, but not limited to, a gripping member 1028 and a control member 1030. Additionally, first control rod 1200 may extend proximally from handle portion 1040. In use, a device operator may maintain first elongate member 1020 and handle portion 1040 in a fixed position when positioning medical device 1000 against a patient's vaginal fornices 508. The device operator may manipulate first control rod 1200 to move cutting device 1130 axially along an axis that is parallel to a longitudinal axis of medical device 1000. The device operator may then rotate control member 1030, which may cause cutting device 1130 to rotate in the same direction as control member 1030.

Figure 17A:
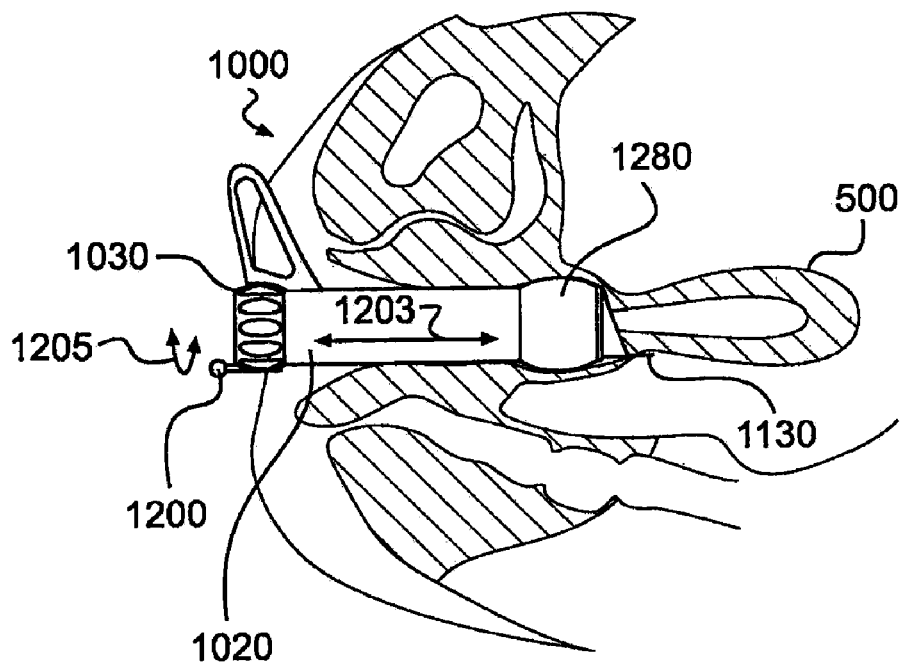
FIGS. 17A-17B are cross-sectional views of a body portion showing the medical device of FIG. 15 with a deployed cutting device separating the uterus during a TLH procedure.
Figure 17B:
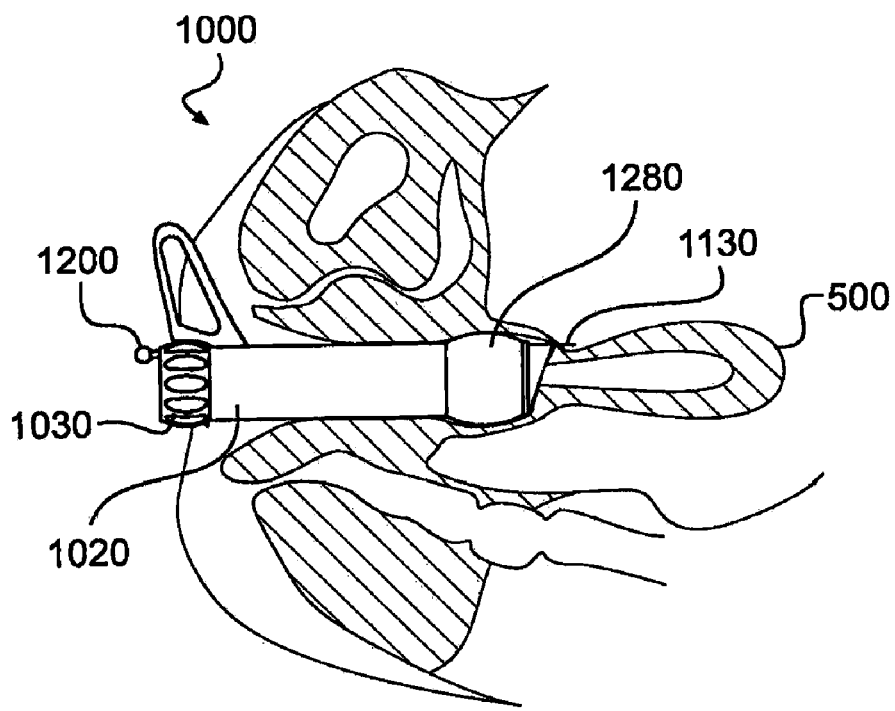

FIGS. 17A and 17B of the present disclosure illustrate a method for performing a TLH procedure using medical device 1000 shown in FIG. 15. The method illustrated in FIGS. 17A and 17B follows the same preparation steps as the method illustrated in FIGS. 5A-5C, 6, and 7A-7B. After insertion of medical device 1000 into a vaginal cavity, distal end 1280 of medical device 1000 may engage one or more vaginal fornices 508. Surgical equipment may also be inserted through a central lumen 1010 of medical device 1000 to aid in the procedure. In one embodiment, expandable member 1080 may be expanded such that it abuts tissue in a vaginal cavity and acts as an occluder, so as to prevent inflation gases from prematurely escaping from the patient's abdomen. Second control rod 1202 and cutting device 1130 are located between halves 1020a, 1020b of second elongate member 1020a-b, which further fit within first elongate member 1020. As previously discussed, a device operator may extend cutting device 1130 by sliding first control rod 1200 in the directions of arrow 1203. Upon deployment of cutting device 1130, the device operator may then rotate the cutting device 1130 by rotating control member 1030 in the directions of arrow 1205 relative to first elongate member 1020 and gripping member 1028 in order to create a uniform, rounded incision to excise the uterus 500, along with the cervix, from the vaginal apex. Upon completion of uterine and cervical excision, the vaginal cuff opening left behind may then be sutured or otherwise closed as known to those skilled in the art.

Figure 18:
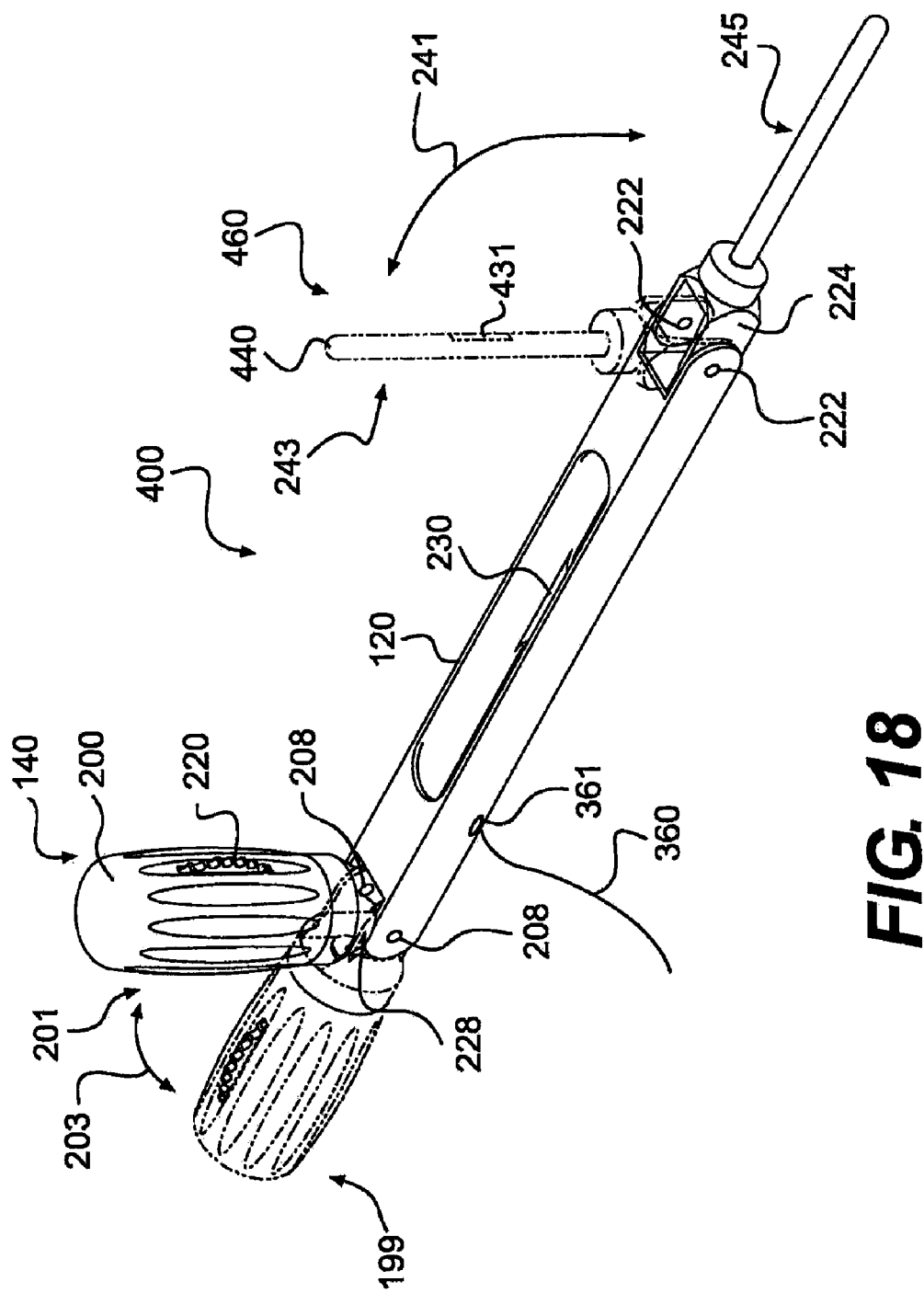
FIG. 18 is a perspective view of a medical device for use in performing a laparoscopic supracervical hysterectomy (LSH) procedure, according to a fifth embodiment of the present disclosure.

FIG. 18 illustrates a medical device 400 for a laparoscopic supracervical hysterectomy (LSH) procedure, in accordance with a fifth embodiment of the present disclosure. Medical device 400 may include one or more of the features of medical device 100 illustrated in FIG. 10. For example, medical device 400 may include an elongate member 120 and a handle portion 140. Medical device 400 may also include an end effector assembly 460. End effector assembly 460 may be capable of pivoting between a first position 243 and a second position 245 in the directions of arrow 241 in response to pivotal motion of handle portion 140 between its first pivotal position 199 and second pivotal position 201 in the directions of arrow 203.

End effector assembly 460 may include a manipulation device 440 with a cutting device 430 located therein. Cutting device 430 may include one or more of the features of cutting device 130 described in FIG. 10. Cutting device 430 may be any cutting device known to those skilled in the art and may be configured to move relative to manipulation device 440 between a deployed position, illustrated in FIG. 19, and a retracted position, illustrated in FIG. 18, in the directions of arrow 209. In its retracted position (FIG. 20), cutting device 430 may be maintained within a recess 431 in manipulation device 440. Recess 431 may be any suitable shape, size, and/or configuration, so long as it may maintain cutting device 430 therein. For example, in one embodiment, recess 431 may be rectangular. Further, manipulation device 440 may include multiple recesses 431, with each recess 431 maintaining a cutting device 430 therein.

Figure 20:
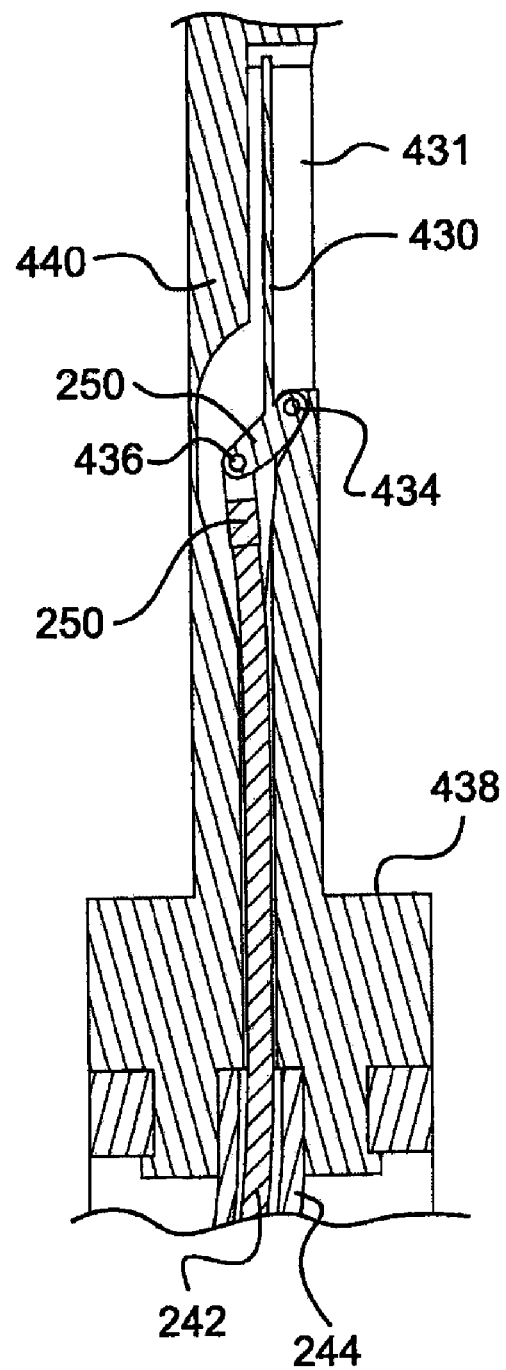
FIG. 20 is a cross-sectional view of a distal end of the medical device of FIG. 18 showing a cutting device in a retracted configuration.

Deployment and retraction of cutting device 430 may be controlled by a first actuating mechanism 220 that may transfer force to cutting device 430 via a control rod 242 and a hinge mechanism 250, as illustrated in FIG. 20. First actuating mechanism 220 and control rod 242 may substantively include the features of first actuating mechanism 220 and control rod 242 of medical device 100 shown in FIG. 10. Hinge mechanism 250 may be any type of pivoting mechanism known to those skilled in the art. Hinge mechanism 250 may also be operably connected to cutting device 430 and may include multiple pivot points 434, 436 within recess 431. Pivoting movement of hinge mechanism 250 about pivot points 434, 436 may cause cutting device 430 to move between its deployed and retracted configurations.

Figure 19:
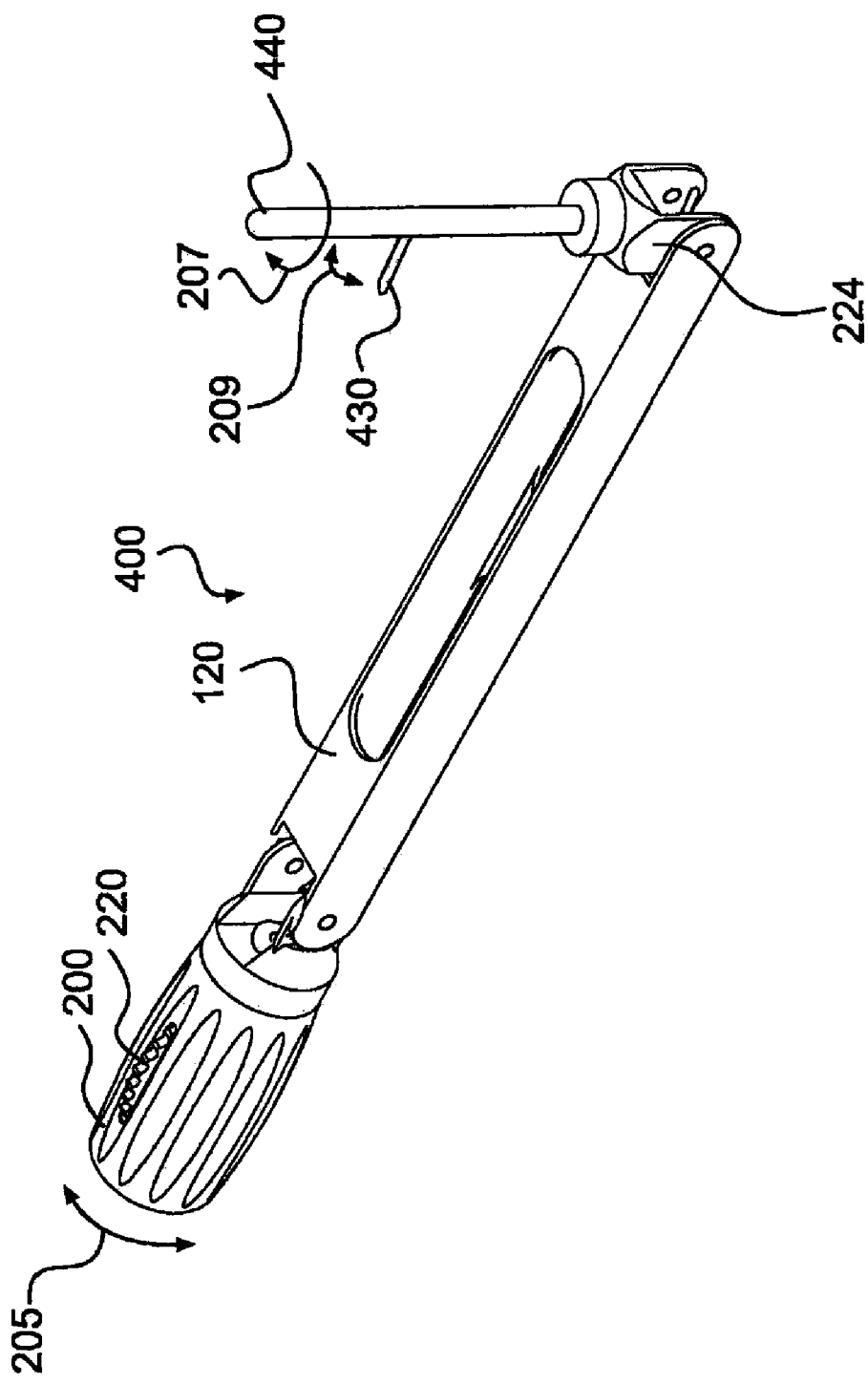
FIG. 19 is a perspective view of the medical device of FIG. 18 showing a cutting device in a deployed configuration.

Cutting device 430 may also be configured to rotate with manipulation device 440 in the directions of arrow 207 (FIG. 19). Rotation of cutting device 430 may be controlled by a second actuating mechanism 200. Second actuating mechanism 200 may be operably connected to cutting device 430 via control rod 242. Second actuating mechanism 200 and control rod 242 may substantively include the features of second actuating mechanism 200 and control rod 242 of medical device 100 shown in FIG. 10. For example, rotation of second actuating mechanism 200 in the directions of arrow 205 may cause control rod 242 to transfer rotational force to cutting device 430.

Manipulation device 440 may include one or more features of manipulation device 240 shown in FIG. 10. For example, manipulation device 440 may include an atraumatic exterior with a coating to facilitate insertion of medical device 400 into a patient. Manipulation device 440 may also include one or more lumens for insertion of surgical equipment, including, but not limited to, imaging and illumination devices, suction devices, biopsy tools, and drug-delivery mechanisms.

In order to maintain medical device 400 within a patient, manipulation device 440 may further include a gripping structure on its exterior surface (e.g., tines or barbs). Alternatively, medical device 400 may include expandable members like expandable members 180, 260 illustrated in FIG. 10 of the present disclosure.

Figure 21A:
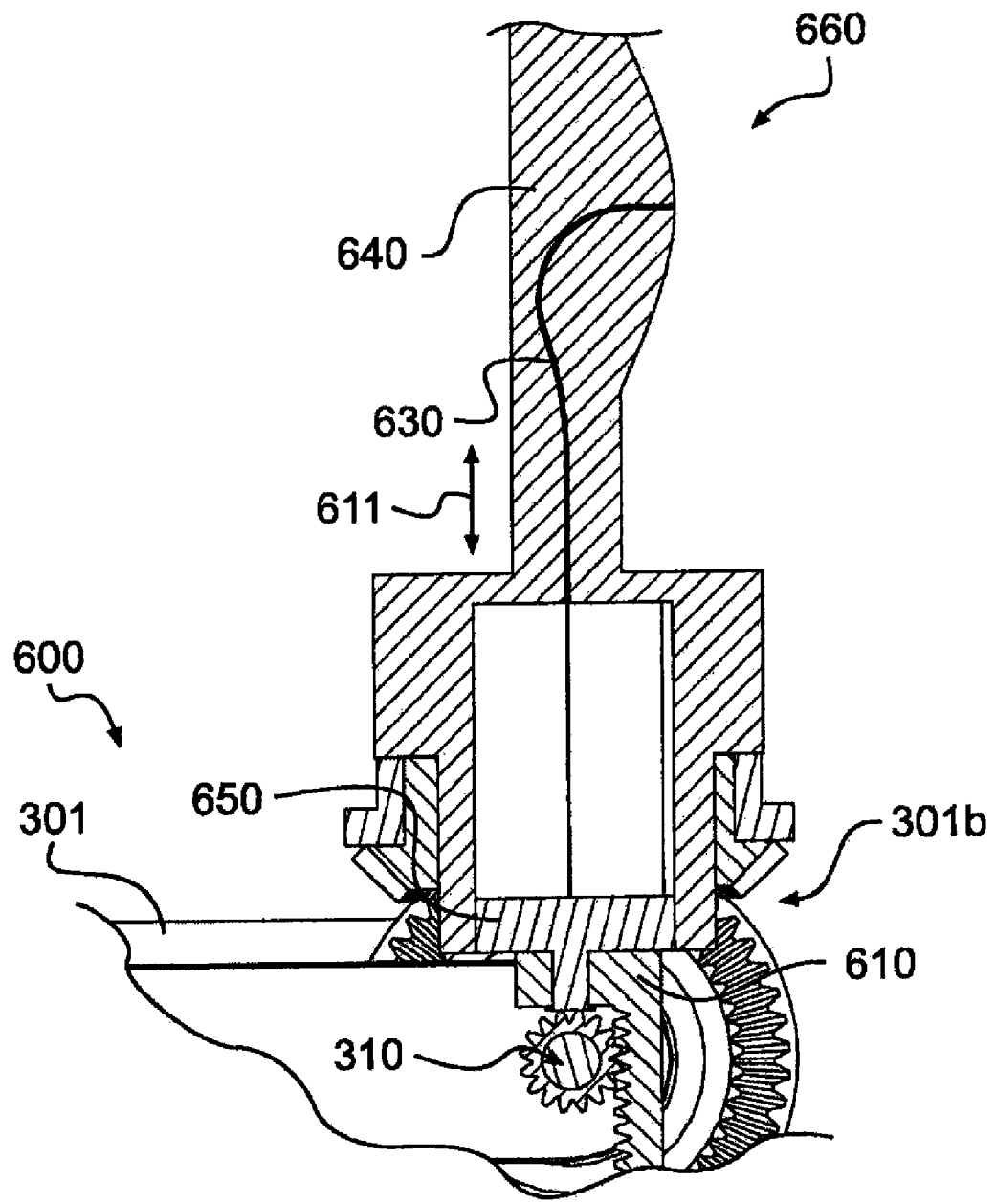
FIGS. 21A-21B are cross-sectional views of a distal end of a medical device for use in performing an LSH procedure, according to a sixth embodiment of the present disclosure, showing a cutting device in retracted and deployed configurations, respectively.
Figure 21B:
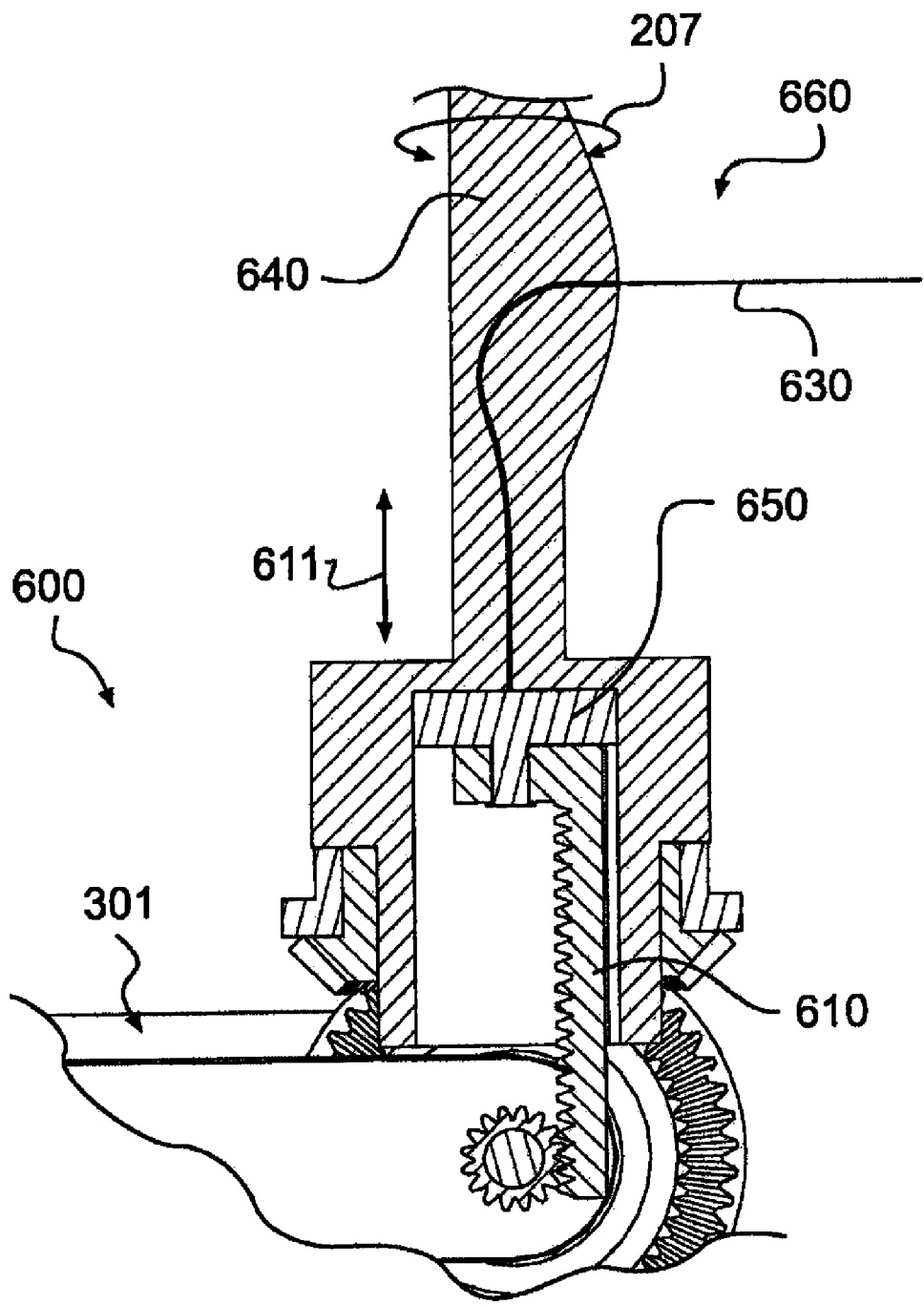

FIGS. 21A and 21B illustrate a cross-sectional view of a distal end of a medical device 600 for an LSH procedure, in accordance with a sixth embodiment of the present disclosure. Medical device 600 may include one or more features of medical device 100 shown in FIG. 10, medical device 300 shown in FIG. 13, and medical device 400 shown in FIG. 18. For example, medical device 600 may include an elongate member 301 with an end effector assembly 660 at its distal end 301*b*. Medical device 600 may also include expandable members like expandable members 180, 260 illustrated in FIG. 10 of the present disclosure. Further, as discussed in the present disclosure in relation to medical device 300 of FIG. 13, end effector assembly 660 may pivot about rod 310 due to movement from handle portion 302 in combination with a system of gears and belts.

End effector assembly 660 may include a manipulation device 640 and a cutting device 630. Manipulation device 640 may include one or more features of manipulation device 440 shown in FIG. 18, including, but not limited to, an atraumatic exterior surface with a coating, one or more lumens, and a means for maintaining medical device 600 within a patient.

Cutting device 630 may be configured to move between a retracted position (FIG. 21A) and a deployed position (FIG. 21B). Cutting device 630 may be deployed via a plunger 610. Plunger 610 may be part of a ratcheting system (FIG. 21A) that is operatively connected to cutting device carrier 650 and cutting device 630. Translational movement of a first actuating mechanism 312 may cause rotational movement of gears and belts, which in turn may cause translational movement of plunger 610 and cutting device carrier 650 in the directions of arrow 611, resulting in deployment and retraction of cutting device 630.

Cutting device 630 may be any cutting device known to those skilled in the art, such that cutting device 630 can be deployed and retracted along a path that may include linear and/or nonlinear sections (e.g., flexible blade or laser). Cutting device 630 may also be configured to rotate with manipulation device 640 in the directions of arrow 207 in response to rotation of a second actuating member 314 in the directions of arrow 317. Although the depicted embodiment illustrates cutting device 630 deployed at an angle of 90 degrees relative to manipulation device 640, cutting device 630 may extend at any suitable angle, preferably approximately between 15 and 90 degrees.

Figure 22A:
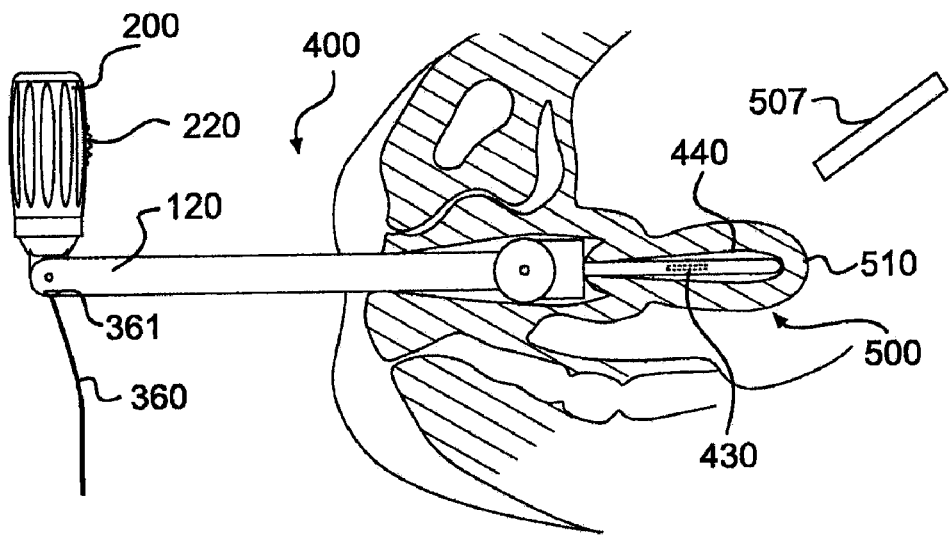
FIG. 22A is a cross-sectional view of a body portion showing the medical device of FIG. 18 inserted into a vaginal cavity for performing an LSH procedure.
Figure 22B:
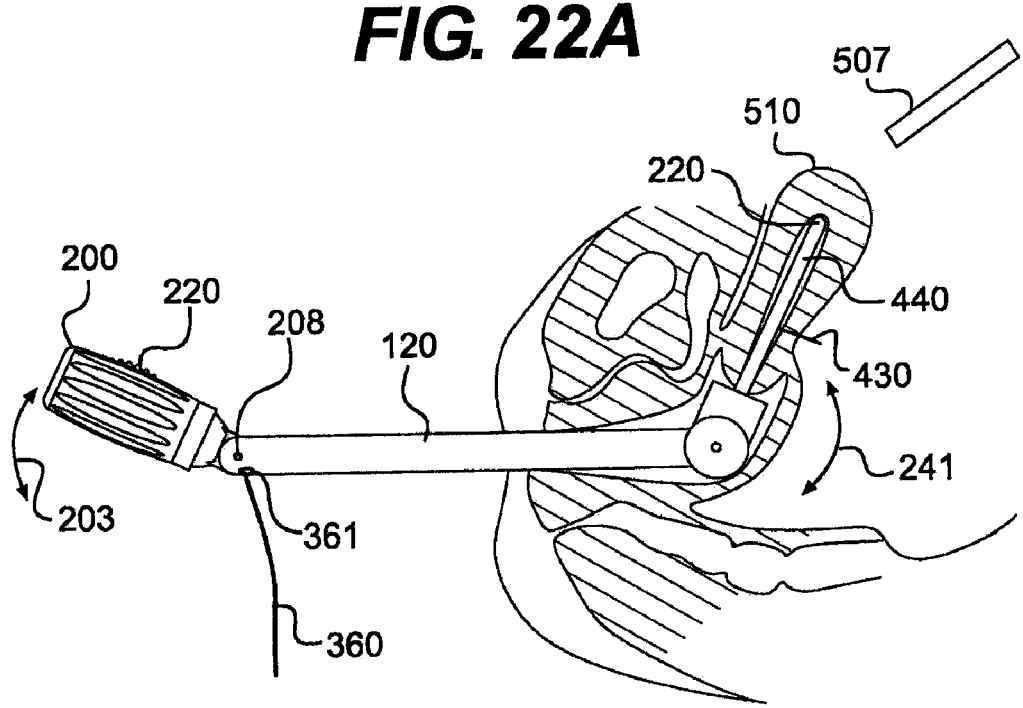
FIG. 22B is a cross-sectional view of a body portion showing the medical device of FIG. 18 inserted into a vaginal cavity and manipulating the position of a uterus for performing an LSH procedure.

FIGS. 22A and 22B of the present disclosure illustrate a method for performing an LSH procedure using medical device 400 of FIG. 18. Alternatively, medical device 600 of FIGS. 21A-21B may be used for the LSH procedure in place of medical device 400 of FIG. 18. The method illustrated in FIGS. 22A and 22B follows the same preparation steps as the method illustrated in FIGS. 5A-5C and 6. Medical device 400 may be maintained in a desired position via expandable members or other gripping means. A device operator may rotate handle portion 140 in the directions of arrow 203. Rotation of handle portion 140 may cause manipulation device 440 to pivot uterus 500 in the directions of arrow 241, which may place uterus 500 in a desired cutting orientation. Cutting device 430 may then be deployed and rotated via the use of the first and second actuating mechanisms 220, 200 in order to create a uniform, rounded incision to excise the uterine fundus 510 from the cervix, which is left in situ. Once uterine fundus 510 is withdrawn using accepted techniques to those skilled in the art, the vaginal cuff opening left behind is sutured or otherwise closed as known to those skilled in the art.

Figure 23:
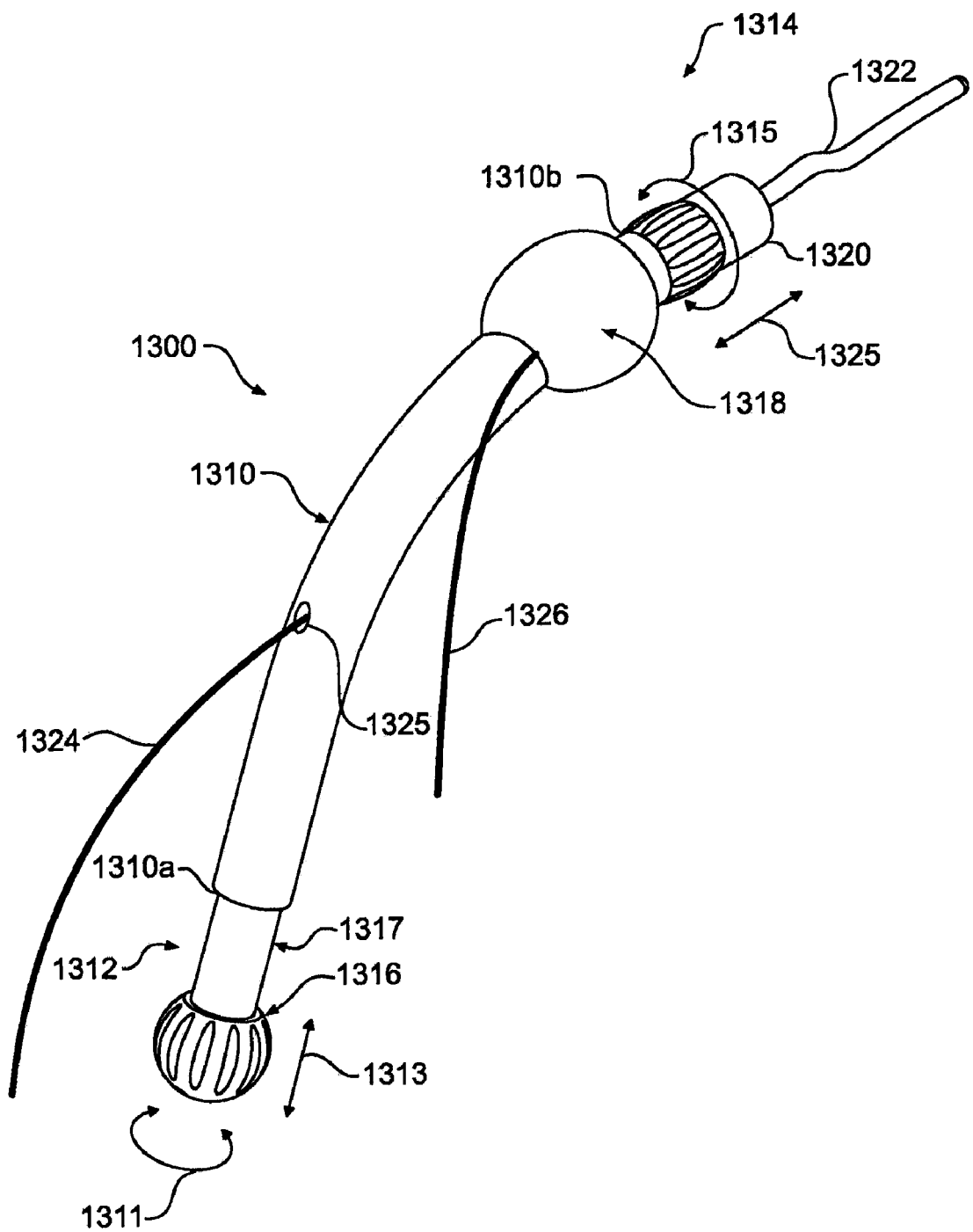
FIG. 23 is a perspective view of a medical device for use in performing an LSH procedure, according to a seventh embodiment of the present disclosure.

FIG. 23 illustrates another medical device 1300 for performing an LSH procedure, in accordance with a seventh embodiment of the present disclosure. Medical device 1300 may include one or more features of any of the other embodiments disclosed herein. For example, medical device 1300 may include an elongate member 1310, a handle portion 1312, an end effector assembly 1314, and an expandable member 1318. End effector assembly 1314 may be disposed at a distal end 1310*b* of elongate member 1310, and handle portion 1312 may be disposed at a proximal end 1310*a* of elongate member 1310.

Substantively, elongate member 1310 may be similar to elongate member 12 of FIG. 1. For example, elongate member 1310 may be a unitary hollow tube having sufficient flexibility to traverse a vaginal canal. Alternatively, elongate member 1310 may include two halves 1310' (FIG. 26) that may be connected via any connection means (e.g., welding, soldering, etc.) known to those skilled in the art. Elongate member 1310 may be curved along its length and include a proximal end 1310*a* and a distal end 1310*b*. Proximal end 1310*a* may include an opening in communication with a central lumen 1344 of elongate member 1310. Central lumen 1344 may also be in communication with an opening 1325 in an exterior surface of elongate member 1310. Opening 1325 in the exterior surface of elongate member 1310 may allow for passage of an electrical line 1324 providing electrical current cutting device 1330. Distal end 1310*b* may include a stop surface for providing a point beyond which, end effector assembly 1314 may not traverse. Further, distal end 1310*b* may include threads 1338 configured to mate with corresponding threads 1336 on end effector assembly 1314.

End effector assembly 1314 may extend distally from distal end 1310*b* of elongate member 1310 and may be removably attached to distal end 1310*b* by any connection means known to those skilled in the art. For example, as discussed above, in one embodiment, end effector assembly 1314 may include threads 1336 configured to mate with corresponding threads 1338 at distal end 1310*b* of elongate member 1310. Alternatively, end effector assembly 1314 may be telescopically connected to distal end 1310*b* of elongate member 1310, such that a connector portion 1320 of end effector assembly 1314 may be slidably engaged within central lumen 1344 of elongate member 1310. End effector assembly 1314 may be reusable or disposable. Alternatively, end effector assembly 1314 may be integral with elongate member 1310.

End effector assembly 1314 may include multiple components, including, but not limited to, a connector portion 1320, a manipulation device 1322, and a cutting device 1330. Manipulation device 1322 may extend through an opening, discussed in greater detail below, in connector portion 1320 and may be independently movable relative to connector portion 1320. Manipulation device 1322 may be disposable or reusable and may have any shape, configuration, and/or dimension, such that it may be received in a patient's vaginal cavity. For example, in one embodiment, manipulation device 1322 may include an s-shaped curve along its length. Alternatively, manipulation device 1322 may be substantially straight along its length, similar to manipulation device 440 of medical device 400 shown in FIG. 18. Manipulation device 1322 may also be a hollow tube with a lumen (not shown) for allowing passage of illumination and imaging devices, as well as tools for suction, irrigation, drug delivery, and uterine removal and manipulation. Further, manipulation device 1322 may have an atraumatic exterior configuration with a rounded surface and/or an anesthetic or lubricious coating.

Manipulation device 1322 may further include an expandable member (not shown) for securing medical device 1300 relative to a uterus. The expandable member may also serve the purpose of tensioning the uterine wall in an area of an incision made by cutting device 1330. Substantively, the expandable member may be similar to expandable member 26 of medical device 10 shown in FIG. 1. For example, the expandable member may be any suitable expansion means (e.g., balloon, cage, foam, etc.), and may be expanded via an expansion line (not shown), which may run through an opening similar to opening 1325 in the exterior surface of elongate member 1310.

Connector portion 1320 may be a hollow, cap-like structure having an opening configured to receive distal end 1310b of elongate member 1310. As discussed above, a distal endface of connector portion 1320 may include an opening through which manipulation device 1322 may pass. Connector portion 1320 may have a textured gripping portion on an exterior surface (FIG. 23) for allowing a device operator to rotate end effector assembly 1314 in the directions shown by arrow 1315. Rotation of connector portion 1320 in the directions shown by arrow 1315 may, as a result of the connection between threads 1336, 1338, result in translational movement of end effector assembly 1314 in the directions shown by arrow 1325. As discussed above, connector portion 1320 may further be telescopically connected to distal end 1310b of elongate member 1310, such that it may move in the directions shown by arrow 1325 relative to elongate member 1310 (FIG. 31C). Connector portion 1320 may also include a locking mechanism (not shown) in order to maintain a desired relationship relative to elongate member 1310. In additional embodiments, a distal end of connector portion 1320 may include integrated visualization devices, such as, e.g., light sources or light guide tubes and/or cameras. Furthermore, such embodiments may be configured to deliver irrigation and/or suction to the surgical site.

Connector portion 1320 may be any shape and/or configuration, such that it may be received in a patient's vaginal cavity. For example, in one embodiment, connector portion 1320 may be a cup with an enclosed edge for engaging vaginal fornices (FIGS. 32A-32D). Further, connector portion 1320 may have any suitable atraumatic configuration at its distal end, including, but not limited to, a rounded exterior surface. Connector portion 1320 may also include a textured geometry on its exterior surface for frictionally gripping patient tissue to aid in maintaining desired placement of medical device 1300.

Medical device 1300 may further include handle portion 1312 extending proximally from proximal end 1310a of elongate member 1310. Handle portion 1312 may include a gripping portion 1316 and a telescoping portion 1317. Telescoping portion 1317 may be an elongate structure having a diameter that is less than the diameter of the opening at proximal end 1310a of elongate member 1310, thereby allowing telescoping portion 1317 to slide within central lumen 1344 of elongate member 1310 in the directions shown by arrow 1313. Gripping portion 1316 may extend proximally from telescoping portion 1317 and may include a textured surface for aiding a device operator with manipulation of handle portion 1312. In addition to telescopic movement, handle portion 1312 may be rotated relative to elongate member 1310 in the directions shown by arrow 1311.

Figures 24A, 24B:
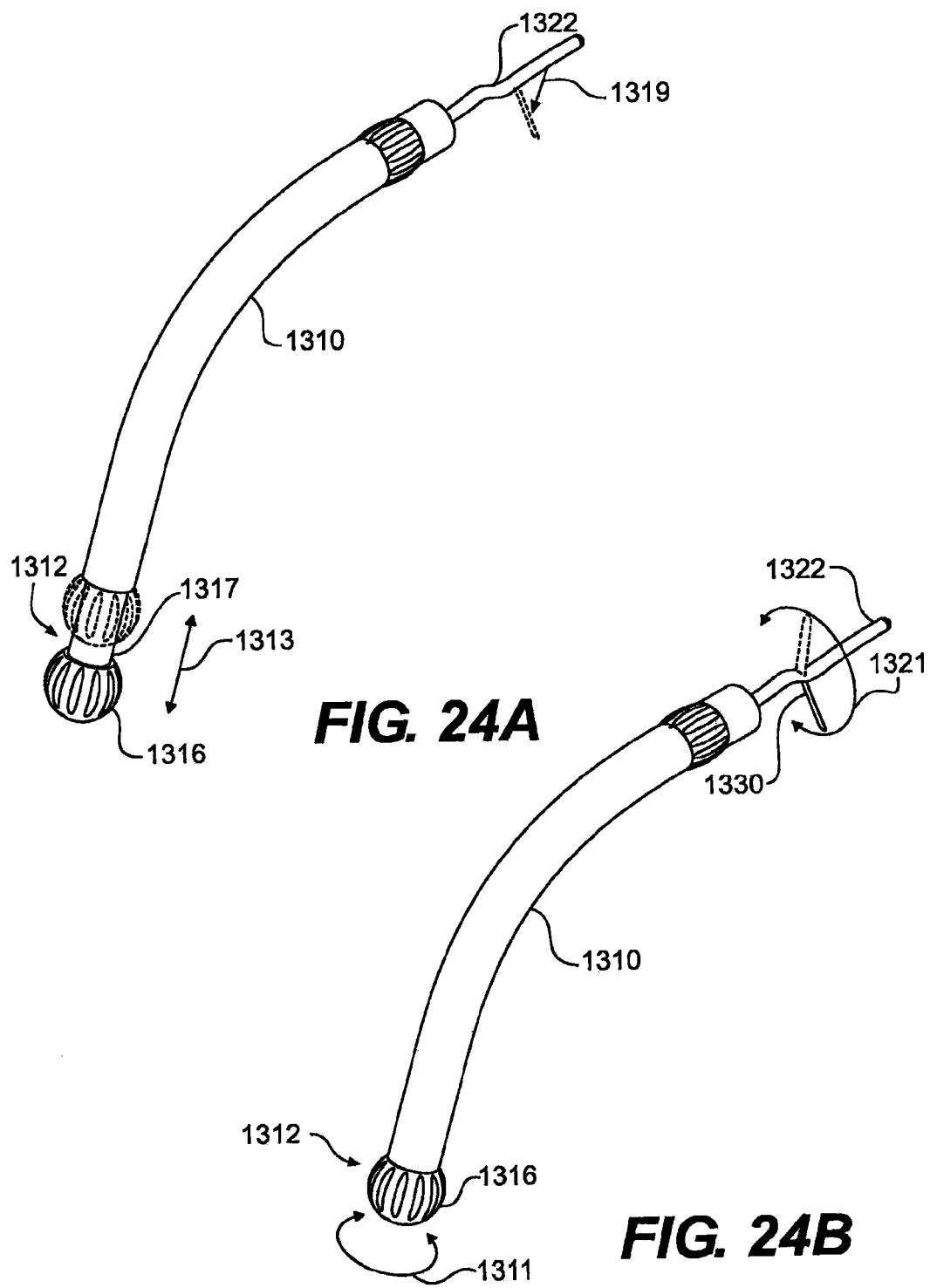
FIGS. 24A-24B are perspective views of the medical device of FIG. 23 with a cutting device in retracted and deployed positions, respectively.

Movement of handle portion 1312 relative to elongate member 1310 may control movement of cutting device 1330. For example, as illustrated in FIG. 24A, the device operator may move handle portion 1312 in the directions of arrow 1313 to move cutting device 1330 in the direction of arrow 1319 between a deployed position and a retracted position. Further, as illustrated in FIG. 24B, the device operator may rotate handle portion 1312 in the directions of arrow 1311 to rotate cutting device 1330 in the directions of arrow 1321. Although cutting device 1330 is illustrated as being deployed perpendicularly to manipulation device 1322, cutting device 1330 may be deployed at any suitable angle. For example, a suitable deployment angle from manipulation device 1322 may be anywhere in the range of approximately 15 degrees to 90 degrees, and preferably approximately 45 degrees. Accordingly, handle portion 1312 may include features (e.g., markings) to indicate the deployed and/or rotational positions of cutting device 1330 relative to, e.g., the central axis of manipulation device 1322.

Figure 25:
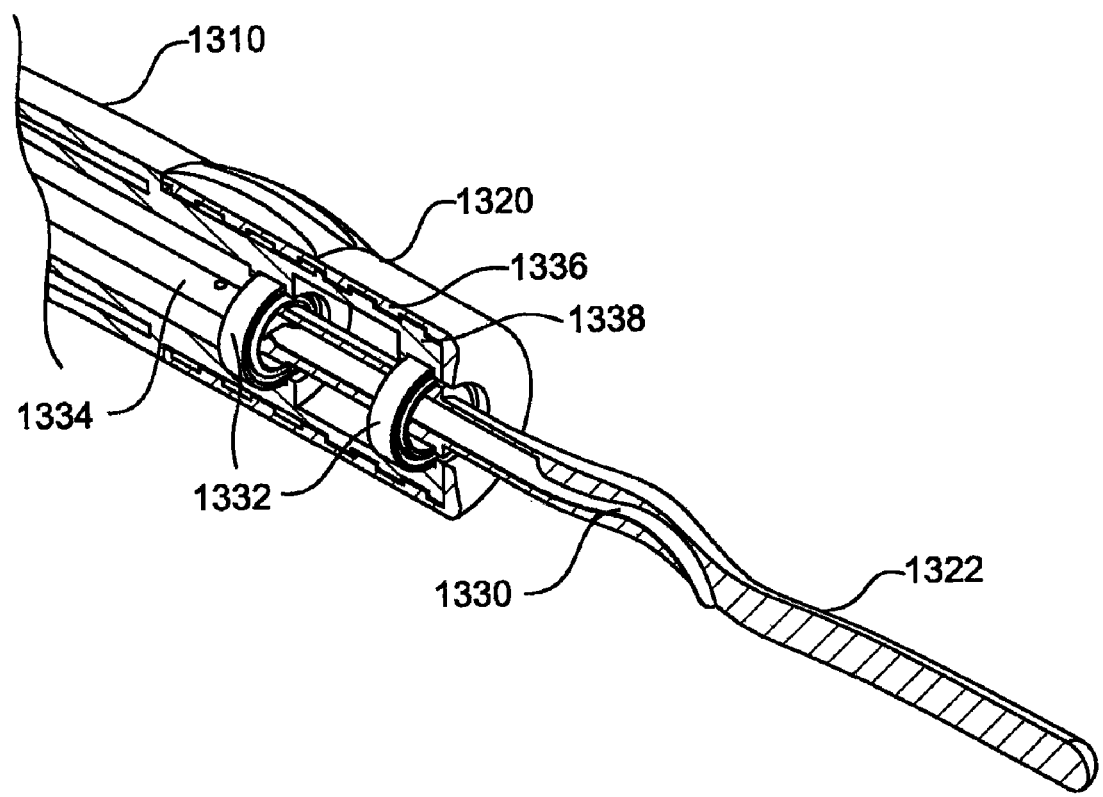
FIG. 25 is a sectional view of a distal end of the medical device of FIG. 23.
Figure 26:
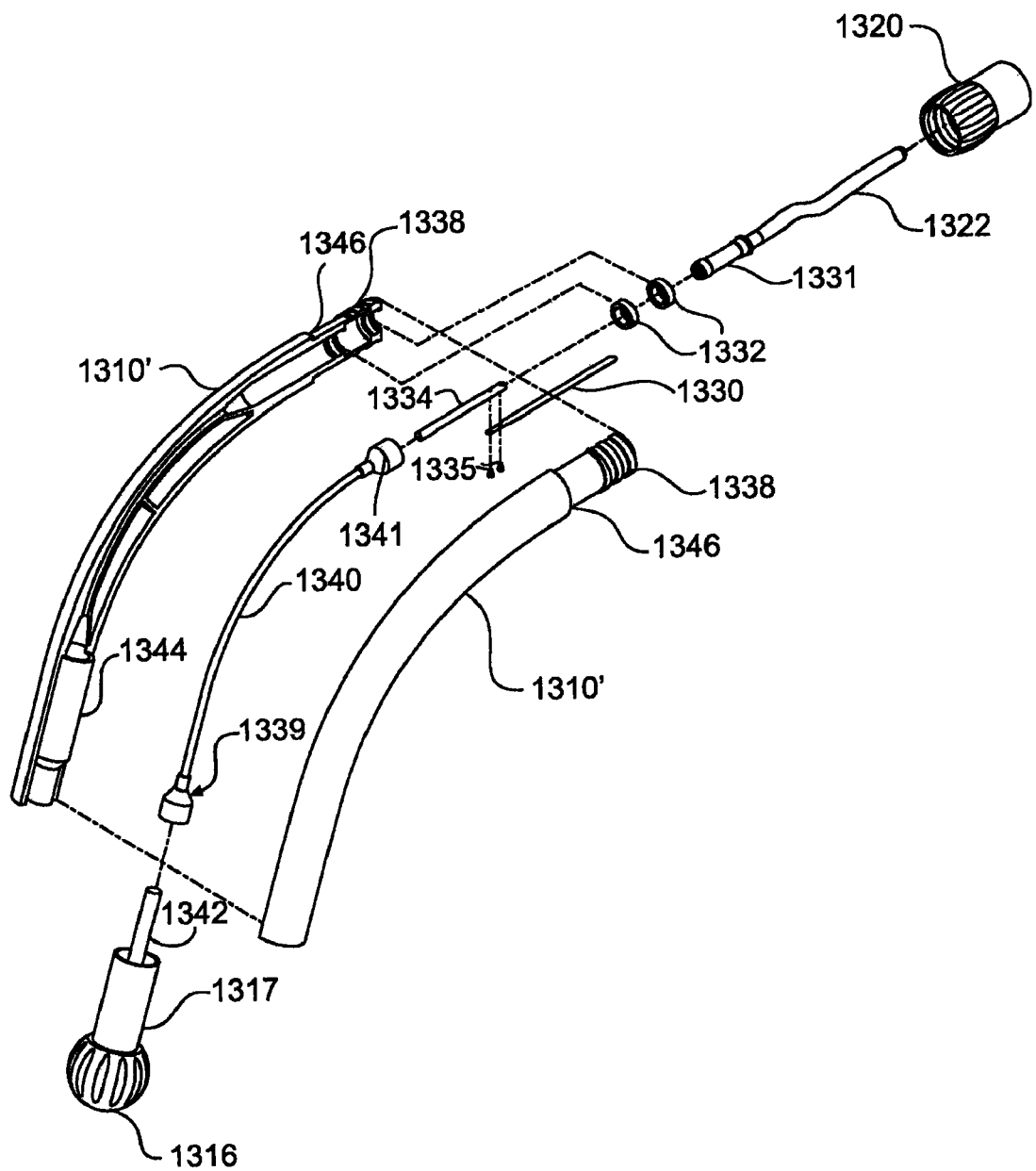
FIG. 26 is an exploded view of the medical device of FIG. 23.

As illustrated in FIGS. 25 and 26, medical device 1300 may further include multiple components within central lumen 1344 of elongate member 1310 that are operably connected to handle portion 1312 for controlling movement of cutting device 1330. For example, telescoping portion 1317 may include a first rod 1342 that may be operably connected to a first end 1339 of a plunger 1340. A second end 1341 of plunger 1340 may be operably connected to a second rod 1334, which may be pivotally connected by pins 1335 to cutting device 1330. Bearings 1332 may support and aid rotation of manipulation device 1322 in the directions of arrow 1321. Bearings 1332 may further provide a stop surface for plunger 1340, such that second end 1341 of plunger 1340 may not move beyond that point. In use, movement of handle portion 1312 in the directions shown by arrow 1313 may cause first rod 1342 to act on plunger 1340, which in turn may cause second rod 1334 to move within a lumen in a proximal end 1331 of manipulation device 1322 and pivot cutting device 1330 in the direction shown by arrow 1319 into a deployed configuration. Further, rotation of handle portion 1312 in the directions of arrow 1311 may cause first rod 1342 to act on plunger 1340, which may operably act on proximal end 1331 of manipulation device 1322, causing rotation of manipulation device 1322 with cutting device 1330.

Cutting device 1330 may be any known cutting device to those skilled in the art, including, but not limited to, radiofrequency (RF) devices, lasers, microwave probes, and/or ultrasonic ablation devices. As illustrated in FIG. 25, cutting device 1330 may also be a flexible cautery blade configured to conform the curvature of manipulation device 1322 when cutting device 1330 is in a retracted position within manipulation device 1322. Alternatively, cutting device 1330 may be a substantially flat and/or rigid blade, similar to cutting device 430 of medical device 400 shown in FIG. 19. As discussed above, cutting device 1330 may be connected to electrical line 1324, and electrical line 1324 may further extend through opening 1325 in the exterior surface of elongate member 1310, thereby allowing for a connection to an external energy source (not shown). FIG. 25 also depicts a single cutting device 1330 in a retracted position within manipulation device 1322. Alternatively, medical device 1300 may include multiple cutting devices 1330 circumferentially spaced around manipulation device 1322, such that each cutting device 1330 may be independently deployed. In embodiments with multiple cutting devices 1330, it is contemplated that cutting devices 1330 may be collectively deployed as well.

In some embodiments, medical device 1300 may further include an expandable member 1318 on an exterior surface of elongate member 1310. Expandable member 1318 may be substantively similar to expandable member 18 of medical device 10 shown in FIG. 1. For example, expandable member 1318 may be an occluder in the form of a vaginal dam for preventing leakage of a gas upon inflation of a patient's abdomen. Expandable member 1318 may also be connected to expansion control line 1326 for moving expandable member 1318 between deployed and retracted configurations. In embodiments where expandable member 1318 is inflatable, expansion control line 1326 may provide a passageway for inflation fluids. Expandable member 1318 may also include sensors, radiopaque markers, and/or pressure limiting valves for monitoring the force expandable member 1318 may exert on a patient's tissue and for monitoring the relative expansion of expandable member 1318.

Figure 27:
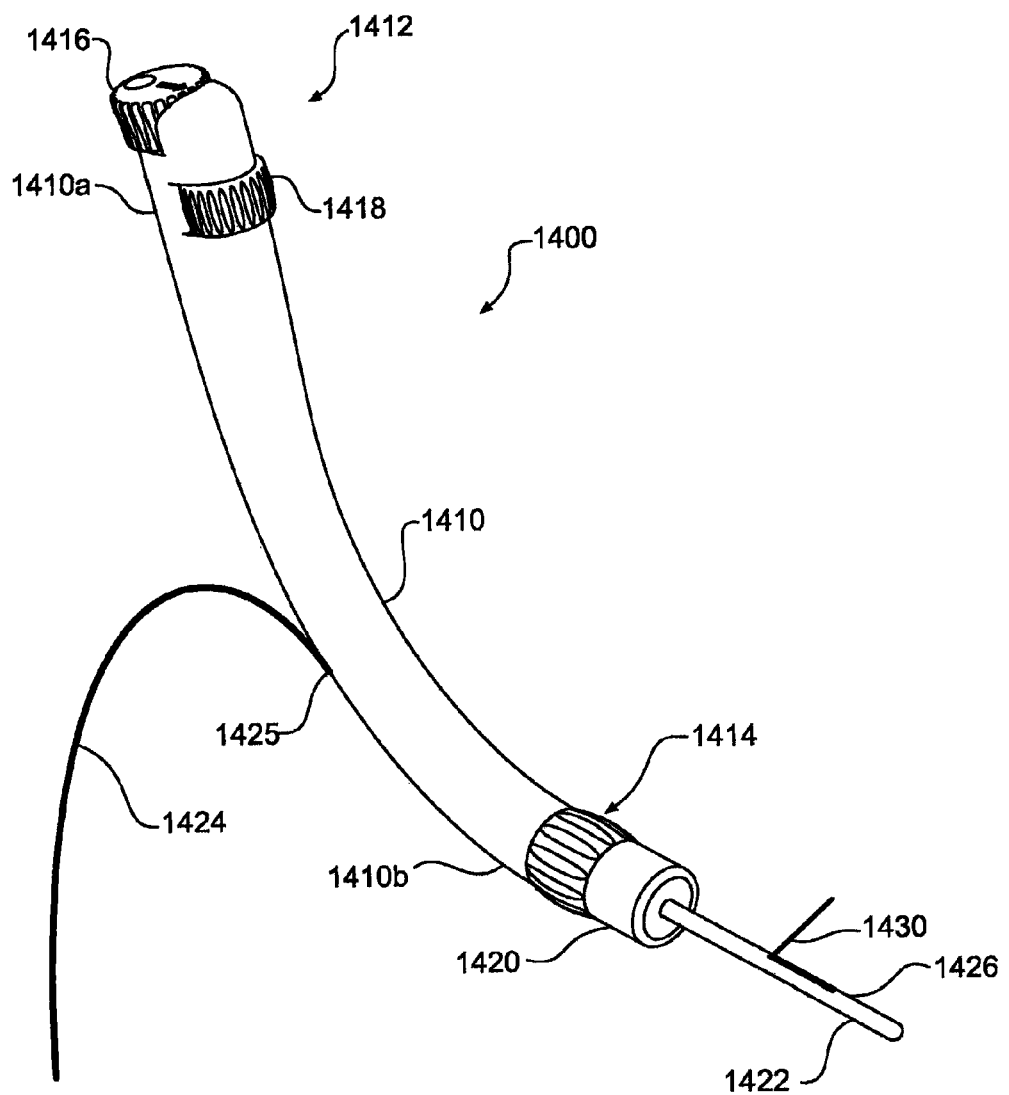
FIG. 27 is a perspective view of a medical device for use in performing an LSH procedure, according to an eighth embodiment of the present disclosure.

FIG. 27 illustrates another medical device 1400 for performing an LSH procedure, in accordance with an eighth embodiment of the present disclosure. Medical device 1400 may include one or more features of any of the embodiments disclosed herein. For example, elongate member 1410, end effector assembly 1414, and cutting device 1430 may be substantively similar to elongate member 1310, end effector assembly 1314, and cutting device 1330, respectively, of medical device 1300 in FIG. 23. Further, medical device 1400 may include an expandable member (not shown) on elongate member 1410 that is substantially similar to expandable member 1318 of medical device 1300 in FIG. 23.

Elongate member 1410 may be a curved, hollow tube that may be a unitary structure or may include two halves 1410'. Elongate member 1410 may be any shape and/or configuration, and may be made of a biocompatible material with sufficient flexibility/rigidity to traverse a patient's vaginal and uterine cavities. Elongate member 1410 may further include a proximal end 1410a, a distal end 1410b, and an opening 1425. Opening 1425 may be substantively similar to opening 1325 in elongate member 1310 shown in FIG. 23. For example, opening 1425 may serve as an entry/exit point for an electrical line 1424 that may be connected to cutting device 1430. Further, distal end 1410b may be substantively similar to distal end 1310b of medical device 1300 shown in FIG. 23. For example, distal end 1410b may include threads 1450 configured to mate with corresponding threads 1451 on end effector assembly 1414. Distal end 1410b may also include a stop surface 1452 for limiting movement of end effector assembly 1414 relative to elongate member 1410. Other embodiments of medical device 1400 may include a cup (not shown) configured to engage vaginal/cervical tissue to make them taut.

End effector assembly 1414 may be substantively similar to end effector assembly 1314 of medical device 1300 shown in FIG. 23. For example, end effector assembly 1414 may include a manipulation device 1422 that is substantively similar to manipulation device 1322 of medical device 1300 shown in FIG. 23. As illustrated in FIG. 27, manipulation device 1422 may be a substantially straight, elongate member. Alternatively, manipulation device 1422 may include an S-shaped configuration, or any other suitable geometric features, along its length, similar to manipulation device 1322 shown in FIG. 23. Manipulation device 1422 may also include an expandable member (not shown) for securing medical device 1400 relative to a uterus and/or for tensioning the uterine wall in an area of an incision made by cutting device 1430, as discussed above in relation to manipulation device 1322 shown in FIG. 23.

End effector assembly 1414 may also include a connector portion 1420 that is substantively similar to connector portion 1320 of medical device 1300 shown in FIG. 23. For example, connector portion 1420 may be a hollow structure having an opening at a distal end with a diameter sufficient to receive distal end 1410b of elongate member 1410. Further, as discussed above, connector portion 1420 may include threads 1451 configured to mate with threads 1450 on distal end 1410b of elongate member. Connector portion 1420 may also include a textured gripping portion on an exterior surface thereby allowing a device operator to move end effector assembly 1414 relative to elongate member 1410.

Figure 29:
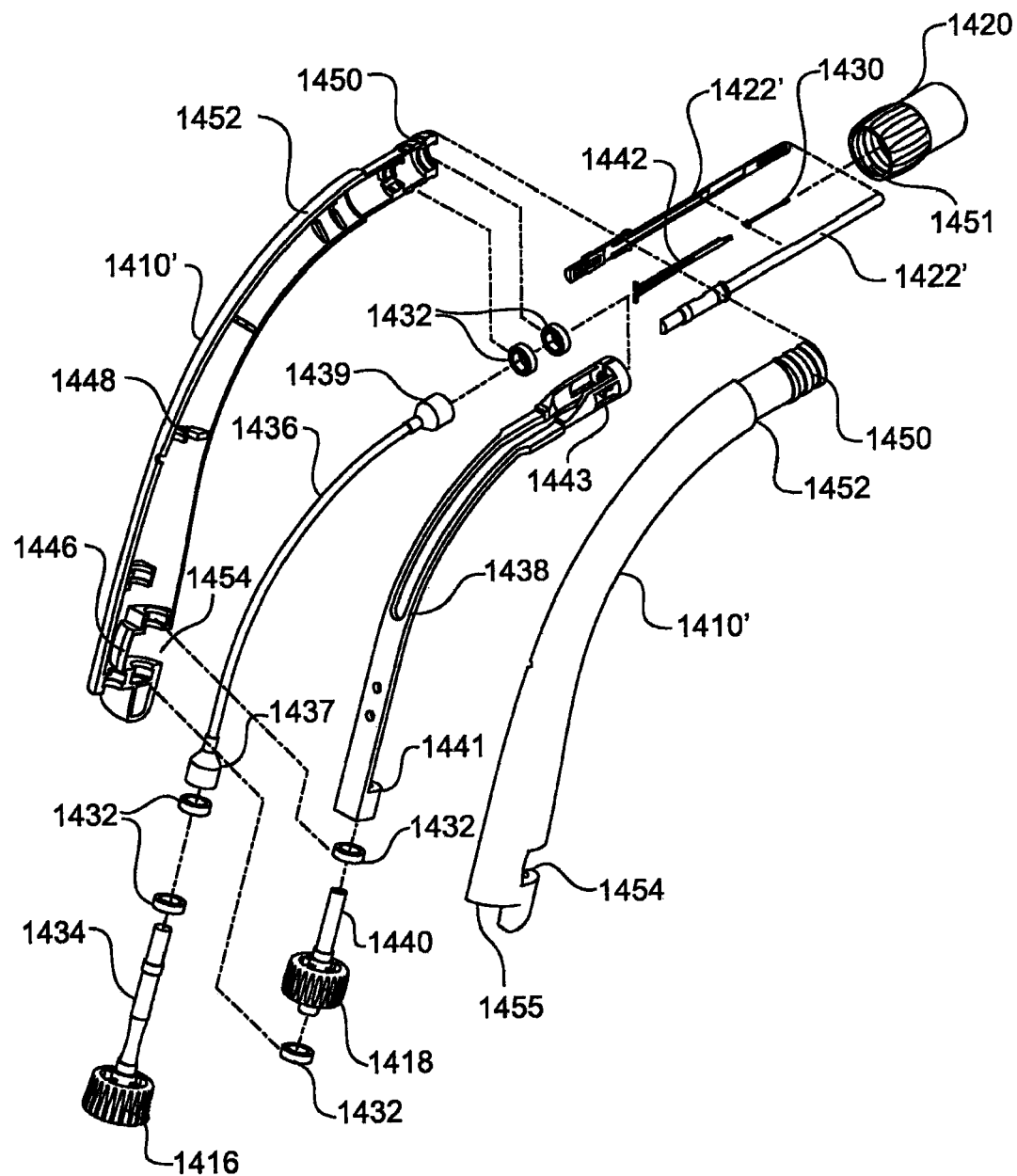
FIG. 29 is an exploded view of the medical device of FIG. 27.

Proximal end 1410a of elongate member 1410 may include first and second seats 1454, 1455 for housing first and second actuating mechanisms 1416, 1418, which may control movement of cutting device 1430. Although the depicted embodiment illustrates two such seats, those of ordinary skill in the art will recognize that a greater or lesser number of seats may be provided on elongate member 1410. First seat 1454 may be an opening through the exterior surface of elongate member 1410 and may be in communication with a central lumen 1448 in elongate member 1410. As illustrated in FIG. 29, the opening of first seat 1454 may include a back portion 1446 such that the opening may not extend completely through elongate member 1410. Second seat 1455 may be a ledge at proximal end 1410a of elongate member 1410 with an opening in communication with central lumen 1448 of elongate member 1410 (FIG. 29). Second seat 1455 may also be located at the proximal-most portion of medical device 1400. Indeed, a portion of second seat 1455 may include a proximal end face of elongate member 1410.

Figures 28A, 28B:
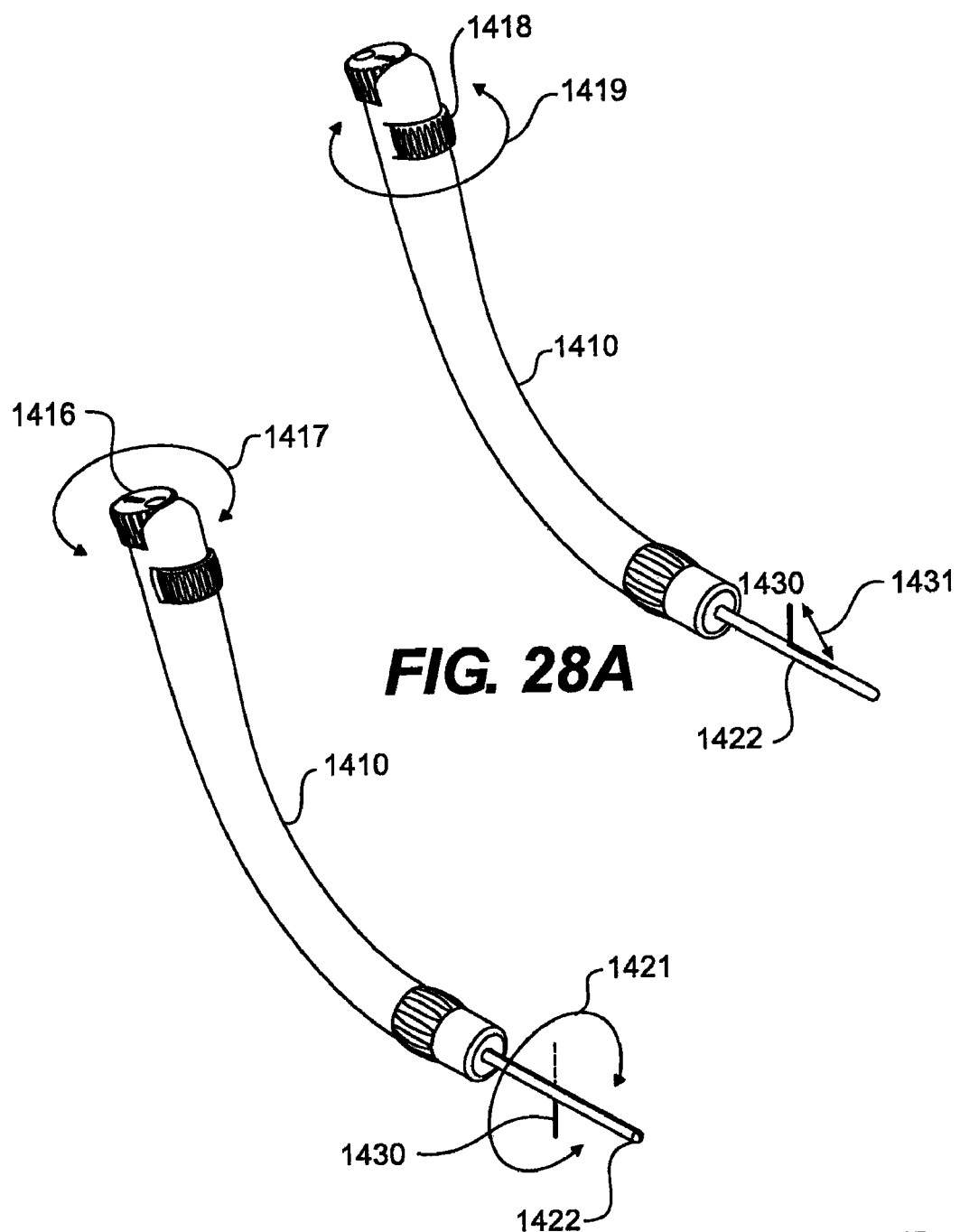
FIGS. 28A-28B are perspective views of the medical device of FIG. 27 with a cutting device in first and second rotational positions, respectively.

As discussed above, medical device 1400 may include first and second actuating mechanisms 1418, 1416 for controlling movement of cutting device 1430. First and second actuating mechanisms 1418, 1416 may be any movable device capable of deploying and rotating cutting device 1430, including, but not limited to, thumbwheels, push buttons, and switches. In one embodiment, first and second actuating mechanisms 1418, 1416 may be knobs capable of rotating in the directions of arrows 1417 and 1419, respectively (FIGS. 28A-28B). Rotation of first actuating mechanism 1418 may control deployment of cutting device 1430 in the directions of arrow 1431, and rotation of second actuating mechanism 1416 may control rotation of manipulation device 1422 with cutting device 1430 relative to elongate member 1410 in the directions of arrow 1421.

Figure 30:
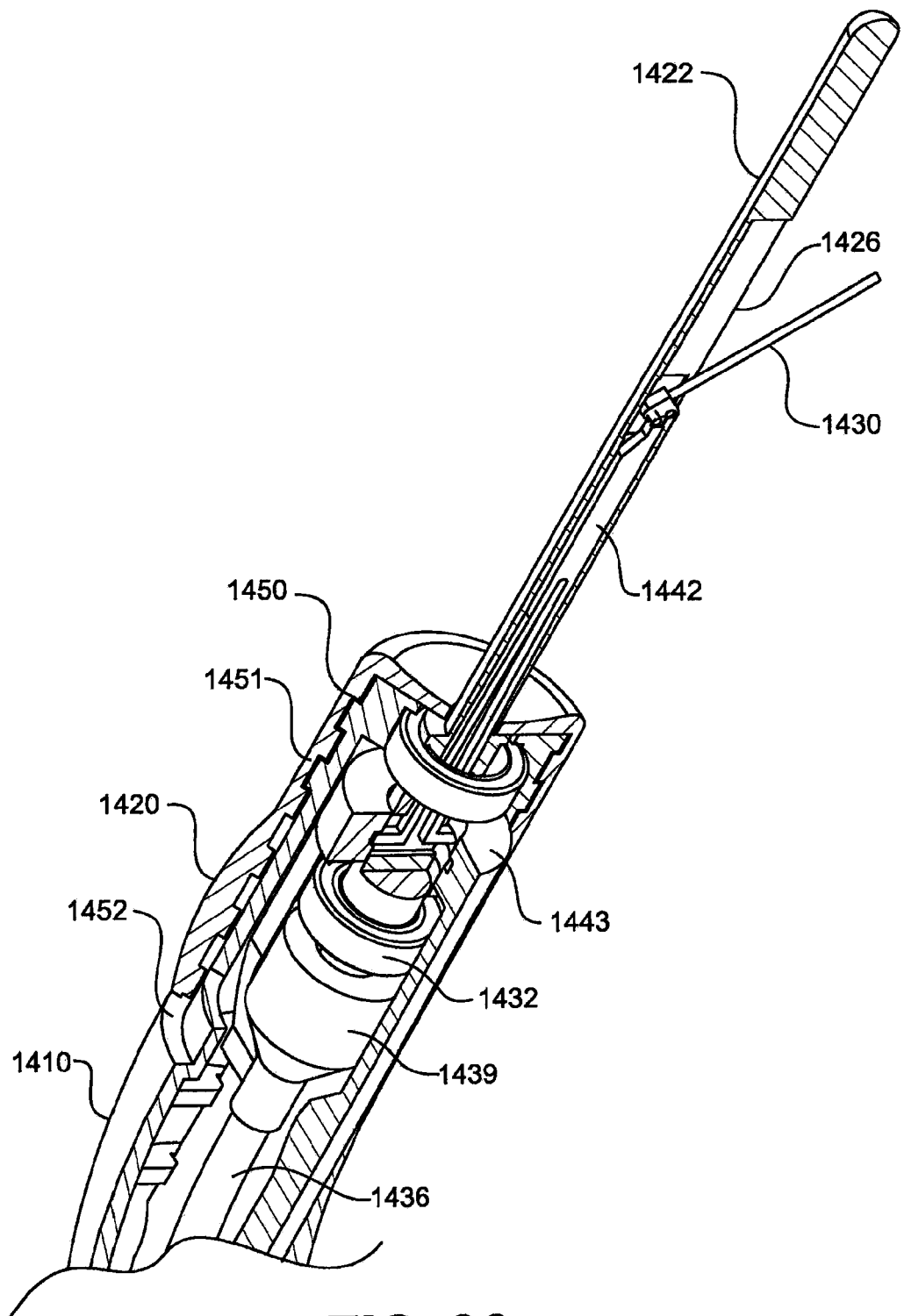
FIG. 30 is a sectional view of a distal end of the medical device of FIG. 27.

As shown in FIGS. 29 and 30, medical device 1400 may further include multiple components in operable communication with first and second actuating mechanisms 1418, 1416 for controlling deployment and rotation of cutting device 1430. First actuating mechanism 1418 may include a first rod 1440, which may be in communication via a screw mechanism with a first end 1441 of a first plunger 1438, housed within central lumen 1448 of elongate member 1410. A second end 1443 of first plunger 1438 may be in communication with a second rod 1442 pivotally attached to cutting device 1430. In its retracted position (not shown), cutting device 1430 may be housed within an opening 1426 in manipulation device 1422 (FIG. 30). Medical device 1400 may also include a plurality of bearings 1432 to provide rotational support. Bearings 1432 may also act as stop surfaces and aid in maintaining desired distances between certain components (FIG. 30). In use, rotation of first actuating mechanism 1418 may cause first rod 1440 to act on first plunger 1438, and in turn, act on second rod 1442 to pivot cutting device 1430 to a deployed configuration (FIG. 28A).

Second actuating mechanism 1416 may further include a third rod 1434 that acts on a second plunger 1436. Rotation of second actuating mechanism 1416 may cause second plunger 1436 to translate a rotational force to a proximal end of manipulation device 1422, which subsequently may result in rotation of manipulation device 1422 and cutting device 1430 relative to elongate member 1410.

Cutting device 1430 may be substantively similar to cutting device 1330 of medical device 1300 shown in FIG. 23. For example, cutting device 1430 may be any cutting device known to those of skill in the art, such as a laser, RF device, or microwave probe. FIG. 30 illustrates that cutting device 1430 may also be a flat, cautery blade connected to electrical line 1424, which may be connected to an external energy source (not shown). Further, as shown in FIGS. 28A-28B and 30, cutting device 1430 may deploy at any suitable angle (e.g., 45 degrees, 90 degrees, etc.).

Figure 31A:
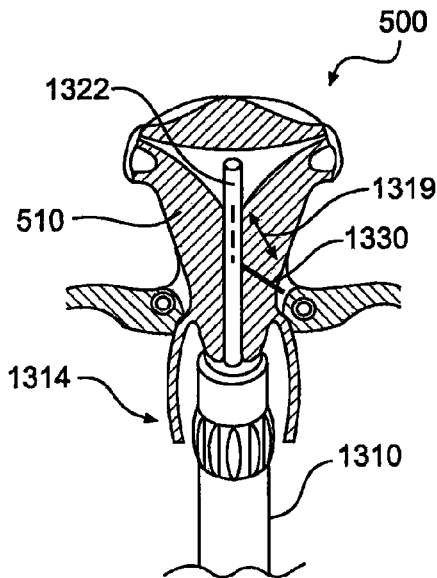
FIGS. 31A-31B are sectional views of a body portion showing the medical device of FIG. 27 excising the uterus during an LSH procedure.
Figure 31B:
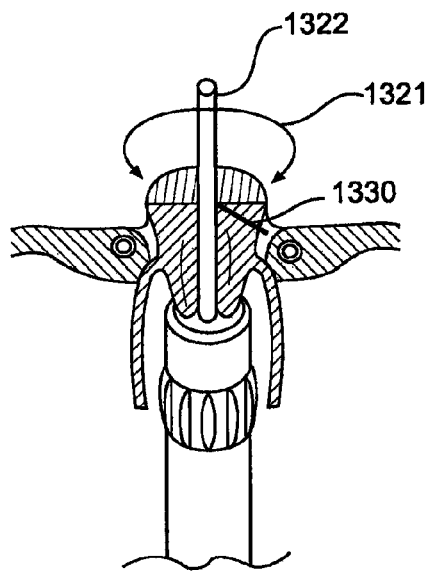
Figure 31C:
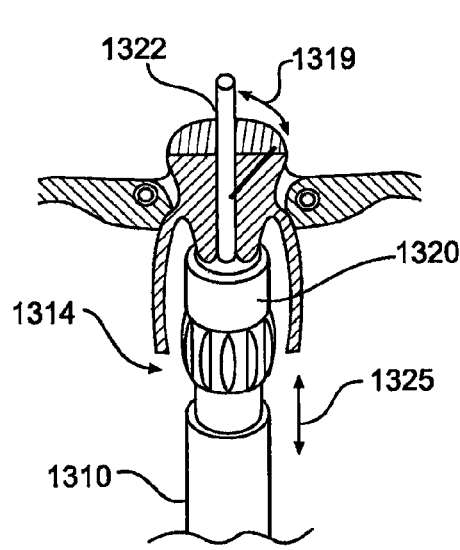
FIGS. 31C-31D are sectional views of a body portion showing the medical device of FIG. 27 performing a conoscopy of cervical tissue.

FIGS. 31A and 31B of the present disclosure illustrate an embodiment of a method for performing an LSH procedure using medical device 1300 of FIG. 23. Alternatively, medical device 1400 of FIG. 27 may be used for the LSH procedure in place of medical device 1300 of FIG. 23. The method illustrated in FIGS. 31A and 31B follows the same preparation steps as illustrated in FIGS. 5A-5C and 6. A device operator may move handle portion 1312 in the direction of arrow 1313, such that telescoping portion 1317 may slide within lumen 1344 of elongate member 1310, in the direction of arrow 1313, to deploy cutting device 1330. The device operator may then rotate handle portion 1312 in the direction of arrow 1311, such that cutting device 1330 may rotate relative to elongate member 1310 in order to create a uniform, rounded incision to excise the uterine fundus 510 from the cervix, which is left in situ. The uterine fundus 510 is then withdrawn using accepted techniques, and the vaginal cuff opening left behind may be sutured or otherwise closed as known to those skilled in the art.

Figure 31D:
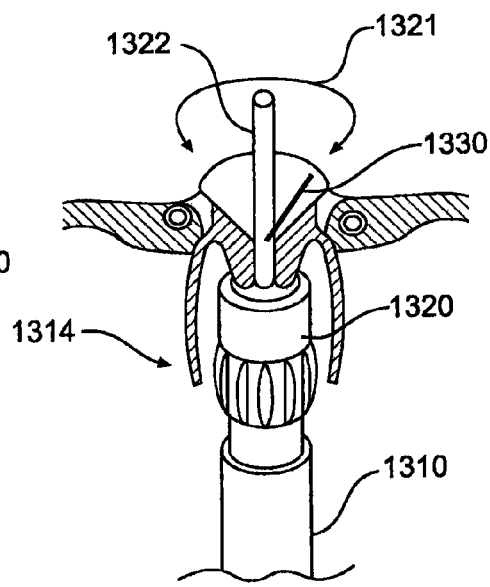

FIGS. 31C and 31D of the present disclosure illustrate an embodiment of a method for performing an conoscopy of the cervix. A conoscopy of the cervix may involve coring out tissue in the cervix after the uterine fundus 510 is removed during an LSH procedure. A device operator may position medical device 1300 for a conoscopy by partially retracting cutting device 1330 and by moving end effector assembly 1314 relative to elongate member 1310 in the direction of arrow 1325. Cutting device 1330 may be partially retracted, as shown in FIG. 31C, in the direction of arrow 1319, until a desired angle of cutting device 1330 is reached. The desired angle may be in the range of fifteen (15) to ninety (90) degrees, inclusive. FIG. 31D illustrates that, upon retracting cutting device 1330 to the desired angle, the device operator may rotate handle portion 1312 in the direction of arrow 1311 in order to rotate cutting device 1330 relative to elongate member 1310, such that coring of cervical tissue may be achieved.

FIGS. 32A-32D illustrate a medical device 1800 for performing an LSH procedure according to a ninth embodiment of the present disclosure. FIGS. 32A-32D also illustrate a method for performing an LSH procedure and a conoscopy using the ninth embodiment of the present disclosure. Medical device 1800 may be substantively similar to medical device 1300 shown in FIG. 23 and medical device 1400 shown in FIG. 27. For example, medical device 1800 may include an elongate member 1810, a manipulation device 1822, a cutting device 1830, and a connector portion 1820. Elongate member 1810, manipulation device 1822, and cutting device 1830 may be substantively similar to elongate member 1310, manipulation device 1322, and cutting device 1330, respectively, of medical device 1300 in FIG. 23. Manipulation device 1822 may include an expandable member 1824 for tensioning the uterine wall, as discussed above in relation to manipulation device 1322 of medical device 1300 shown in FIG. 23. Alternatively, tensioning of uterine wall may be accomplished using any means known to those skilled in the art. For example, tensioning of uterine wall may occur via gripping tools (e.g., forceps, prongs) that may extend through any suitable lumen in medical device 1800 and into the uterine cavity to grasp the uterine wall. Alternatively, a gripping tool (not shown) may be advanced into a patient's abdominal cavity through, e.g., a laparoscopic port, to facilitate gripping a portion of the patient's uterus and pulling proximally. Additionally, connector portion 1820 may be a cup for applying a cephalad force to a patient such that fornices 508 may be tented, thereby creating space and allowing easier removal of the uterine fundus 510.

Figure 32A:
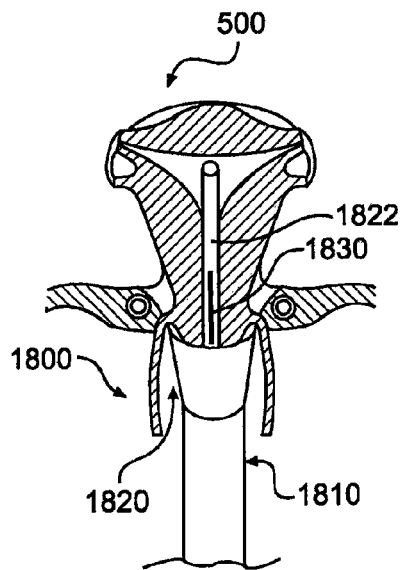
FIGS. 32A-32D illustrate a method for performing LSH and conization procedures.
Figure 32B:
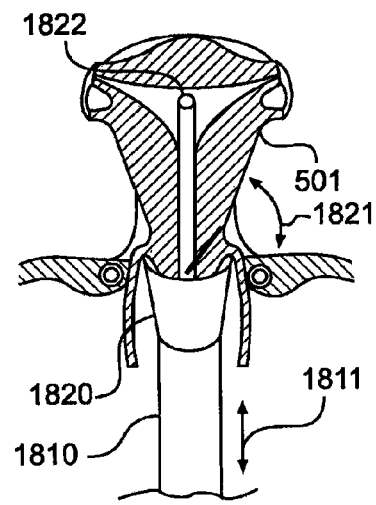
Figure 32C:
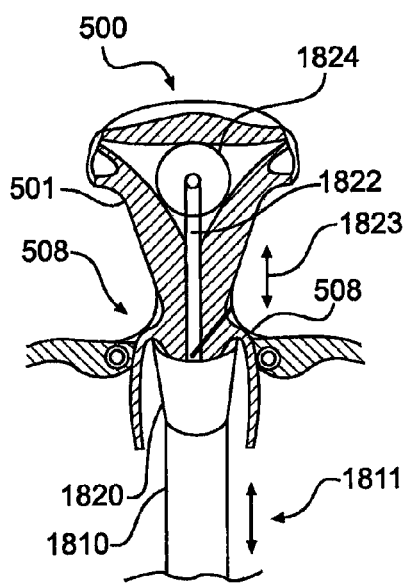
Figure 32D:
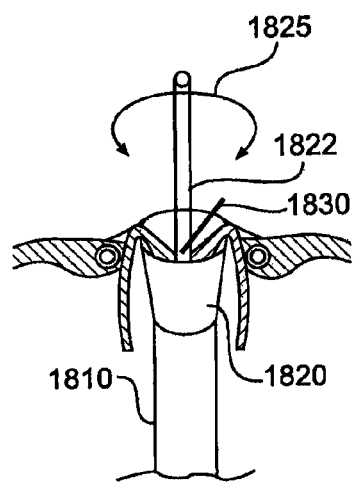

In use, after a patient is prepared and medical device 1800 is inserted, a device operator may push medical device 1800 to apply a cephalad force in the directions of arrow 1811 to tent fornices 508. The device operator may then deploy cutting device 1830 in the directions of arrow 1821, as illustrated in FIG. 32B. Prior to rotating cutting device 1830, the device operator may expand expandable member 1824 on manipulation device 1822 in order to exert tensioning forces on the uterine wall at an area of the incision in the directions of arrow 1823. Cutting device 1830 may then be rotated in the directions of arrow 1825 in order to excise the uterine fundus 510 and perform a conoscopy procedure. The vaginal cuff opening left behind may be sutured or otherwise closed as known to those skilled in the art.

FIGS. 33A and 33B illustrate a medical device 1500 for performing an LSH procedure, according to a tenth embodiment of the present disclosure. Medical device 1500 may include one or more features of the embodiments disclosed herein. For example, medical device 1500 may include a connector portion 1520, a manipulation device 1522, and a cutting device 1530. As an alternative to an elongate blade, cutting device 1530 may be located on an expandable member 1521. Cutting device 1530 may be any cutting device 1530 known to those skilled in the art, including, but not limited to, a ring affixed to expandable member 1521 or individual/segmented cutting portions affixed to expandable member 1521 at predetermined positions. Expandable member 1521 may be substantively similar to expandable members 18 and 26 of medical device 10, shown in FIG. 1. For example, expandable member 1521 may include an expansion line (not show) and may be any expandable member 1521 known to those skilled in the art, including, but not limited to, a balloon, a cage, and an open cell foam. In some embodiments, expandable member 1521 may be self-expanding. Expandable member 1521 may also include pressure sensors, pressure valves, and/or radiopaque markers for sensing and/or visualizing relative expansion of expandable member 1521.

Cutting device 1530 may include a retracted configuration (FIG. 33A) and a deployed configuration (FIG. 33B). In the retracted position, medical device 1500 may include a sheath 1524 that may protect tissue from cutting device 1530; and in the deployed configuration, sheath 1524 may be removed and expandable member 1521 may be expanded using techniques known to those skilled in the art. In use, a device operator may move sheath 1524 in the directions of arrow 1523 and expand expandable member 1521 into the deployed configuration, thus allowing cutting device 1530 to contact and pierce a patient's tissue. The device operator may further rotate a handle portion of medical device 1500 (not shown) in order to rotate manipulation device 1522 with cutting device 1530 relative to an elongate member (not shown), creating a uniform, rounded incision to excise the uterine fundus 510.

Figure 34B:
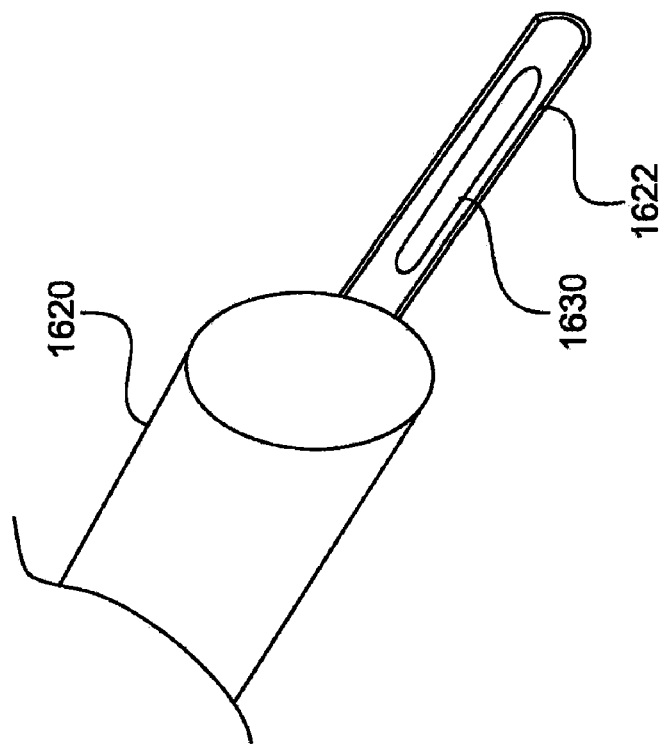
FIGS. 34A-34B are perspective views of another embodiment of a cutting device for performing a conization procedure.
Figure 34A:
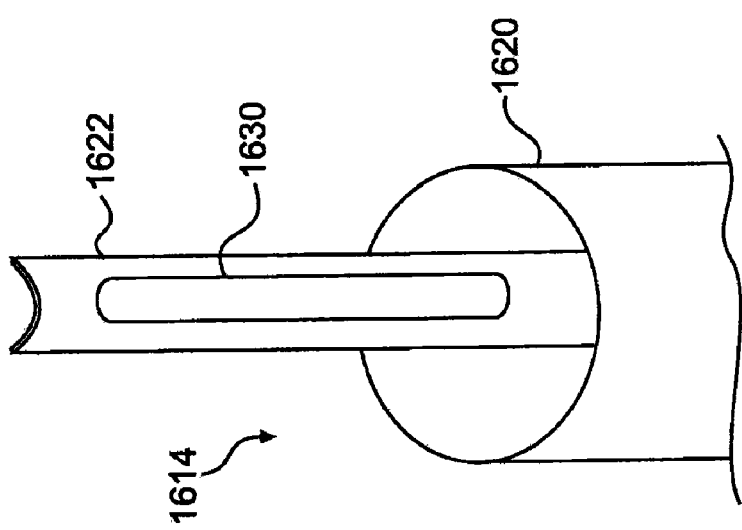

FIGS. 34A and 34B illustrate an end effector assembly 1614 for performing a conoscopy of the cervix, in accordance with an eleventh embodiment of the present disclosure. End effector assembly 1614 may include one or more features of end effector assemblies 1314 and 1414, shown in FIGS. 23 and 27, respectively. For example, end effector assembly 1614 may include a connector portion 1620, a manipulation device 1622, and a cutting device 1630. As an alternative to an elongate blade, cutting device 1630 may be a sharpened edge of an opening that is integral with manipulation device 1622. Further, manipulation device 1622 may be located at an outer edge of connector portion 1620 and may include a curved outer surface. Manipulation device 1622 may also be angled relative to a longitudinal axis of connector portion 1620. Edges of cutting device 1630 may be sharp enough to core out tissue as cutting device 1630 is rotated relative to an elongate member (not shown) during a conoscopy procedure.

Figure 35A:
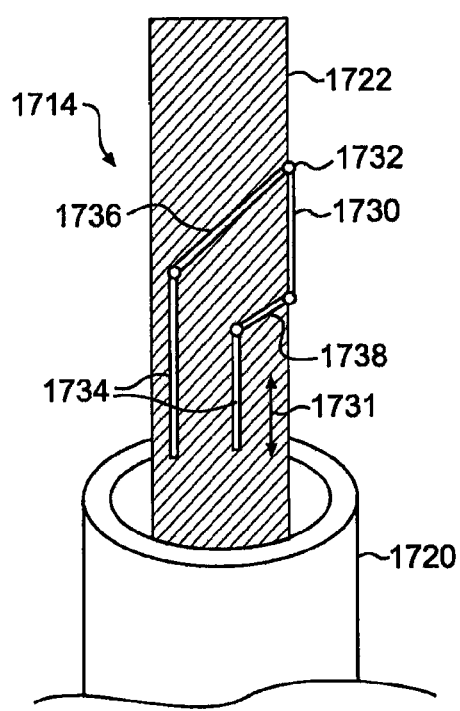
FIGS. 35A-35B depict another embodiment of a cutting device for performing a conization procedure, in retracted and deployed positions, respectively.
Figure 35B:
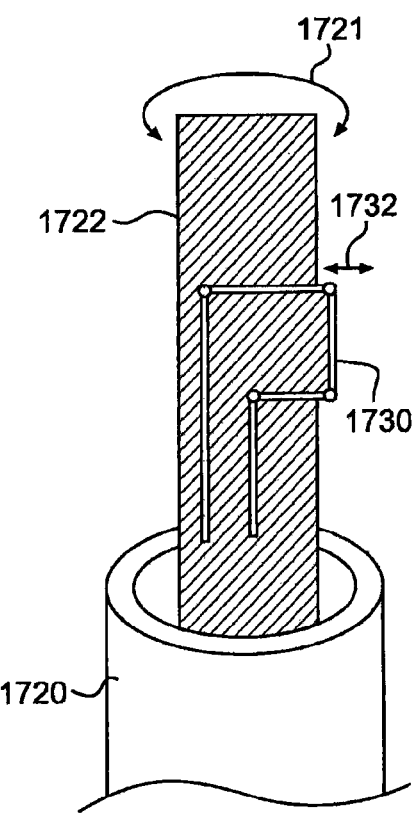

FIGS. 35A and 35B illustrate another end effector assembly 1714 for performing a conoscopy of the cervix, in accordance with a twelfth embodiment of the present disclosure. End effector assembly 1714 may include one or more features of end effector assemblies 1314 and 1414, shown in FIGS. 23 and 27, respectively. For example, end effector assembly 1714 may include a connector portion 1720, a manipulation device 1722, and a cutting device 1730. Cutting device 1730 may include a retracted configuration (FIG. 35A) and a deployed configuration (FIG. 35B). Cutting device 1730 may be any known cutting device to those skilled in the art, such as, for example, an elongate blade, and may be attached to deployment bars 1734, 1736, and 1738 per linkages 1732.

In use, a device operator may move first deployment bar 1734 in the direction of arrow 1731, and second deployment bars 1736, 1738 may be pivoted to a horizontal configuration (FIG. 35B), which may push cutting device 1730 out of manipulation device 1722. Manipulation device 1722 with cutting device 1730 may further be rotated relative to an elongate member (not shown) in the direction of arrow 1721 in order to core out cervical tissue during a conoscopy procedure. Alternatively, an end of cutting device 1730 may be disconnected from one second deployment bar 1736 or 1738 and linkage 1732 in order to deploy cutting device 1730 at a suitable angle for an LSH procedure.

Those of ordinary skill in the art will readily recognize that any of the above-described devices and methods, or aspects thereof, may be automated with the aid of, e.g., a computer or suitable processing circuitry. In such embodiments, the computer or processor may include suitable algorithms or logic to activate and effect any of the aspects described above. For example, the computer may be configured to effect deployment of a cutting device. In another embodiment, the computer may be configured to automatically move the cutting device to excise tissue.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A medical system, comprising:
   an elongate member having a longitudinal axis, a proximal end, a distal end, and a lumen extending therebetween;
   a handle connected to the proximal end of the elongate member;
   an end effector assembly connected to the distal end of the elongate member, wherein the end effector assembly includes an outer cup portion and an inner cup portion disposed within the outer cup portion; and
   a cutting device configured to extend from the end effector assembly, wherein the cutting device is configured to transition between a retracted configuration in which the cutting device is withdrawn into the end effector assembly and a deployed configuration in which the cutting device extends from the end effector assembly, wherein the cutting device is configured to rotate about the longitudinal axis and independently of the outer cup portion and the inner cup portion.

2. The medical system of claim 1, wherein the cutting device includes a blade.

3. The medical system of claim 1, wherein the end effector assembly includes an elongate manipulation member having a proximal portion, a distal portion, and a central portion extending therebetween, wherein the central portion includes a substantially uniform cross-section.

4. The medical system of claim 1, wherein a first actuator controls deployment of the cutting device and a second actuator controls rotation of the cutting device.

5. The medical system of claim 1, wherein the cutting device is a cauterizing instrument.

6. The medical system of claim 1, further comprising an expandable member secured to a distal portion of the medical system.

7. The medical system of claim 1, further comprising an elongate manipulation member extending distally from within the inner cup portion.

8. The medical system of claim 7, further comprising a first expandable member secured to a distal portion of the elongate member.

9. The medical system of claim 8, further comprising a second expandable member secured to the elongate manipulation member.

10. The medical system of claim 1, wherein a gap exists between the outer and inner cup portions, and the cutting device is slidably disposed within the gap.

11. The medical system of claim 1, wherein the end effector assembly is configured to pivot relative to the elongate member.

12. The medical system of claim 1, wherein a portion of the end effector assembly is removably secured to the distal end of the elongate member.

13. The medical system of claim 1, wherein the end effector assembly is longitudinally movable relative to the distal end of the elongate member.

14. The medical system of claim 1, wherein the cutting device is configured to transition between the retracted and the deployed configurations automatically.

15. The medical system of claim 1, further comprising a processor for controlling the transition of the cutting device between the retracted and the deployed configurations.

16. The medical system of claim 1, wherein rotation of the cutting device is electronically controlled.

17. A medical device, comprising:
   an elongate member having a longitudinal axis, a proximal end, a distal end, and a lumen extending therebetween;
   a handle connected to the proximal end of the elongate member;
   an end effector assembly connected to the distal end of the elongate member, the end effector assembly including an outer cup portion and an inner cup portion disposed at least partially within the outer cup portion; and a cutting device configured to extend from the end effector assembly, wherein the cutting device is configured to transition between a retracted configuration and a deployed configuration, wherein, when in the retracted configuration, an entirety of the cutting device is received within the outer cup portion and wherein the cutting device is configured to rotate about the longitudinal axis and independently of the outer cup portion and the inner cup portion.

18. The medical device of claim 17, wherein the cutting device includes a blade.

19. The medical device of claim 18, wherein a gap exists between the outer and inner cup portions, and the cutting device is slidably disposed within the gap.

20. The medical device of claim 17, wherein the cutting device is a cauterizing instrument.

21. The medical device of claim 17, wherein rotation of the cutting device is electronically controlled.

22. A medical system, comprising:
an elongate member having a longitudinal axis, a proximal end, and a distal end;
an actuator connected to the proximal end of the elongate member;
an end effector assembly operably connected to the distal end of the elongate member, wherein the end effector assembly includes an outer cup portion and an inner cup portion disposed within the outer cup portion; and
a cutting device configured to extend from the end effector assembly, wherein the cutting device is configured to transition between a retracted configuration in which the cutting device is at least partially withdrawn into the end effector assembly and a deployed configuration in which the cutting device extends from the end effector assembly, wherein the cutting device is configured to rotate about the longitudinal axis and independently of the outer cup portion and the inner cup portion.

23. The medical system of claim 22, further comprising a processor for controlling movement of the cutting device.

24. The medical system of claim 22, wherein the cutting device is configured to cauterize tissue.

25. The medical system of claim 22, further comprising a first expandable member secured to a distal portion of the elongate member.

26. The medical system of claim 22, further comprising an elongate manipulation member extending distally from within the inner cup portion, and a second expandable member secured to the elongate manipulation member.

27. A medical device, comprising:
an elongate member having a longitudinal axis, a proximal end, and a distal end;
an end effector assembly operably connected to the distal end of the elongate member, wherein the end effector assembly includes an outer cup portion and an inner cup portion disposed within the outer cup portion, wherein a gap is disposed between the outer cup portion and the inner cup portion; and
a cutting device configured to extend from within the gap, wherein the cutting device is configured to transition between a retracted configuration in which the cutting device is at least partially withdrawn into the gap and a deployed configuration in which the cutting device extends from the end effector assembly, wherein the cutting device is configured to rotate about the longitudinal axis and independently of the outer cup portion and the inner cup portion.

28. The medical device of claim 27, wherein the cutting device is a blade configured to cauterize tissue, and wherein portions other than an edge of the blade include a coating.

* * * * *